US007182771B1

(12) United States Patent
Houser et al.

(10) Patent No.: US 7,182,771 B1
(45) Date of Patent: Feb. 27, 2007

(54) VASCULAR COUPLERS, TECHNIQUES, METHODS, AND ACCESSORIES

(75) Inventors: Russell A. Houser, 1787 Verdite St., Livermore, CA (US) 94550; William D. Hare, Bethesda, MD (US)

(73) Assignee: Russell A. Houser, Livermore, CA (US)

( * ) Notice: Subject to any disclaimer, the term of this patent is extended or adjusted under 35 U.S.C. 154(b) by 526 days.

(21) Appl. No.: 10/326,211

(22) Filed: Dec. 20, 2002

Related U.S. Application Data

(60) Provisional application No. 60/428,509, filed on Nov. 22, 2002, provisional application No. 60/408,032, filed on Sep. 3, 2002, provisional application No. 60/399,710, filed on Aug. 1, 2002, provisional application No. 60/394,793, filed on Jul. 9, 2002, provisional application No. 60/385,216, filed on May 31, 2002, provisional application No. 60/381,805, filed on May 21, 2002, provisional application No. 60/369,835, filed on Apr. 5, 2002, provisional application No. 60/341,160, filed on Dec. 20, 2001.

(51) Int. Cl.
*A61B 17/11* (2006.01)
(52) U.S. Cl. .................. 606/155; 606/154; 623/1.36
(58) Field of Classification Search .......... 606/153, 606/154, 155, 213; 623/1.36
See application file for complete search history.

(56) References Cited

U.S. PATENT DOCUMENTS

| | | | |
|---|---|---|---|
| 5,904,697 A | 5/1999 | Gifford, III et al. | 606/155 |
| 5,989,276 A | 11/1999 | Houser et al. | 606/170 |
| 6,056,762 A | 5/2000 | Nash et al. | 606/153 |
| 6,152,937 A | 11/2000 | Peterson et al. | 606/153 |
| 6,176,864 B1 | 1/2001 | Chapman | 606/153 |
| 6,193,734 B1 | 2/2001 | Bolduc et al. | 606/153 |
| 6,206,913 B1 | 3/2001 | Yencho et al. | 623/1.3 |
| 6,241,743 B1 | 6/2001 | Levin et al. | 606/153 |
| 6,293,955 B1 | 9/2001 | Houser et al. | 606/153 |
| 6,361,559 B1 | 3/2002 | Houser et al. | 623/1.36 |

(Continued)

FOREIGN PATENT DOCUMENTS

WO    WO 99/63910 A1    12/1999    ................ 2/6

(Continued)

*Primary Examiner*—Michael J. Hayes
*Assistant Examiner*—M. Thomas Andersen
(74) *Attorney, Agent, or Firm*—Knobbe Martens Olson & Bear LLP

(57) ABSTRACT

A coupler is configured to connect a first tubular vessel to an aperture in a second tubular vessel. The coupler includes one or more radially extending members and a substantially nonmetallic tubular member. The substantially nonmetallic tubular member include an outer wall, an inner wall defining a lumen having an open distal end and an open proximal end, and a circumferential ridge encircling the outer wall, the radially extending members extending from the distal end of the tubular member. A method of fabricating a coupler the method including fabricating radially extending members; placing the radially extending members within a mold; injecting a material into the mold; allowing the material to cure to form the coupler; and removing the coupler from the mold. The coupler includes a tubular member having an outer wall, an inner wall defining a lumen having an open distal end and an open proximal end, and a circumferential ridge encircling the outer wall. The radially extending members extend from the distal end of the tubular member.

28 Claims, 70 Drawing Sheets

U.S. PATENT DOCUMENTS

| | | | |
|---|---|---|---|
| 6,371,965 B2 | 4/2002 | Gifford, III et al. | 606/153 |
| 6,391,036 B1 | 5/2002 | Berg et al. | 606/151 |
| 6,419,681 B1* | 7/2002 | Vargas et al. | 606/153 |
| 6,428,550 B1* | 8/2002 | Vargas et al. | 606/153 |
| 6,443,965 B1 | 9/2002 | Gifford, III et al. | 606/153 |
| 6,451,048 B1 | 9/2002 | Berg et al. | 623/1.13 |
| 6,494,889 B1 | 12/2002 | Fleischman et al. | 606/155 |
| 6,537,288 B2* | 3/2003 | Vargas et al. | 606/153 |
| 6,740,101 B2* | 5/2004 | Houser et al. | 606/153 |
| 6,776,785 B1* | 8/2004 | Yencho et al. | 606/153 |
| 6,843,795 B1* | 1/2005 | Houser et al. | 606/153 |
| 2001/0029383 A1 | 10/2001 | Solem | 606/153 |
| 2001/0051809 A1 | 12/2001 | Houser et al. | 606/153 |
| 2002/0013591 A1 | 1/2002 | Fleischman et al. | 606/155 |
| 2002/0029050 A1 | 3/2002 | Gifford, III et al. | 606/153 |
| 2002/0032462 A1 | 3/2002 | Houser et al. | 606/213 |
| 2002/0042622 A1 | 4/2002 | Vargas et al. | 606/153 |
| 2002/0052637 A1 | 5/2002 | Houser et al. | 623/1.1 |
| 2002/0058955 A1 | 5/2002 | Blatter et al. | 606/153 |
| 2002/0082613 A1* | 6/2002 | Hathaway et al. | 606/139 |
| 2002/0099393 A1 | 7/2002 | Fleischman et al. | 606/153 |
| 2002/0099394 A1 | 7/2002 | Houser et al. | 606/153 |
| 2002/0103534 A1 | 8/2002 | Vanney et al. | 623/3.1 |
| 2003/0167064 A1* | 9/2003 | Whayne | 606/153 |
| 2004/0068276 A1* | 4/2004 | Golden et al. | 606/153 |

FOREIGN PATENT DOCUMENTS

| | | | |
|---|---|---|---|
| WO | WO 99/65409 A1 | 12/1999 | 17/32 |
| WO | WO 00/15144 A1 | 3/2000 | 2/6 |
| WO | WO 00/24339 A1 | 5/2000 | 17/11 |
| WO | WO 01/41653 A2 | 6/2001 | 17/11 |
| WO | WO 03/005698 A2 | 1/2003 | |
| WO | WO 03/013370 A1 | 2/2003 | 17/11 |

\* cited by examiner

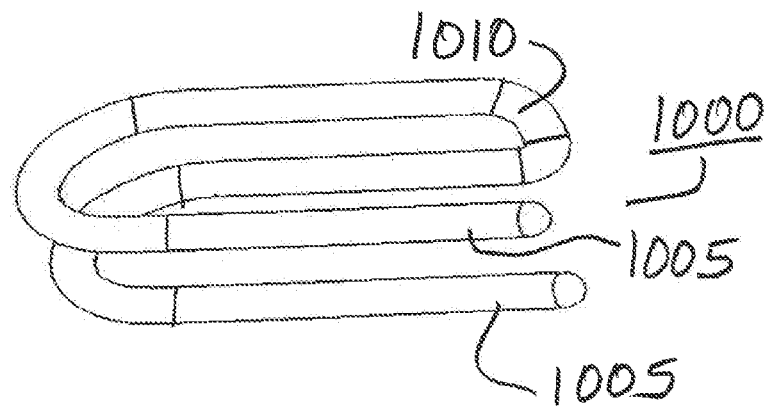
FIG. 68
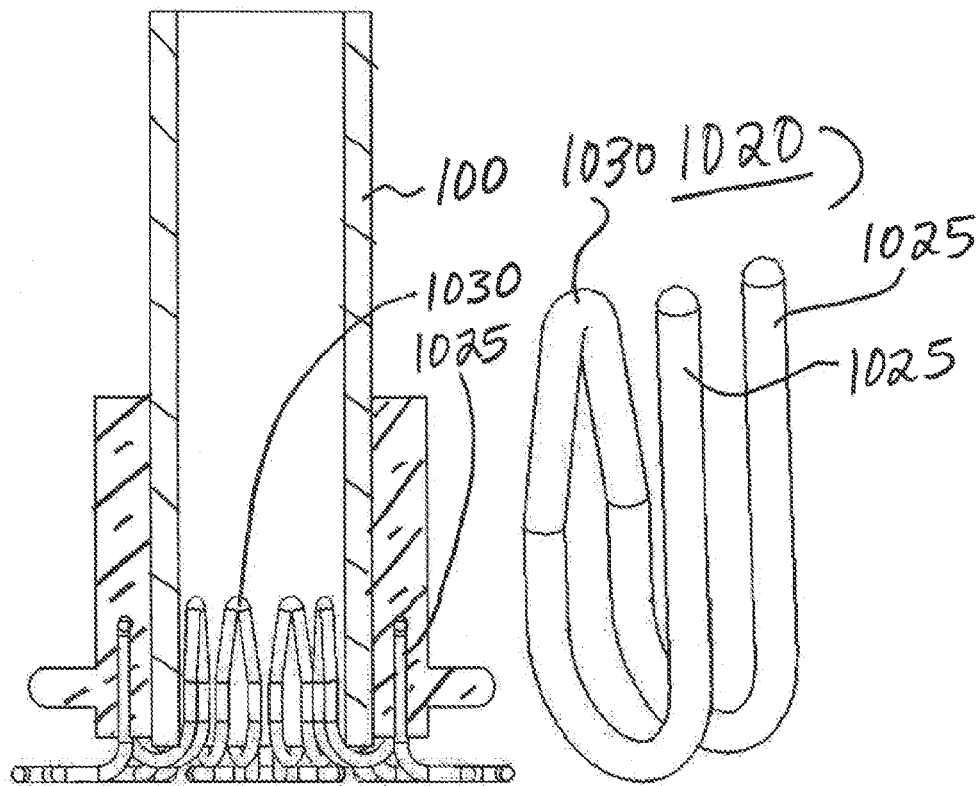
FIG. 69      FIG. 70

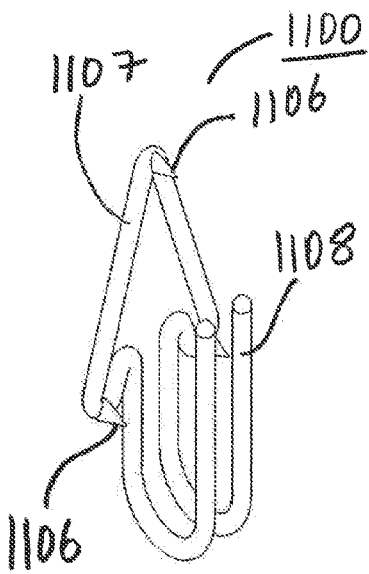
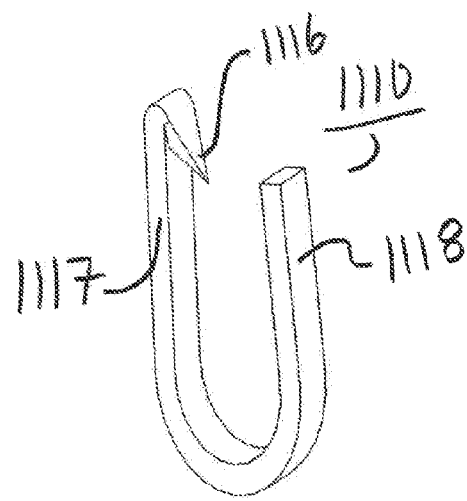
FIG. 77  FIG. 78
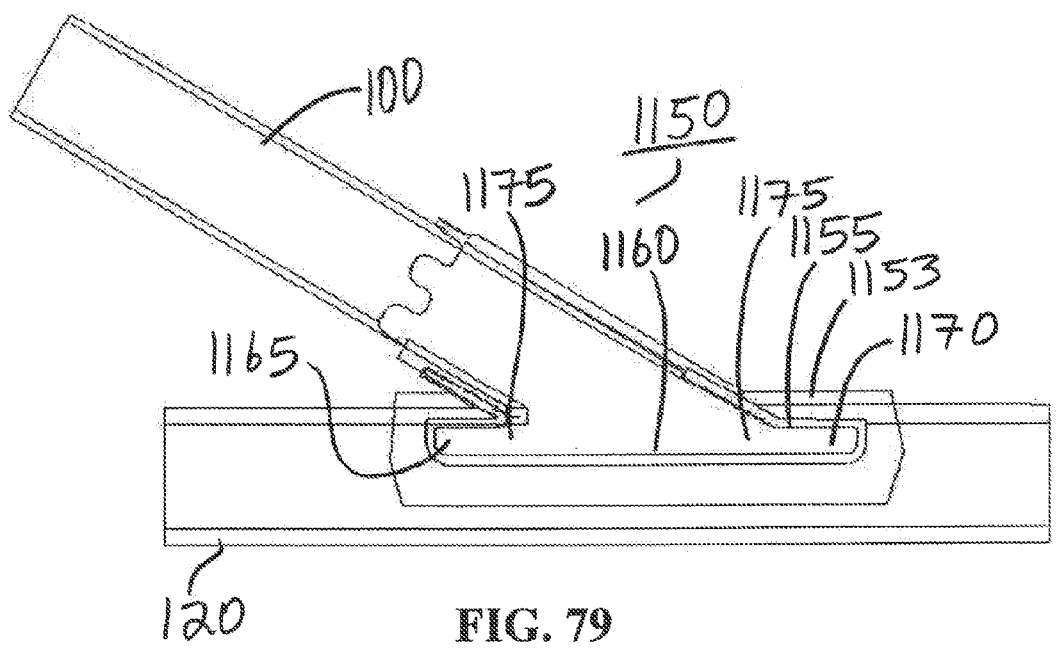
FIG. 79

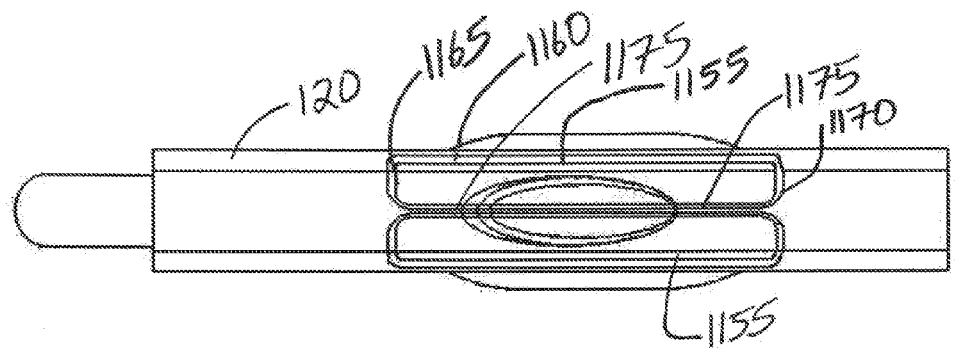
FIG. 80
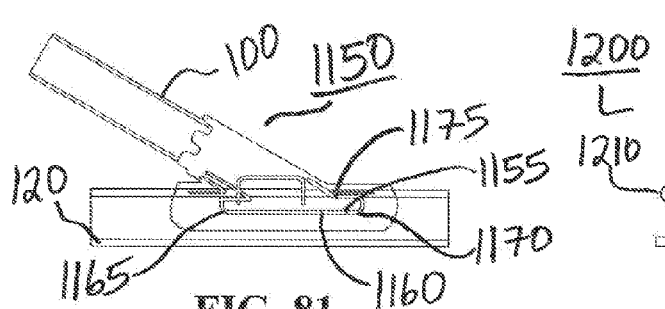
FIG. 81
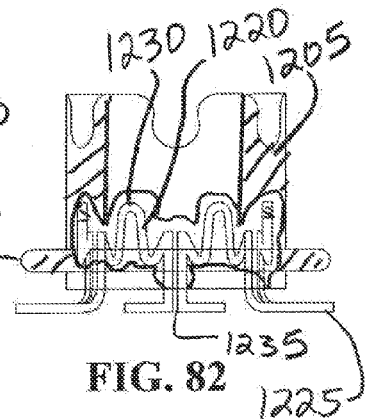
FIG. 82
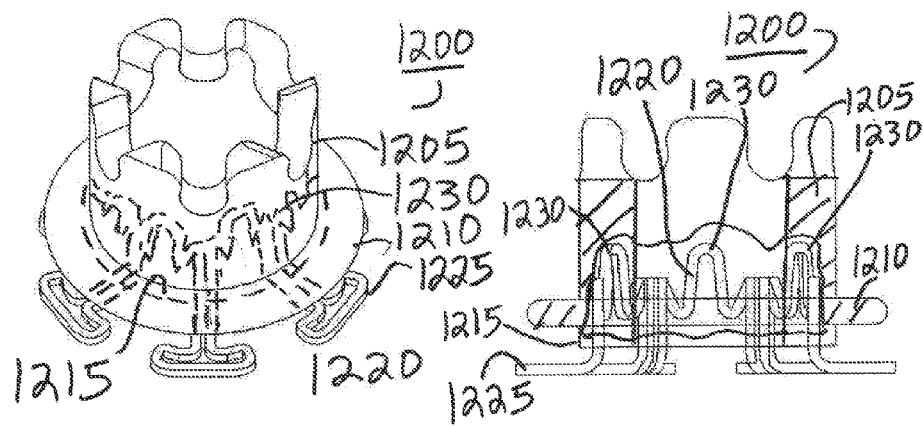
FIG. 83
FIG. 84

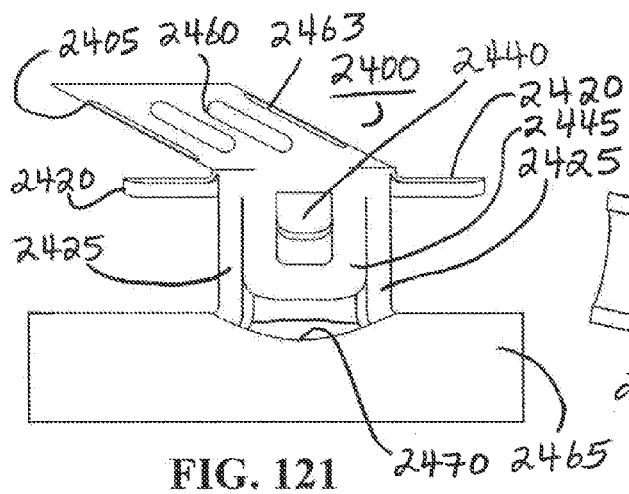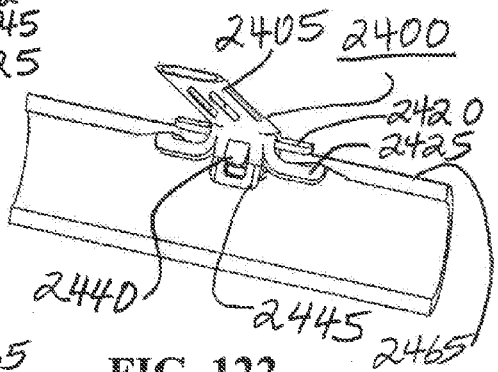
FIG. 121  FIG. 122
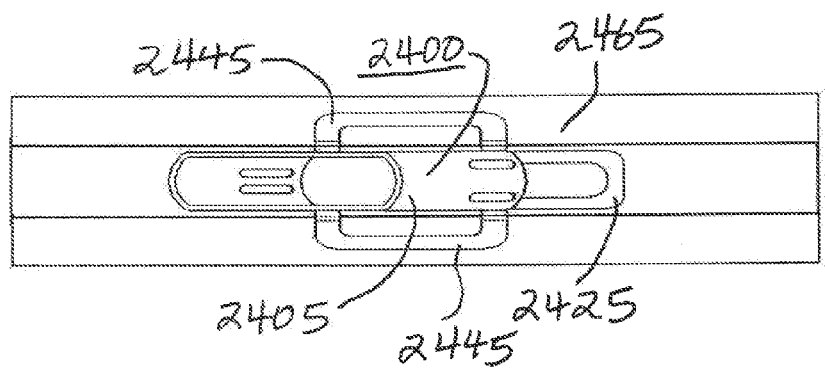
FIG. 123
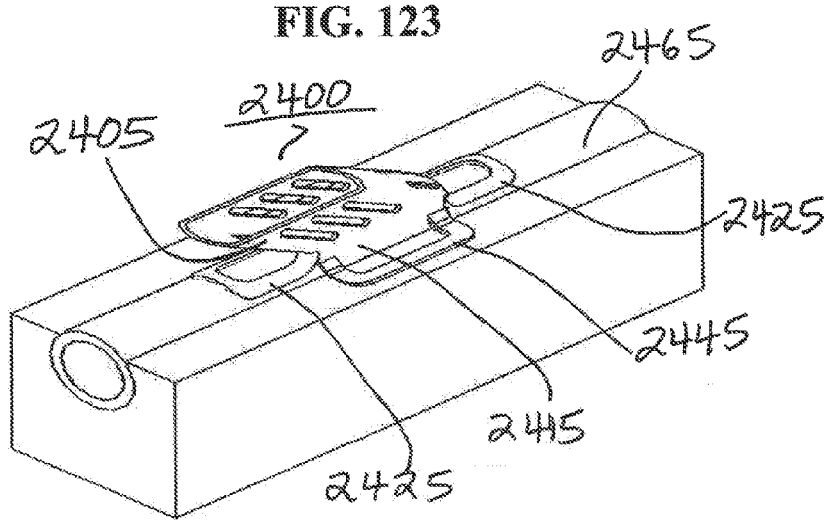
FIG. 124

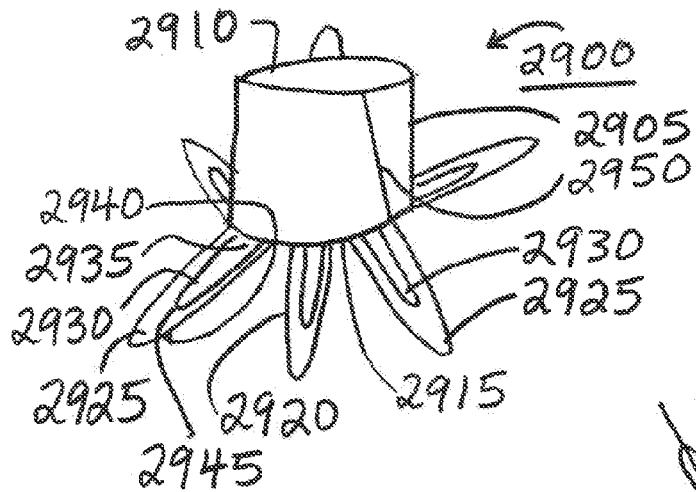
FIG.144
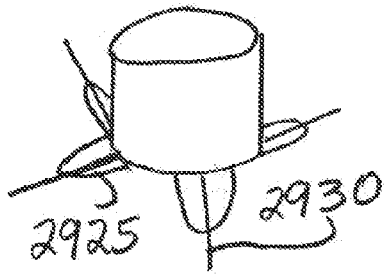
FIG.145
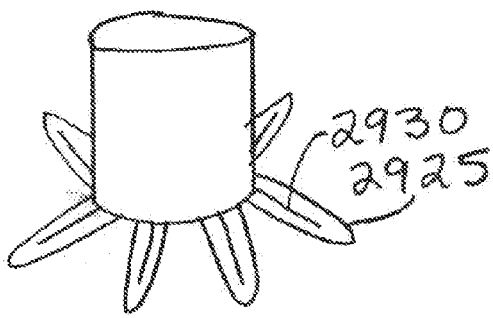
FIG.146
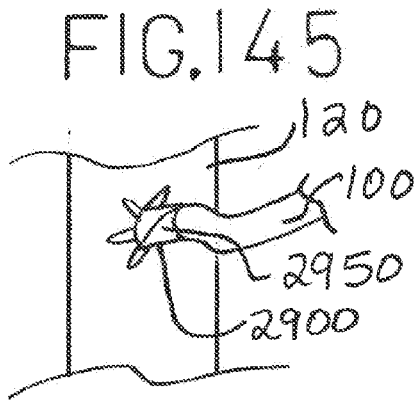
FIG.147
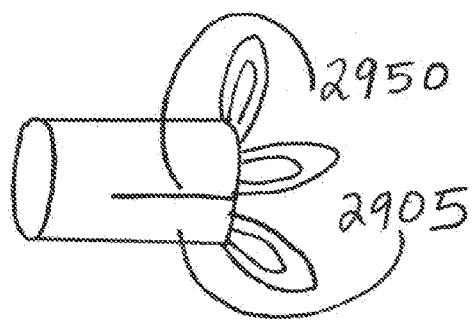
FIG.148

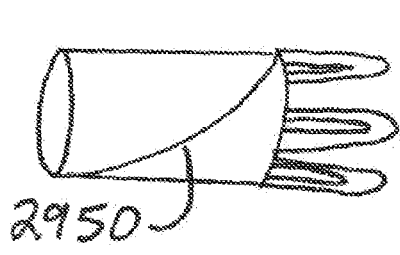
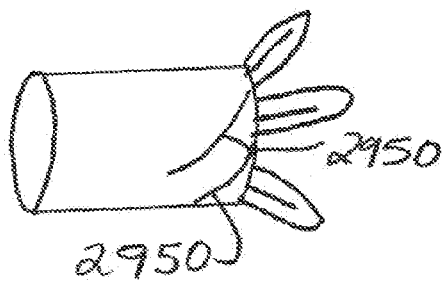
FIG.149   FIG.150
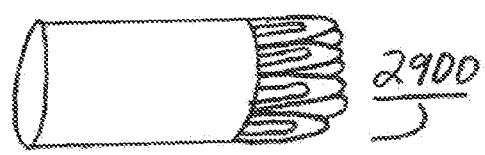
FIG.151   FIG.152
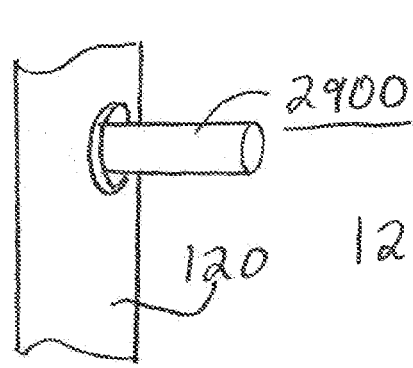
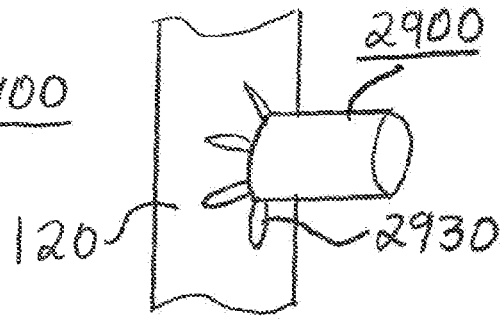
FIG.153   FIG.154

VASCULAR COUPLERS, TECHNIQUES, METHODS, AND ACCESSORIES

RELATED APPLICATIONS

This application claims priority from U.S. Provisional Patent Application 60/341,160 filed on Dec. 20, 2001 and titled Vascular Connectors, Techniques, Methods, and Accessories; 60/369,835 filed on Apr. 5, 2002 and titled Vascular Couplers, Techniques, Methods, and Accessories; 60/381,805 filed on May 21, 2002 and titled Vascular Couplers, Techniques, Methods, and Accessories; 60/385,216 filed on May 31, 2002 and titled Anastomic Coupler with Valve; 60/394,793 filed on Jul. 9, 2002 and titled Sutured Anastomotic Coupler Device and Method of Use; 60/399,710 filed on Aug. 1, 2002 and titled Vascular Couplers, Techniques, Methods, and Accessories; 60/408,032 filed on Sep. 3, 2002 and titled Vascular Couplers, Techniques, Methods, and Accessories; and 60/428,509 filed on Nov. 22, 2002 and titled Vascular Couplers, Techniques, Methods, and Accessories.

TECHNICAL FIELD

The field of the inventions generally relates to cardiovascular and vascular devices, and, more particularly, to vascular couplers.

BACKGROUND

Cardiovascular diseases are typically treated pharmacologically, using interventional cardiology, and surgically. For example, interventional, catheter-based treatments include percutaneous transluminal coronary angioplasty ("PTCA") with an angioplasty balloon to compress plaque to the wall of a coronary vessel, placement of a stent in a vessel to maintain the patency of the vessel, and atherectomy to use a cutting instrument to shave off and remove plaque from the lumen of the vessel. Surgical treatments include coronary artery bypass grafting procedures using cardiopulmonary support, beating heart techniques, minimally invasive approach, and robotically assisted instruments. In these procedures, the surgeon may use traditional, endoscopic, and/or laparoscopic instruments. In traditional coronary artery bypass grafting, the surgeon uses sutures to anastomose a synthetic or natural bypass vessel to, for example, the aorta at one end and a coronary artery at the other end, or from the internal mammary artery ("IMA") to a coronary artery. To form an anastomosis between an internal mammary artery and a coronary artery, blood flow through the internal mammary artery must be temporarily stopped, typically by applying a removable clamp to the mammary artery. The mammary artery is then severed downstream from the clamp to create a free end. An incision is created in the target coronary artery downstream of the blockage. The free end of the mammary artery can then be connected to the incision in the coronary artery, typically by suturing, such that blood can flow from the mammary artery through the incision into the coronary artery. Typical traditional coronary artery bypass grafting procedures involve aortic clamping and a procedure time of approximately ten to twenty minutes per anastomosis.

Some of the other devices used in beating heart and/or minimally invasive surgical treatments are produced by companies that include Converge Medical, Inc. (formerly Advanced Bypass Technologies, Inc.), By-Pass, Cardica (formerly Vascular Innovations), Coalescent Surgical, Corvascular, Ethicon, HeartPort, Heart-Tech, Intellicardia, Onux Medical, Origin MedSystems, Inc. (Guidant), St. Jude Cardiovascular Group (including Vascular Science), Sulzer Carbomedics, Vasconnect, and Ventrica.

SUMMARY

In one general aspect, a coupler configured to connect a first tubular vessel to an aperture in a second tubular vessel. The coupler includes one or more radially extending members and a substantially nonmetallic tubular member. The substantially nonmetallic tubular member comprising an outer wall, an inner wall defining a lumen having an open distal end and an open proximal end, and a circumferential ridge encircling the outer wall, the radially extending members extending from the distal end of the tubular member.

Embodiments of the coupler may include one or more of the following features. For example, the extending member may include a first segment and a second segment, the first segment being at an angle of 90° or less with respect to the second segment, the first segment extending from the tubular member. The second segment defines a region that is wider than a region defined by the first segment. The extending member may include a nickel titanium alloy and/or 17-7PH stainless steel. The proximal end of the tubular member may include a strain relief.

The coupler may further include at least one securing member mounted to the distal end of the tubular member, the securing member including a first segment positioned adjacent to the inner wall, a second segment positioned against the outer wall, and a third segment connecting the first segment and the second segment.

The coupler may further include at least one securing member mounted to the distal end of the tubular member, the securing member including a first segment positioned adjacent to the inner wall, a second segment positioned within the wall between the inner wall and the outer wall, and a third segment connecting the first segment and the second segment. The coupler may further include a gasket extending from the distal end of the tubular member, the radially extending members extending from the gasket. The tubular member may include one or more of silicone, ePTFE, polyurethane, and polyisoprene.

The coupler may further include a gasket extending from the distal end of the tubular member and a strain relief extending from the proximal end of the tubular member. The tubular member, the ridge, the gasket, and the strain relief are an integral unit.

In another general aspect, a method of fabricating a coupler the method including fabricating radially extending members; placing the radially extending members within a mold; injecting a material into the mold; allowing the material to cure to form the coupler; and removing the coupler from the mold. The coupler includes a tubular member having an outer wall, an inner wall defining a lumen having an open distal end and an open proximal end, and a circumferential ridge encircling the outer wall. The radially extending members extend from the distal end of the tubular member.

Embodiment of the method may include one or more of the following. For example, the method may further comprise inserting one or more securing members at least partially within the mold. Fabricating the radially extending members comprises chemically etching a sheet of a metal alloy. Fabricating the radially extending members further comprises one or more of forming, annealing, chemical polishing, and electropolishing.

Allowing the material to cure to form the tubular member further comprises forming a ridge member around at least a portion of a circumference of the tubular member, forming a strain relief at the proximal end of the tubular member, and forming a gasket at the distal end of the tubular member. The material comprises one or more of silicone, ePTFE, polyurethane, and polyisoprene.

In another general aspect, a method of deploying a coupler includes forming an opening in a wall of a tubular vessel; deflecting the radially extending members into a longitudinally extending configuration; inserting the extending members at least partially into the opening; and releasing the extending members. The coupler includes one or more radially extending members, a substantially nonmetallic tubular member, the tubular member comprising an outer wall, an inner wall defining a lumen having an open distal end and an open proximal end, and a circumferential ridge encircling at least a portion of the outer wall, the radially extending members extending from the distal end of the tubular member.

Embodiments of the method may include one or more of the following features. For example, deflecting the radially extending members into a longitudinally extending configuration further includes deflecting the radially extending members and at least partially inserting the extending members into an opening in a deployment tool, the deployment tool including a handle and a distal plate, the distal plate including the opening. Releasing the extending members further includes placing the plate on the vessel and removing the plate from around the coupler, the removal of the plate allowing the extending members to return to the radially extending configuration.

The couplers described herein enable clampless-bypass surgery. By not utilizing a clamp on the aorta, this method has the potential to significantly reduce the incidence of postoperative cognitive dysfunction (POCD), which occurs in up to approximately 50% of patients undergoing coronary artery bypass grafting (CABG) surgery.

Benefits that can be provided by the vascular couplers described herein include: (1) a coupler system that enables clampless bypass surgery—minimizing aortic manipulation by not requiring cross-clamping or aortic side-biting during coronary artery bypass grafting (CABG); (2) allowing or augmenting radial vessel expansion and contraction similar to a sutured anastomosis; (3) single piece coupler design in which no separate external vessel component (e.g., collar) is required; (4) reinforced anastomosis area (top vessel ridge) for mechanical securing and acute hemostasis; (5) limited foreign material contact with blood or vessel (even with non-everted versions); (6) includes sutureless, sutured or combination versions; (7) includes aortic (proximal), coronary (distal), peripheral and valved versions for completeness; (8) does not enlarge or expand punch hole or arteriotomy during deployment; (9) once deployed, the coupler can ensure that all petals are in contact with the inside vessel wall; (10) no introducer or plunger is required for coupler deployment (although alternative versions may utilize these or similar accessories); (11) ability to employ multiple coupler deployment methods (push in, partially pull out; twist and advance; forward deflected (superelastic) or forward positioned (shape memory) petals during deployment, and allowed to recover to their annealed configuration, etc.); (12) couplers coated and/or embedded with therapeutic materials to positively affect healing; (13) much less costly to use with respect to other current systems because there are fewer components and accessories required; and (14) the coupler system is easy to learn and easy to use.

DESCRIPTION OF THE DRAWINGS

FIG. 7d is a cross-sectional side view of a vascular coupler implanted in a blood vessel, such as a coronary artery.

FIGS. 57–60 are top, side, and cross-sectional side views of a stand-alone valve that can be easily implanted in tissue using a minimally invasive surgical procedure.

FIGS. 67–72 illustrate securing members that do not penetrate tissue.

FIGS. 73–78 illustrate tissue penetrating securing members.

FIGS. 79–81 are side, bottom, and cross-sectional side views of a vascular coupler having longitudinal wire or rod petals embedded in an overmolded ridge.

FIGS. 82–87 illustrate vascular couplers having circumferential spring member in the stem.

FIGS. 108 and 109 are perspective views of the deployment tool of FIG. 103 deploying a non-overmolded, angled vascular coupler.

FIGS. 109–116 illustrate various views of a non-overmolded, angled vascular coupler having a partial longitudinal slot.

FIG. 121 is a side view of the flat-sided vascular coupler of FIG. 117 being inserted into an artery.

FIG. 122 is a perspective side view of the vascular coupler of FIG. 117 inserted in an artery.

FIGS. 123 and 124 are top and perspective views of the vascular coupler of FIG. 117 inserted into an artery.

FIG. 144 illustrates a multi-element vascular coupler having a longitudinal slot.

FIGS. 145 and 146 illustrate a multi-element vascular coupler having wire and U-shaped petals and a longitudinal slot.

FIG. 147 illustrates the vascular coupler of FIG. 144 implanted in a vessel.

FIG. 148 illustrates a vascular coupler having a partial longitudinal slot.

FIG. 149 illustrates a vascular coupler having a complete spiral slot.

FIG. 150 illustrates a vascular coupler having a multiple, partial spiral slots.

FIG. 151 illustrates a compressed vascular coupler.

FIG. 152 illustrates a vascular coupler having the flexible petals extended to reduce the profile.

FIGS. 153 and 154 illustrate a manual method of placing a vascular coupler within a vessel.

DETAILED DESCRIPTION

Figure 1:
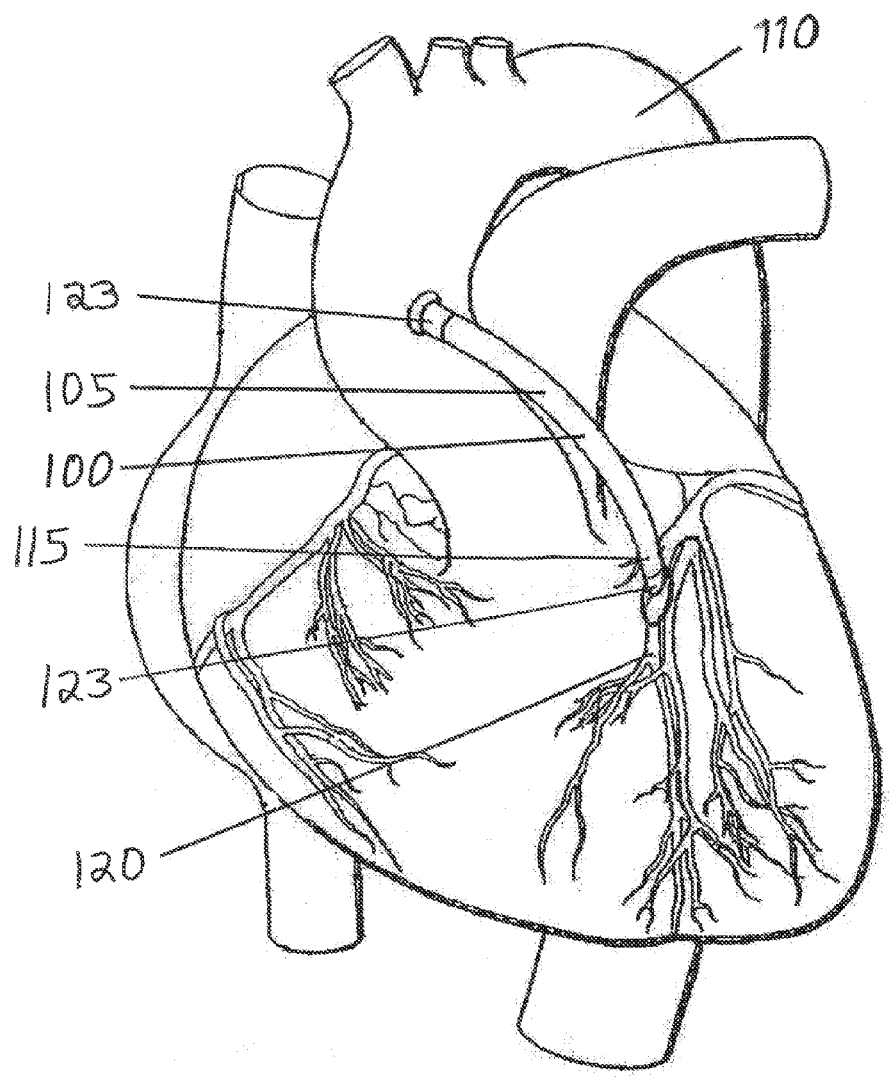
FIG. 1 is a perspective view of a heart in which vascular couplers are used to form a vascular bypass between the aorta and a coronary artery.
Figure 2:
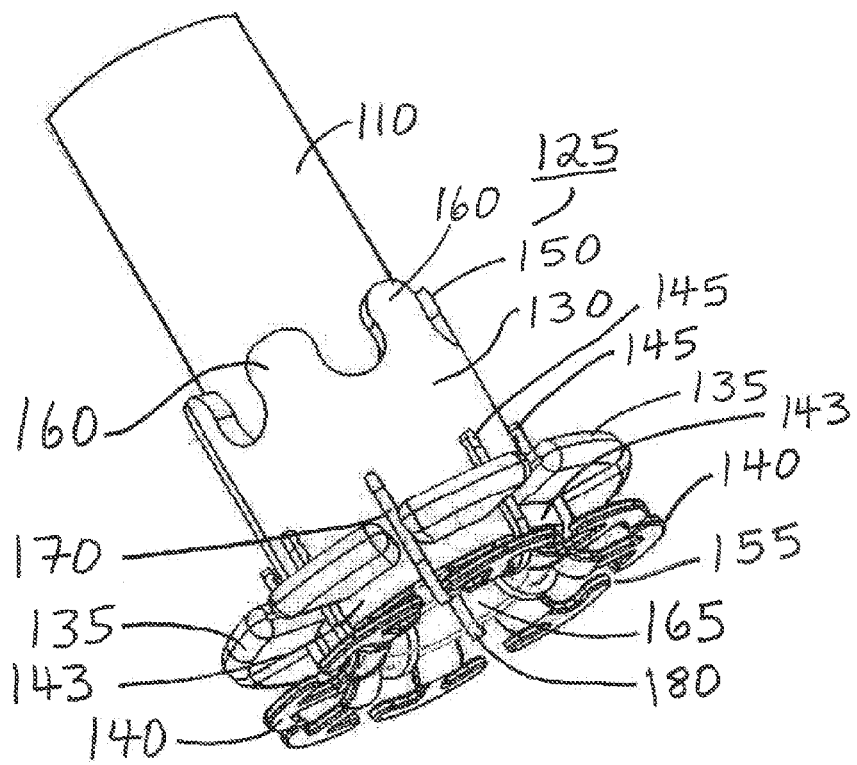
FIG. 2 is a front perspective view of a vascular coupler.
Figure 3:
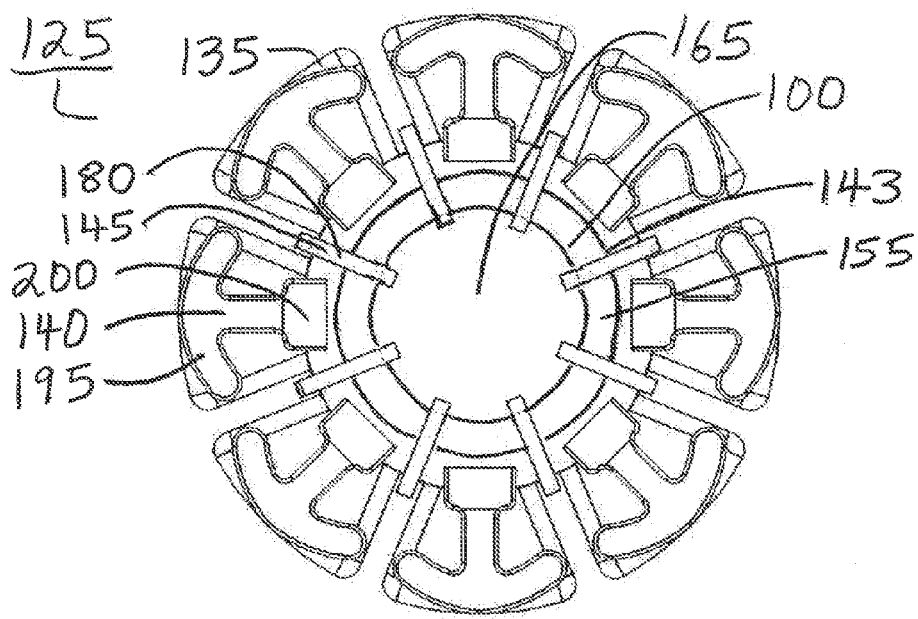
FIG. 3 is a bottom view of the vascular coupler of FIG. 2.
Figure 4:
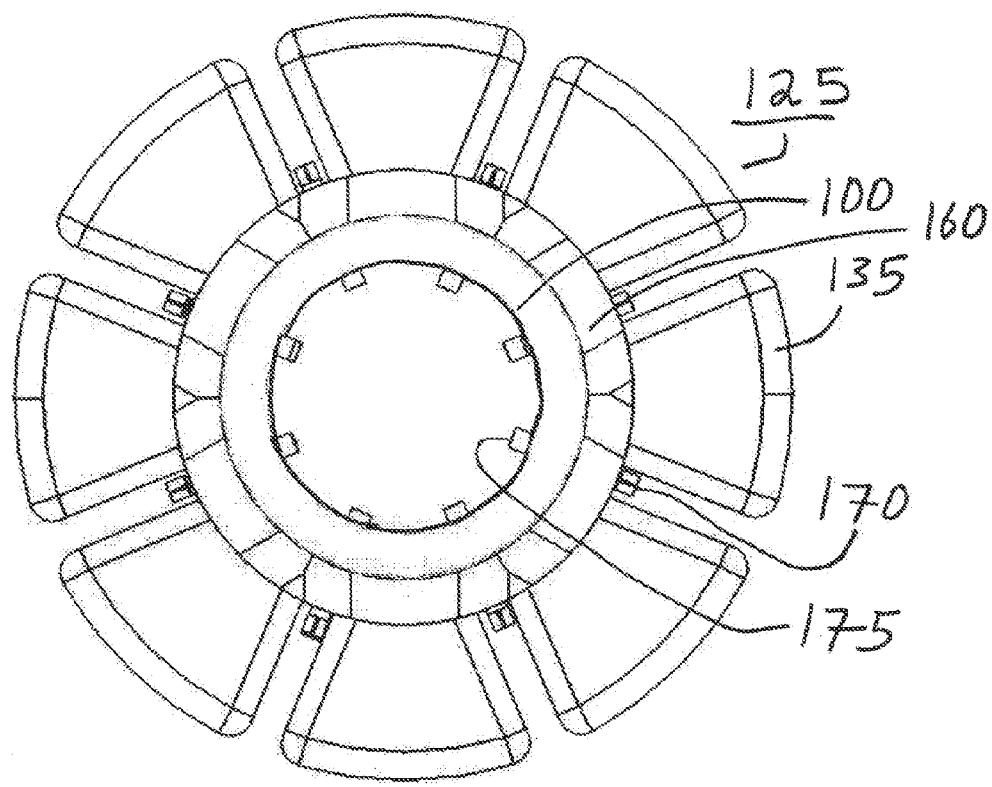
FIG. 4 is a top view of the vascular coupler of FIG. 2.
Figure 5:
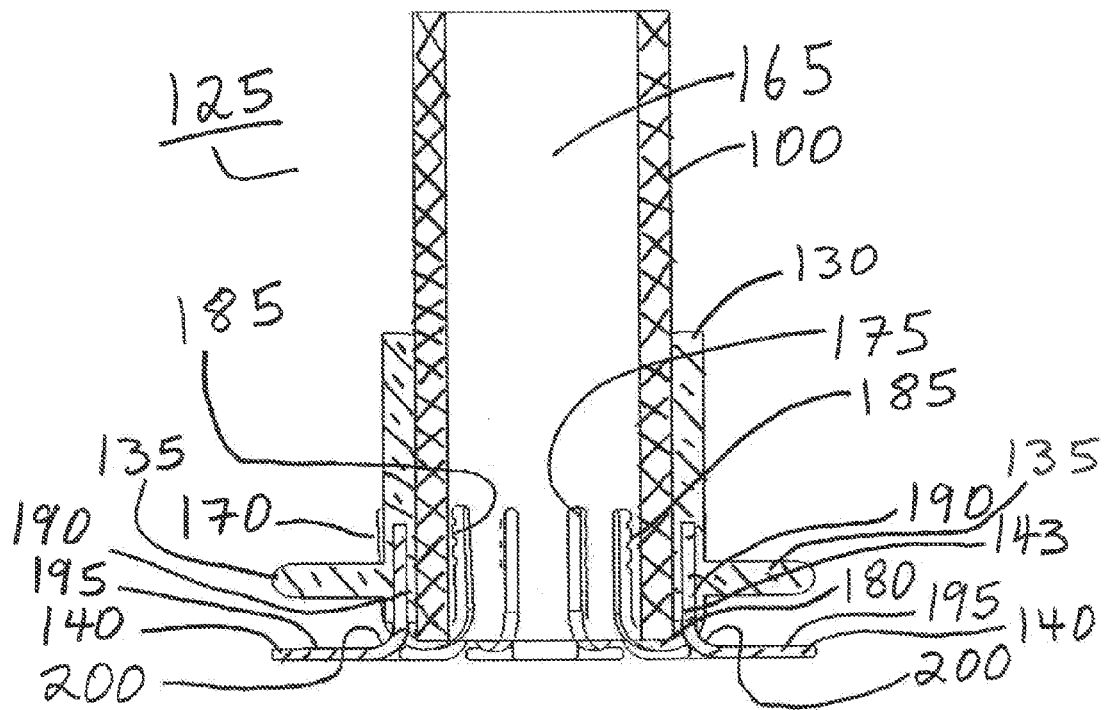
FIG. 5 is a cross-sectional side view of the vascular coupler of FIG. 2.

Referring to FIG. 1, a bypass vessel or graft 100 is connected at a proximal end 105 to the aorta 110 and at a distal end 115 to a coronary artery 120. At least one of the connections between the graft 100 and the aorta 110 and between the graft and the coronary artery 120 is formed using a vascular coupler or connector 123, as described in greater detail below. The vascular couplers described herein enable physicians to perform clampless bypass surgery and can function as sutureless anastomosis couplers. Novel features of some of the vascular couplers described herein include the overmolded stem/strain relief, ridge, and hemostatic gasket that are created using a compliant/elastic/flexible material. Overmolding these components is advantageous because they are not simply a coating or covering of an existing structure (which may also be used) but instead are an integral component.

In general, the overmolded vascular coupler can be fabricated using multiple, independent petals around which an overmolded component is fabricated. In general, a multi element or multi petal vascular coupler is overmolded with a compliant material, allows for radial expansion and contraction, and functions similarly to a traditional sutured anastomosis because this design allows for pulsatile, compliant, radial motion. To vary or tailor compliance, multiple slots, groves, hinges, reduced wall thickness areas may be formed in between the petal elements, and may increase the radial flexibility/compliance. Moreover, this general design provides for radial compression without a slit through the stem wall, and without the use of a hinge. This design also advantageously provides overlapping vessel-contacting petals because that feature is generally only possible when fabricating the vascular coupler from multiple, independent petals/elements—this is not possible for couplers that are fabricated from a single tube. This design also advantageously allows for the end of the petals extending outwardly from the stem to be larger (i.e., widen) as it extends away from the stem. Using multiple independent petals also allows for complete vessel contact by having overlapping petals at the site of the aortic punch or core site, and the arteriotomy for the coronary anastomosis. These features and advantages are discussed in more detail below.

In general, the overmolded multiple element versions of the vascular coupler is applicable as an aorta vascular coupler, coronary vascular coupler and peripheral vascular coupler. The range of diameters for the vascular couplers can be, for example, between approximately 1.0 mm and 4 mm (or larger for peripheral versions), and can be angled at between approximately 20 and 90 degree angles, or other, and be round, oval or other desired geometry.

Referring to FIGS. 2–5, a vascular coupler 125 includes a stem 130, ridges 135, petals 140, a hemostatic gasket 143, and securing members 145. The bypass vessel 100, such as an internal mammary artery (IMA) or saphenous vein, extends from the stem 130 at a proximal end 150 of the coupler 125 and terminates within the coupler at a distal end 155. The stem 130 includes strain relief members 160 that extend proximally from the proximal end 150 of the stem and provide strain relief to the vessel 100. Although only one embodiment of the strain relief members is illustrated in these figures, other strain relief configurations are applicable for use with the coupler 125. For example, the strain relief may have a straight, slotted, or sinusoidal edge to provide more of a compliance transition area or region. Additionally, the wall thickness of the strain relief may be reduced in the direction of the proximal edge to increase flexibility.

The securing members 145 are generally U-shaped and include an outer arm 170, an inner arm 175, and a connecting portion 180 that connects the outer arm to the inner arm. The outer arm 170 extends along the outer surface of the coupler 125, the connecting portion 180 extends across the distal end 155 of the coupler, and the inner arm 175 extends along and against the vessel 100 in the inner lumen 165 of the coupler. The outer arm 170 and the inner arm 175 include one or more protrusions 185 that, when the arms are compressed against the vessel 100 and the stem 130, provide resistance to pulling the vessel out of the coupler 125. The protrusions 185 can be of any configuration that provides resistance to pulling the vessel out of the coupler. For example, the protrusions can be in the form of a roughened surface or tissue penetrating pins. The securing members 145 can be made of, for example, a biocompatible superelastic, shape memory, or deformable metal or plastic that can be moved from an open position to a closed position. In the open position, the stem 130 and the vessel 100 can be inserted into a gap formed between the outer arm 170 and the inner arm 175. In the closed position, the gap is reduced to compress or hold the position of the vessel 100 relative to the stem 130. Thus, if the securing members 145 are made of a superelastic material, such as Nitinol, the securing members are formed to be in the closed position and the gap formed by exerting a opening force to the arms 170, 175. When that force is removed, the gap is reduced as the arms move towards each other. Similarly, if the securing members are made of a deformable material, a force is applied to close the gap by moving the arms towards each other.

The stem 130 and hemostatic gasket 143 are made of a biocompatible elastic/compliant/flexible material, including ePTFE, silicone, or polyurethane. The stem 130 includes the ridges 135, which extend outwardly from the circumference of the stem circumferentially adjacent to the petals 140. Each petal 140 includes a first arm 190 that is connected to a second arm 195 through a transition region 200. In this embodiment, the second arm has a generally T-shape, although many other shapes also are suitable if they adequately compress the receiving vessel (i.e., the vessel being bypassed) between the ridges 135 and the petals 140. The petals 140 extend from the distal end 155 of the stem 130, the first arm 190 being embedded within the stem 130, the transition region 200 extending from the stem 130 and the second arm generally parallel to the ridges 135. The petals 140 are made from a superelastic/shape memory material, such as Nitinol, a nickel-titanium alloy. In this manner, the petals 140 can be moved from a deflected position to a released position. FIGS. 2–5 illustrate the petals 140 in the released position. In the deflected position, the petals 140 are oriented approximately 90° such that they are generally collinear with the stem 130. As explained in greater detail below, by placing the petals 140 in the deflected position using a compressing force, the petals can be inserted into an opening in the receiving vessel and then the compressing force removed such that the petals return to the released position, thereby trapping the vessel wall between the ridges 135 and the petals 140. The petals are illustrated as being sheet-like. However, other starting materials can be used, such as a wire. One benefit of using a wire to fabricate the petals is a reduction in the amount of foreign material that is implanted and/or in the blood stream. The greater the surface area of the petals, the longer it takes to endothelialize that surface. As such, petals can be fabricated to have less than 0.020 inches of surface width so that the area needed to be endothelialized is reduced, providing benefits to the patient.

Figure 6:
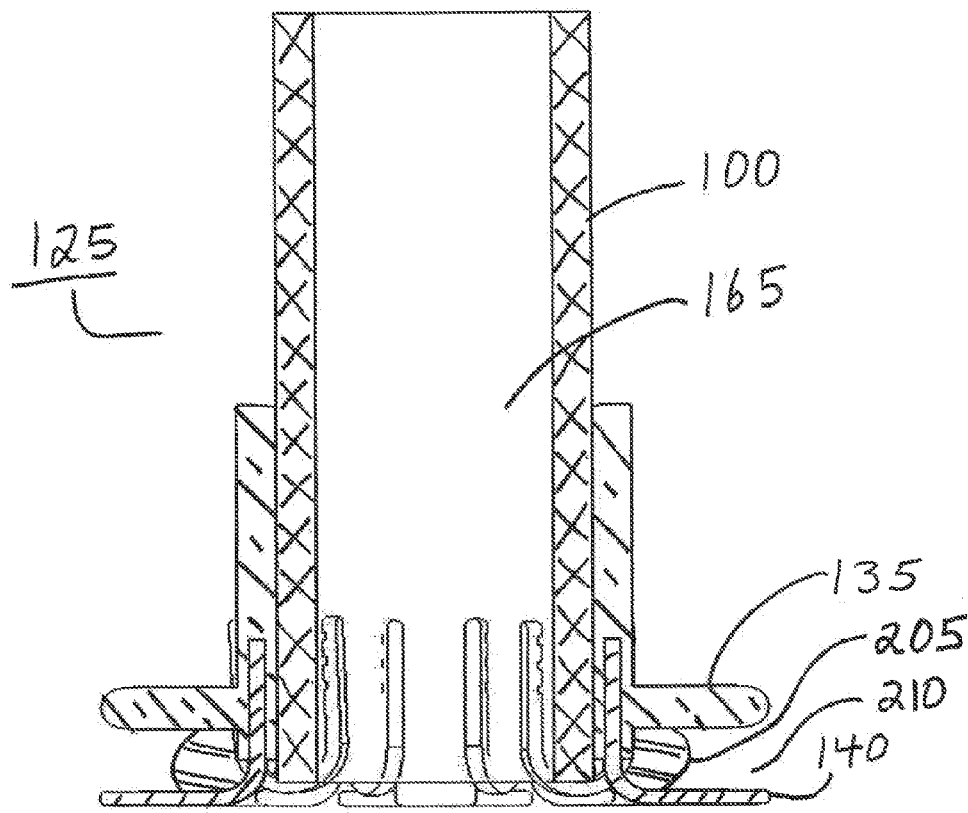
FIG. 6 is a cross-sectional side view of the vascular coupler of FIG. 2 with a hemostatic gasket mounted to the coupler.

Referring to FIG. 6, the vascular coupler 125 can be fabricated with an optional enlarged hemostatic gasket 205 positioned around the circumference of the hemostatic gasket 143 within a space 210 defined between the ridges 135 and the petals 140. The space 210 receives the vessel wall of the vessel in which the coupler is implanted. The enlarged hemostatic gasket 205 provides additional sealing function in the event that there is play or looseness in the interface between the opening in the receiving vessel and the stem after the coupler is implanted. The compliance of the gasket 205 is atraumatic to the vessel edges, as well as assists sealing and mechanical securement.

The coupler 125 can be fabricated using many methods known to those of skill in the art. One representative method is described below. In these methods, the petals and securing members may be produced at the same time, either as individual separate components or connected together. Initially, the desired pattern of the petals and securing members is chemically etched onto a flat sheet of superelastic/shape memory material, such as Nitinol. The etching produces the coupler components. The resulting cross section geometry of the parts may be round, oval, square, square with rounded corners, or any other suitable shape. The etched pattern then is bent and/or annealed into a specific shape using a suitable fixture. The ends of the etched pattern then are joined together by using one or more of several methods including, for example, (1) inserting an end that includes a tab into a slot, groove, or hole; and (2) soldering, welding, adhesively bonding, or applying any other suitable joining process to the ends. Alternatively, the section or sections may not be joined, or otherwise attached together. The desired shape is imparted by the bending and/or annealing described above. The design that does not incorporate joining may allow additional flexibility at one or more regions of the coupler.

In the method described above, there are additional optional steps. For example, the etched pattern can be chemically polished or electropolished. In particular, the elements that will come in contact with blood and/or tissue may be polished. If desired or necessary, the etched pattern may be bent and/or annealed using the fixture one or more additional times to better form the elements' shapes and/or to impart a sharp curve or bend that would not be possible to impart with single annealing. Similarly, an etching or grinding process may be used to reduce the thickness of the sheet or other starting material, which additionally removes any unwanted material.

Once the parts are etched, shaped (annealed), electropolished (if desired), and joined, as each of these steps are necessary, the etched and formed pattern then is placed into a mold and overmolded to produce the ridges 135, stem 130, strain relief 150, and hemostatic gasket 205. The coupler 125 next may be coated (e.g., dipped, sprayed, vacuum-assisted impregnation, or other suitable process or method) with a therapeutic or pharmacologic compound or material. The hemostatic gasket may be fabricated in a second, subsequent overmolding step using the same or a different material.

Of course, other methods and steps for fabricating the coupler can be substituted for the above process. For example, alternative machining methods to the chemical etching steps include but are not limited to photo-etching, electron discharge machining (EDM), laser cutting, grinding, traditional cutting. Similarly, alternative substrates or starting materials that can be used instead of the flat sheet include but are not limited to wire, rod, hoop, tube (e.g., having a round, square, or other geometry), coil, strip, or band. Instead of the overmold fabrication method of the stem, strain relief, and ridge, other methods may be used, including but are not limited to extrusion, casting, molding (injection or other), sintering, dip coating, spraying, weaving, laminating, stereo lithography (i.e., 3-D layering).

The vascular couplers described above (i.e., vascular coupler 125) and herein may be made from a variety of materials. For example, the petals may be made of a superelastic or shape memory metal or plastic that can be deformed during deployment to have the cross-sectional profile of the vascular coupler reduced. One example of a suitable superelastic/shape memory metal is Nitinol, a nickel and titanium alloy. Other suitable similar materials include other superelastic metal alloys, including spring stainless steel 17-7 PH, other spring metal alloys such as Elgiloy™, Inconel™, platinum-tungsten alloy, and superelastic polymers. The securing members may be made from the same or different materials as the petals.

The overmolded stem, ridges, and hemostatic gasket may be partially or completely fabricated from many different types of synthetic biocompatible materials, including silicone, polyurethane, polytetrafluoroethylene (PTFE), expanded polytetrafluoroethylene (ePTFE), polyester, Dacron™, Mylar™, polyethylene, PET (Polyethylene terephthalate), polyamide, polyamide, PVC, Kevlar™ (polyaramid), polyetheretherketone (PEEK), polypropylene, polyisoprene, polyolefin, or a composite of these or other suitable materials. Some polymer materials could be irradiated in a desired geometry, for the shape to be "set" into that position. A similar process using heat instead of radiation could be used where the thermoplastic polymer is annealed (and cooled) into a particular shape and geometry.

The stem, ridges, and hemostatic gasket also can be partially or completely made from many different types of biodegradable/bioabsorbable materials, including modified starches, gelatins, cellulose, collagen, fibrin, fibrinogen, elastin or other connective proteins or natural materials, polymers or copolymers such as polylactide [poly-L-lactide (PLLA), poly-D-lactide (PDLA)], polyglycolide, polydioxanone, polycaprolactone, polygluconate, polylactic acid (PLA), polylactic acid-polyethylene oxide copolymers, poly (hydroxybutyrate), polyanhydride, polyphosphoester, poly (amino acids), poly(alpha-hydroxy acid) or related copolymers of these materials, as well as composites and combinations thereof and combinations of other biodegradable/bioabsorbable materials.

Additionally, the stem, ridges, and hemostatic gasket can be partially or completely fabricated from materials that swell or expand when they are exposed to a fluid (such as blood, another body fluid, or an infused fluid). These materials include hydrophilic gels (hydrogels), foams, gelatins, regenerated cellulose, polyethylene vinyl acetate (PEVA), as well as composites and combinations thereof and combinations of other biocompatible swellable or expandable materials.

The stem, securing members, hemostatic gasket, and petals can be configured to have increased biocompatibility and/or blood compatibility, such as by having a textured surface that promotes endothelial cell growth and adhesion.

Figure 7A:
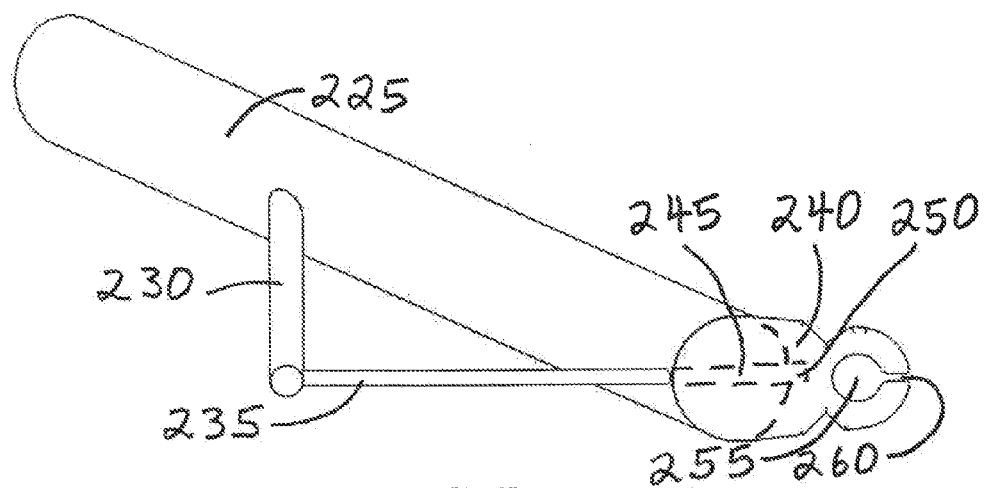
FIGS. 7a and 7b are perspective bottom and front views of a deployment tool for deploying vascular couplers.
Figure 7B:
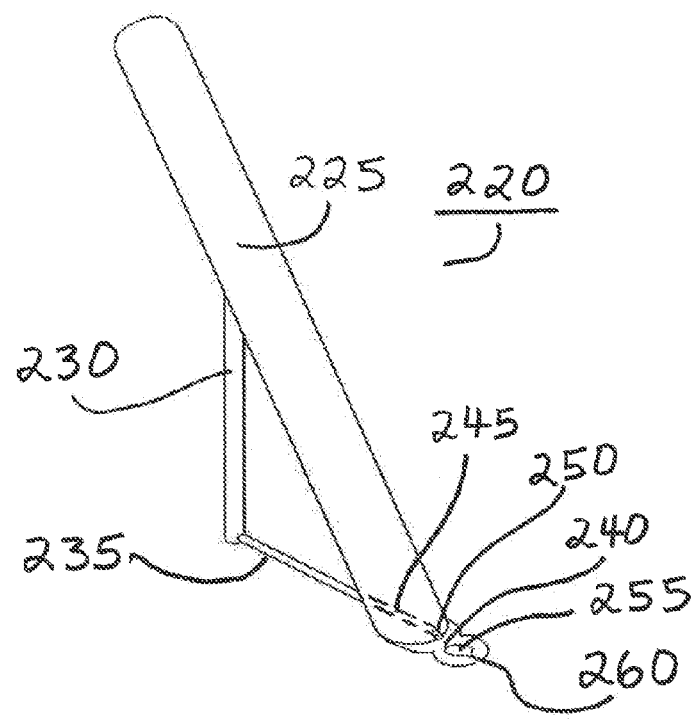
Figure 7C:
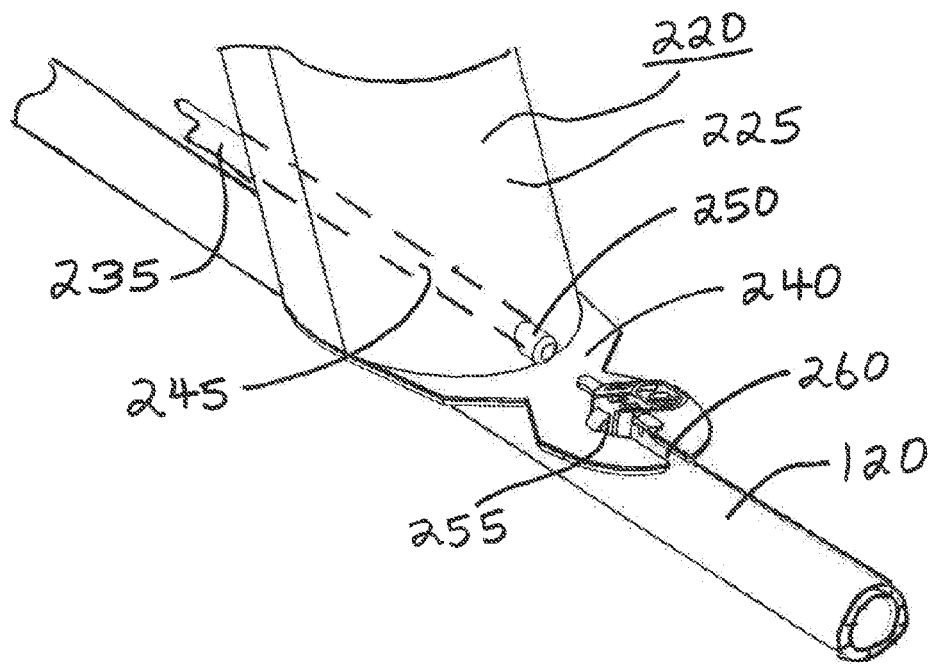
FIG. 7c is an enlarged perspective front view of the deployment tool of FIG. 7a with a mounted vascular coupler.

Referring to FIGS. 7a–7c, a deployment tool 220 can be used to deploy the vascular coupler 125 into an opening 265 in a vessel 120. As briefly described above, the petals 140 can be moved into a deflected position in which they extend distally from the stem 130. In such a configuration, the profile of the coupler 125 is reduced, which eases the implantation of the coupler through the opening 265 in a blood vessel and reduces the necessary diameter of the opening 265 into the vessel 120. The deployment tool 220 includes a handle 225, a first rod 230, a second rod 235, and a plate 240. The first rod 230 is pivotally mounted to the handle 225, the second rod 235 is mounted to the first rod and extends through a channel 245 in the handle 225. The second rod 235 includes a pushing end 250 that extend from the channel 245 above the plate 240. The plate 240 includes an opening 255 that is connected to a slot 260. The opening 255 is configured to receive the vascular coupler 125 (FIG. 7c) and the second rod 235 is configured to be advanced in the channel 245 to push the coupler from the opening 255 through the slot 260 to release the deployment tool 220 from the coupler. The petals 140 of coupler 125, or the analogous petals of a different coupler, as illustrated in FIG. 7c, are deflected forward in the distally extending position by opening 255. The notches in the plate 240 function as hinges to assist in the release the coupler from the opening 255. Removing the coupler from the opening deforms the plate 240. As such, the deployment tool 220 is likely to be a single use device. The notched deployment tool 220 can be fabricated without the first rod and second rod used to push the coupler from the tool.

Referring also to FIG. 7d, after placing the extended petals 140 through the opening 265, the second rod 235 is advanced to push the coupler from the opening 255 and through the slot 260. The petals 140 then will be released from the constraining force after the coupler is dislodged from the slot. When the constraining force is removed, the petals will expand outwardly and trap the vessel wall 270 in the space 210 between the ridges 135 and the petals 140. If, for example, the opening 265 is formed too large and there is play between the opening and the stem 130, the hemostatic gasket 205 will reduce the likelihood that blood will leak from the vessel 120 through the opening.

Figure 8A:
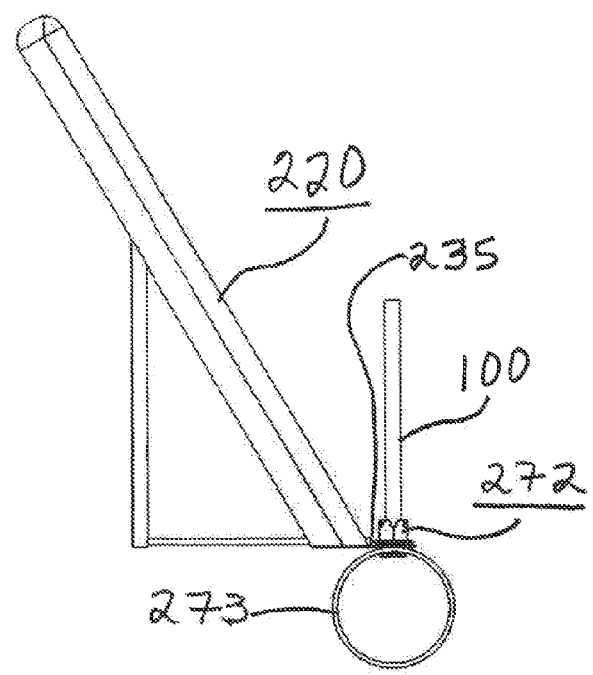
FIG. 8a is side view of a second deployment tool for deploying vascular couplers.
Figure 8B:
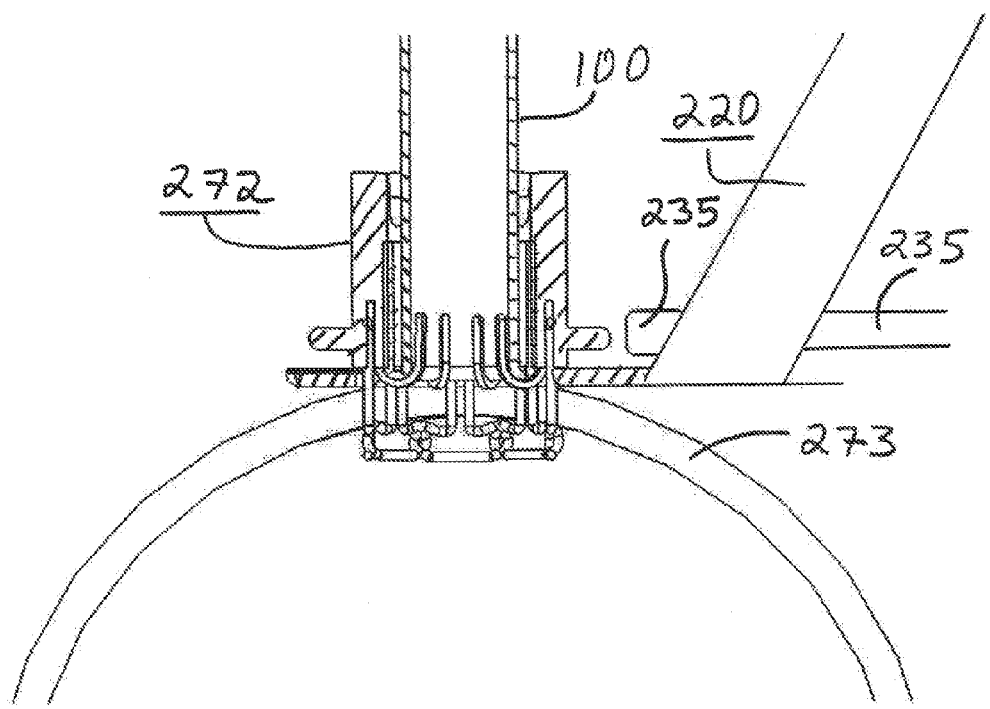
FIG. 8b is an enlarged cross-sectional side view of the second deployment tool deploying a vascular coupler.

Referring to FIGS. 8a and 8b, similar to the vascular coupler 125 being deployed in a coronary artery, a vascular coupler 272 can be deployed into an aorta 273 using the deployment tool 220 and the second rod 235 advanced to deploy the coupler 272 into position.

Figure 9A:
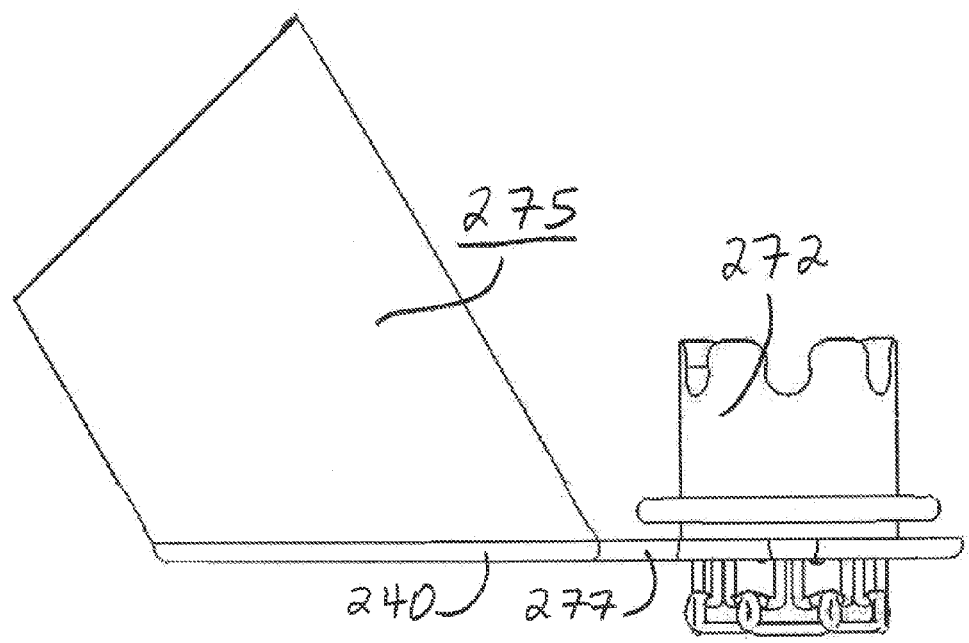
FIGS. 9a and 9b are side and perspective side views of a third deployment tool for deploying vascular couplers.
Figure 9B:
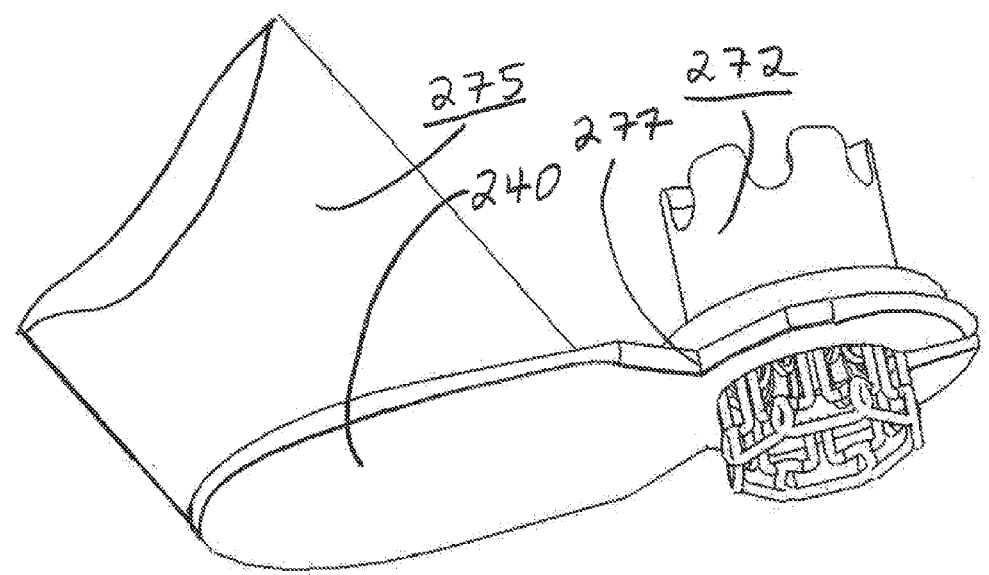

Referring to FIGS. 9a and 9b, a deployment tool 275 can be configured similarly to the deployment tool 220 except that the rods used to deploy the coupler 272 are not present. Using this deployment tool 275, the coupler is removed by the surgeon who relies on one or more weakened sections 277 in the plate 240 to cause the slot 260 to enlarge in width by holding the coupler in position while pulling back on the deployment tool 275. One of several advantages of the deployment tool 275 is its simplicity of manufacture and use. This leads to a potential low cost and single use status.

Figure 10A:
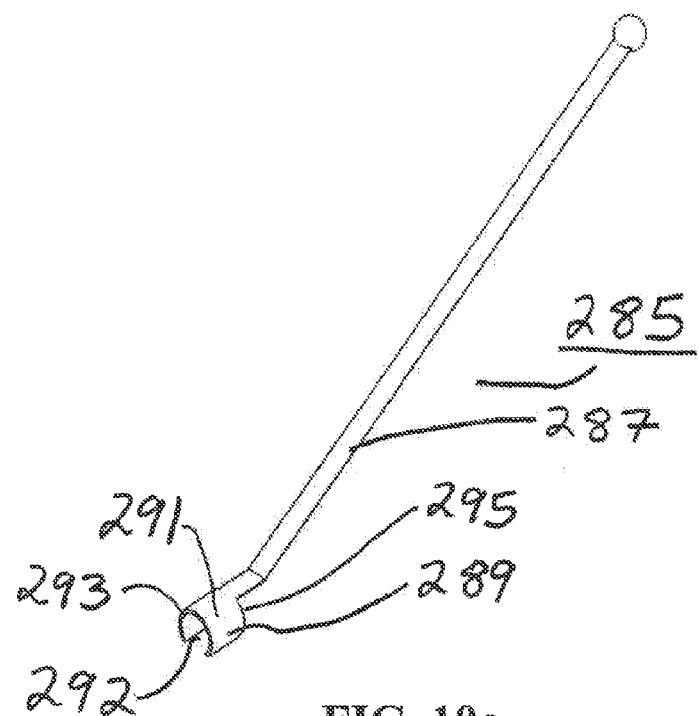
FIG. 10a is a perspective front view of a graft deployment tool for placing a graft in a vascular coupler.
Figure 10B:
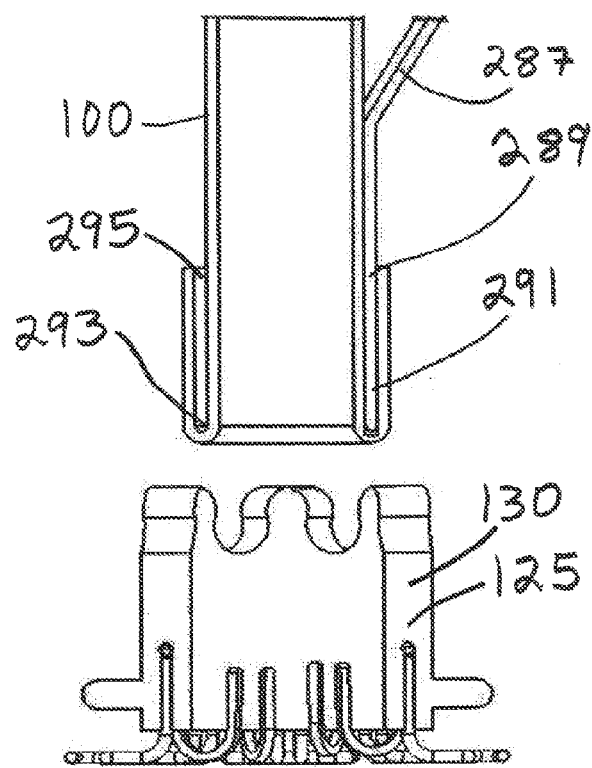
FIGS. 10b and 10c are cross-sectional side views of the graft deployment tool placing a graft in a vascular coupler.
Figure 10C:
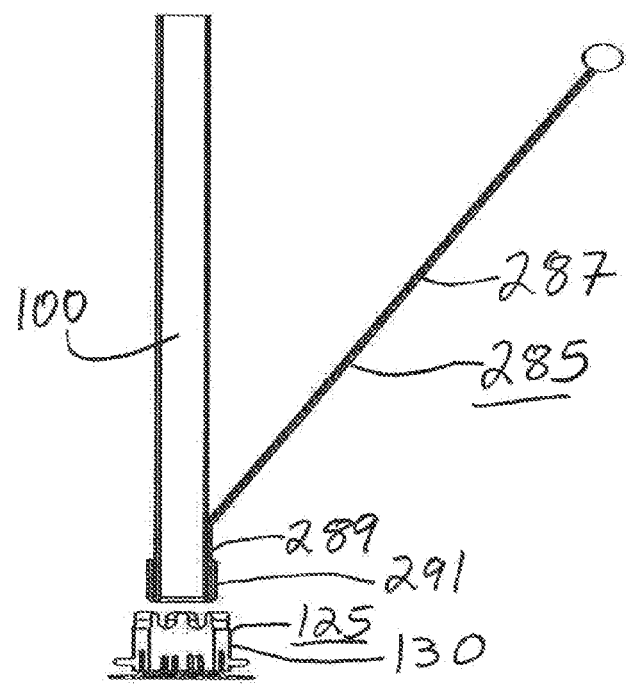
Figure 11:
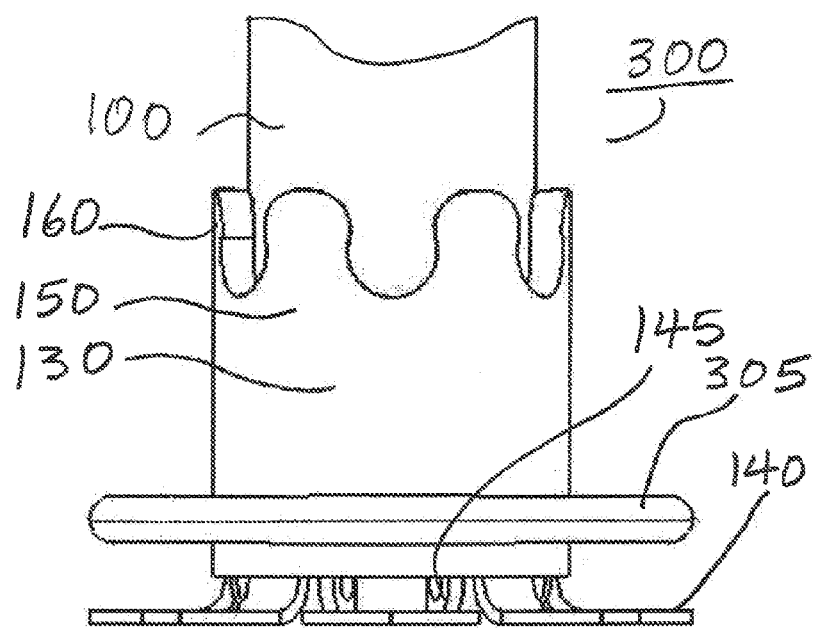
FIGS. 11–13 are front, cross-sectional side, and bottom views of a vascular coupler.

Referring to FIGS. 10a–10c, a related tool that has some similarities to the deployment tools is a vessel loading tool 285. The vessel loading tool 285 includes a handle 287 and a retaining member 289. The retaining member 289 extends from the distal end of the handle 287 and includes a partially or completely circumferential wall 291 that defines a lumen 292 and has a leading edge 293 and a trailing edge 295. The vessel 100 is mounted to the retaining member 289 by passing it through the lumen 292 and then everting the distal end of the vessel around the leading edge 293 of the retaining member. The vessel 100 can be everted and pulled back over the retaining member to the extent that it extends beyond the trailing edge 295. After the vessel 100 is mounted to the retaining member 289, the physician uses the handle 287 to advance the retaining member and vessel into the vascular coupler 125 between the securing members 145 and the stem 130. The securing members 145 then are closed down upon the vessel 100 and the vessel loading tool 285 is withdrawn, leaving the vessel in place within the vascular coupler 125.

Figure 12:
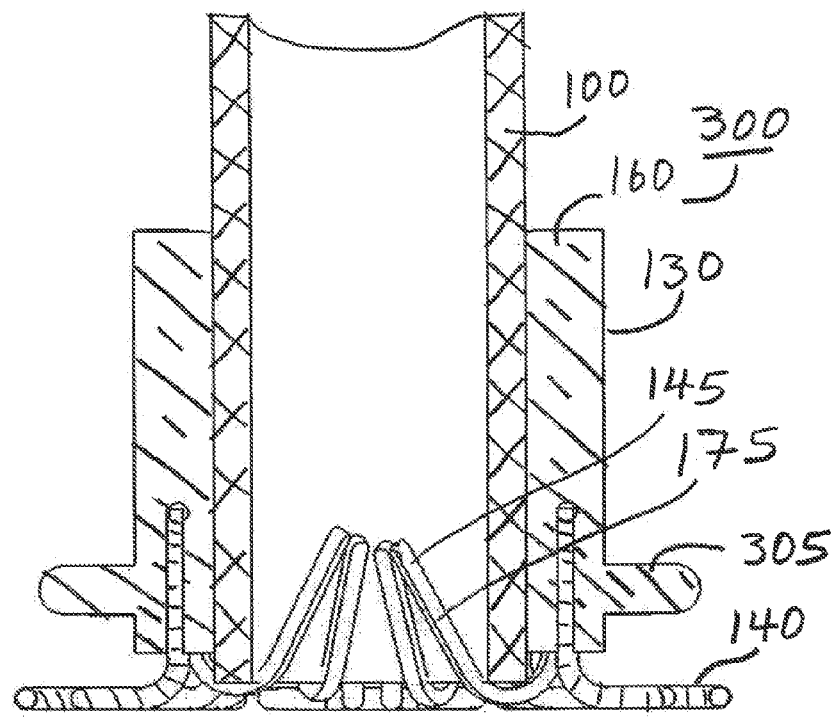
Figure 13:
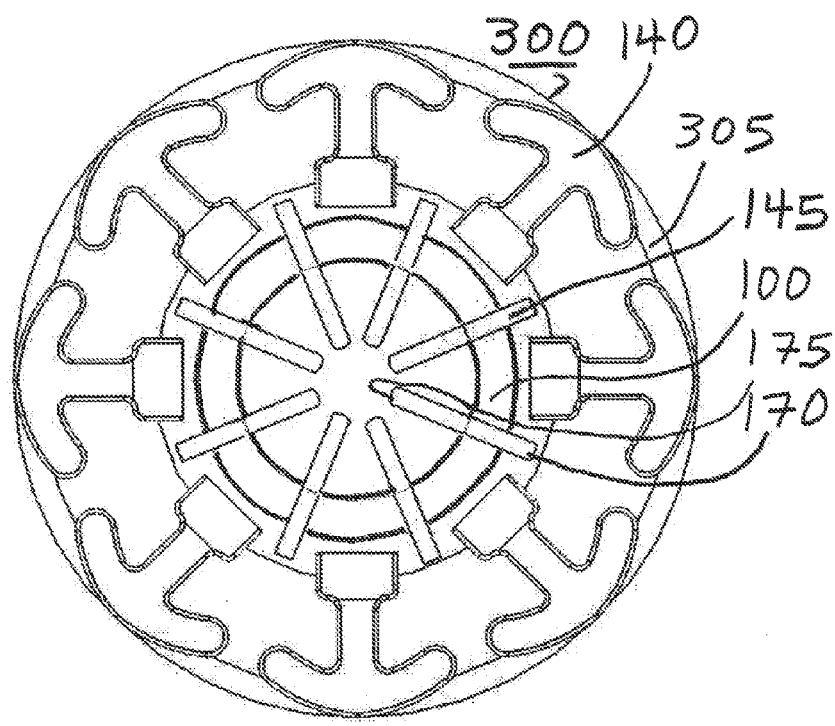
Figure 14:
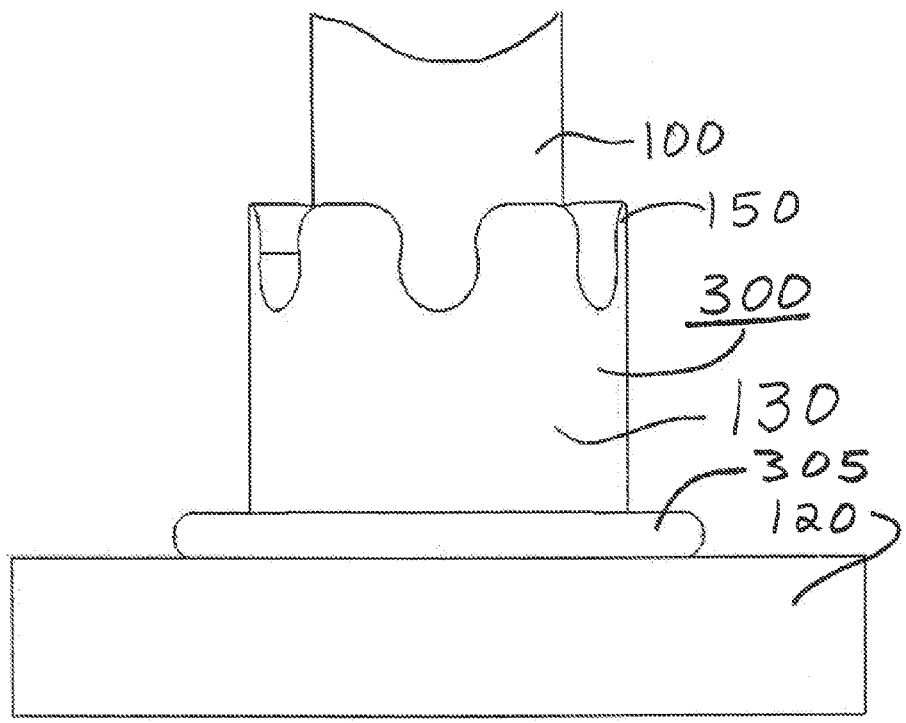
FIG. 14 is a side view of the coupler of FIG. 11 implanted in a vessel.

Of course, numerous variations of the vascular coupler 125 are within the scope of this patent. For example, referring to FIGS. 11–14, a vascular coupler 300 includes the stem 130, the petals 140, the securing members 145, and a ridge 305. In contrast to the vascular coupler 125, the vascular coupler 300 has a single ridge 305 and embedded securing members 145. The embedded securing members 145 are overmolded when the petals 140 are overmolded such that the outer arms 170 are embedded within the stem 130, although the inner arms 175 extend from either the distal end 155 of the stem or the inner lumen 165 of the coupler. This reduces the complexity of the procedure for the physician because the securing members 145 will not accidentally be dropped when mounting the graft 100 to the coupler 300. FIG. 12 illustrates the securing members 145 in the position with a large gap and the graft 100 positioned within the coupler prior to securement. FIG. 13, in contrast, illustrates the securing members 145 deformed or released into the position with the small gap and the graft 100 therefore securely positioned within the coupler. FIG. 14 illustrates the coupler 300 mounted to the vessel 120 such that the single ridge 305 is secured against the outer surface of the vessel. Although FIGS. 11–14 show the coupler without the hemostatic gasket 205, the gasket optionally can be included on this coupler.

Because the securing members 145 are integrally mounted to the coupler, there is no need to have multiple ridges 135 that are spaced apart around the circumference of the coupler as are necessary to place the securing members 145 to the coupler. Instead, a single ridge 305 can be overmolded and the single ridge configured to encircle the entire circumference of the coupler. However, the single ridge 305 can be configured to encircle less than the entire circumference of the coupler such that the coupler can be curled within itself, as described in greater detail below.

Figure 15:
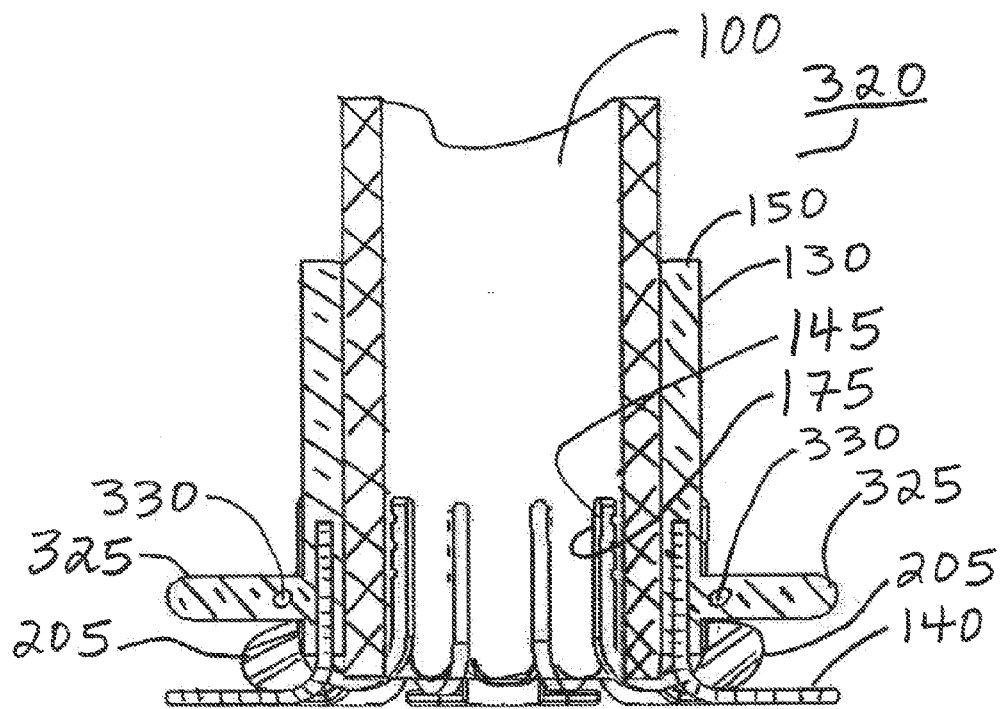
FIG. 15 is a cross-sectional side view of a vascular coupler having a reinforcing ring and an enlarged hemostatic gasket.

Referring to FIG. 15, a vascular coupler 320 includes the stem 130, petals 140, embedded securing members 145, a single ridge 325, and a hemostatic gasket 205. The vascular coupler 320 is similar to the vascular coupler 300, except that the coupler 320 additionally includes the hemostatic gasket 205 and a reinforcing ring 330. The reinforcing ring is an elastic ring made of, for example, metal or plastic, that provides reinforcing circumferential hoop strength to the coupler. The reinforcing ring 330 can encircle the entire circumference as a closed ring, the entire circumference as a ring with two adjacent or non-joined ends, or as a ring that leaves a gap. A pair of adjacent or non-joined ends allows some elastic expansion without providing any restraining force to the coupler ballooning open. Although the reinforcing ring is illustrated as being a rod having a round cross-sectional shape, actual circumferential shape of the ring can be varied greatly, as can the basic material (i.e., a rod). For example, a sinusoidal, rectangular-shaped band or sheet can be used in place of the rod.

Figure 16:
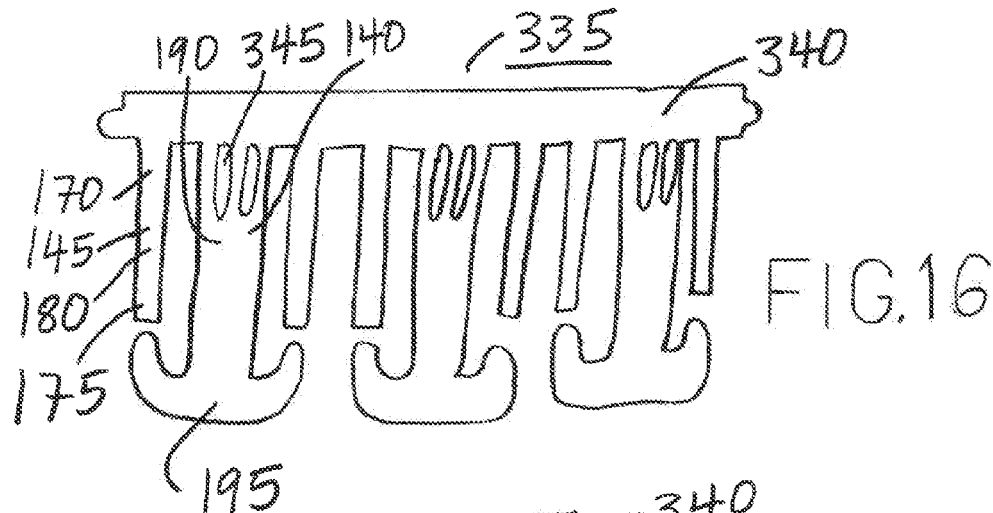
FIGS. 16–18 are side, end, and top views of the components used to fabricate the petals and securing members of a vascular coupler.
Figure 17:
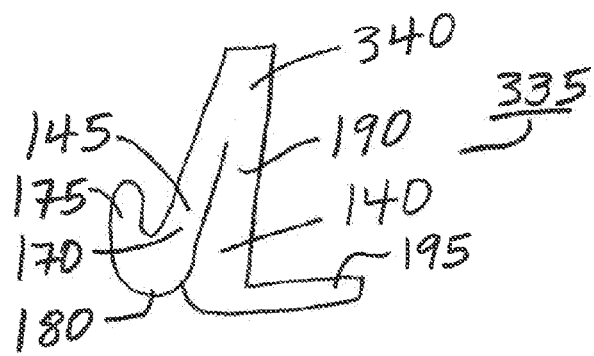
Figure 18:
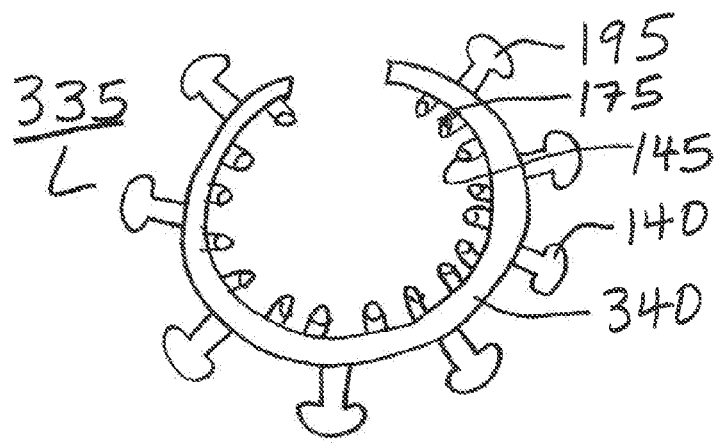

Referring to FIGS. 16–18, the petals 140 and the securing members 145 can be fabricated as a single piece by etching or otherwise machining a single sheet 335 of starting material. As illustrated in FIG. 16, the petals 140 and are securing members 145 are etched such that they extend from a common edge 340. For example, the petals 140 are etched with the first arm 190 and the second arm 195 in a common plane. Openings or grooves 345 also can be etched in the first arms 190 to provide increased bonding strength during overmolding. The securing members 145 likewise are etched with the outer arm 170, the inner arm 175, and the connecting portion 180 in a common plane. As illustrated in FIG. 17, however, after bending the securing members' inner arms 175 extend inward and the petals' second arms 195 extend outward. Then as illustrated in FIG. 18, by bending the common edge 340 to form a partially or completely closed loop, the petals 140 extend outward and the securing members extend inward. This part 335 then can be overmolded to form a coupler with embedded securing members.

Figure 19:
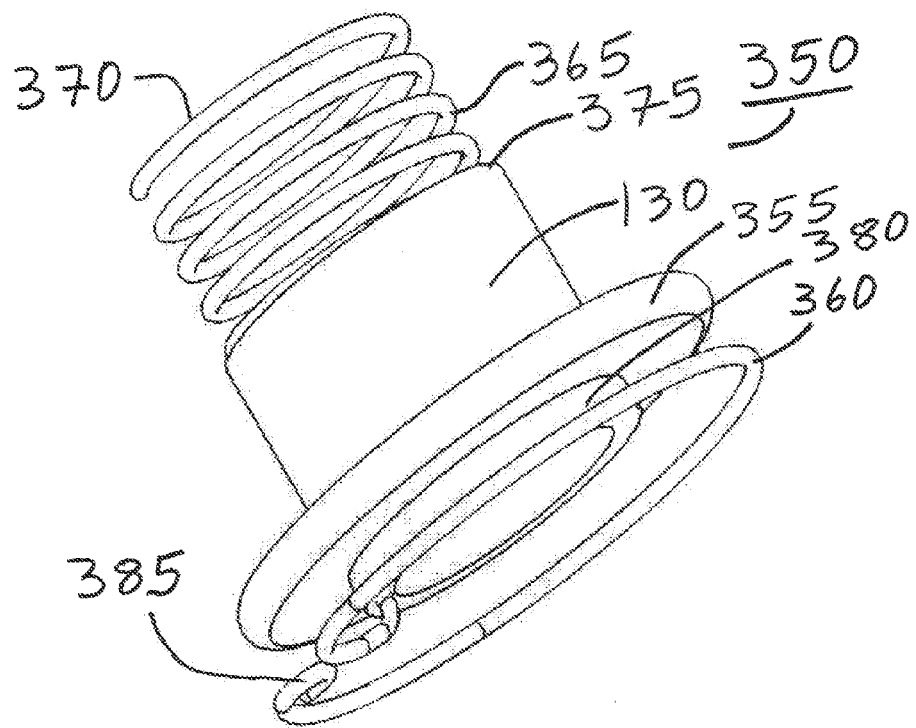
FIGS. 19–21 are perspective front, cross-sectional side, and bottom views of a vascular coupler having a wire petal.
Figure 20:
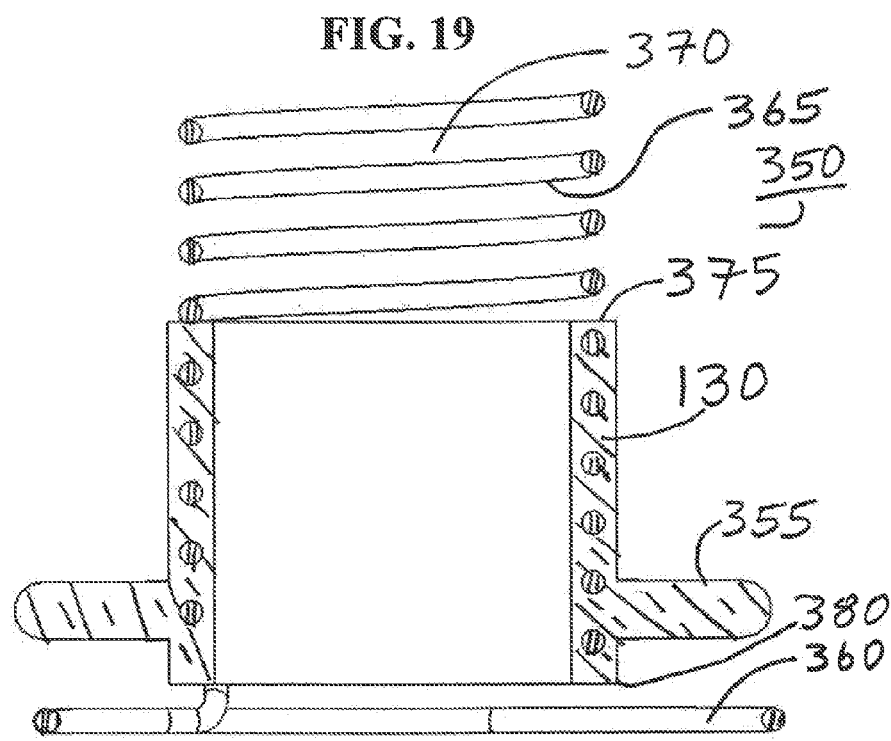
Figure 21:
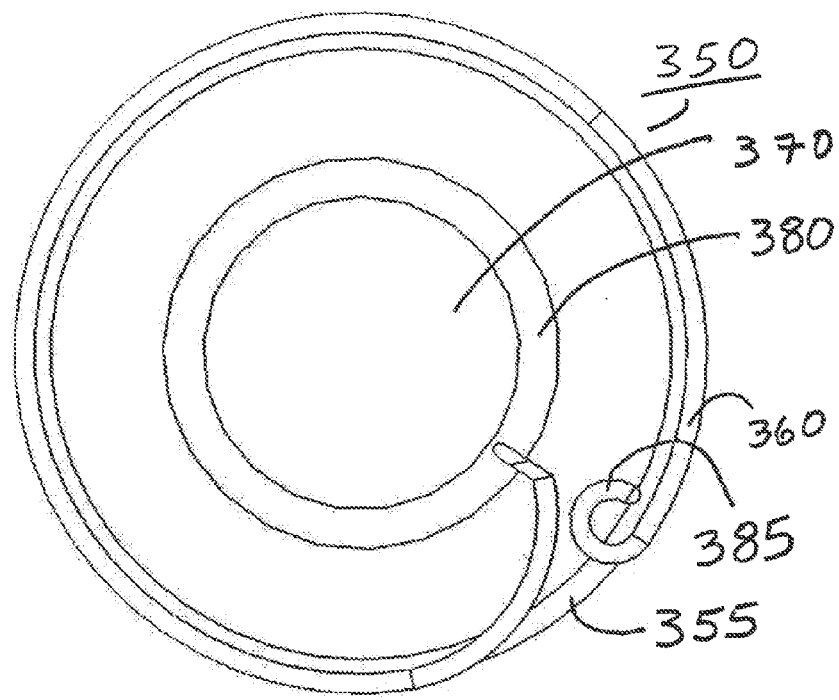

Referring to FIGS. 19–21, a vascular coupler 350 includes a stem 130, a ridge 355, a petal 360, and a strain relief 365. A lumen 370 passes through the strain relief 365 and the stem 130. The strain relief 365 is a coiled (e.g., coiled wire or spring) that is embedded within the stem 130 and extends from a proximal end 375 of the stem. The petal 360 is an extension of the strain relief and extends from a distal end 380 of the stem. As evident from FIGS. 19–21, the stain relief 365 and the petal 360 are of a different diameter, and can be of a different pitch as well. The petal 360 includes a curled distal end 385 that is configured to prevent puncturing of the receiving vessel 120 when the coupler 350 is implanted. The coupler 350 is fabricated, for example, by overmolding. The strain relief 365 and petal 360 are formed initially, placed in a mold, and the stem 130 and ridge 355 formed by overmolding with a compliant material, as described above.

Although FIGS. 19–21 do not show the securing members 145 and the bypass vessel 100, they are incorporated in any manner described herein. For example, the outer arms 170 of the securing members can be embedded within the stem and then the inner arms 175 extend into the lumen 370. Alternatively, the securing members 145 can be loose, the ridge 355 replaced with multiple, separated ridges, and the securing members positioned between the ridges and used to clip the vessel 100 to the coupler. The strain relief 365 therefore surrounds the outer surface of the vessel 100. The strain relief 365 can be extended well beyond the coupler 350 and used to provide anti-kink resistance to the bypass vessel 100.

The coupler 350 is inserted into an opening in a blood vessel using one of a number of methods. For example, the coupler can be inserted using in a push-pull method. In this method, the petal is pressed against the opening in the vessel, which causes the petal to be bent in the direction of the ridge and thereby reduce the petal's diameter. The petal then slips through the opening and the physician pulls back on the coupler, if necessary, to seat it within vessel opening, between the ridge and petals. Alternatively, the petal can be pushed in at an angle such that part of the petal is within the opening and then the rest of the petal pushed in. In another alternative, the petal can be screwed in by putting part of the petal in the opening and then rotating it to place the rest of it within the opening.

Figure 22:
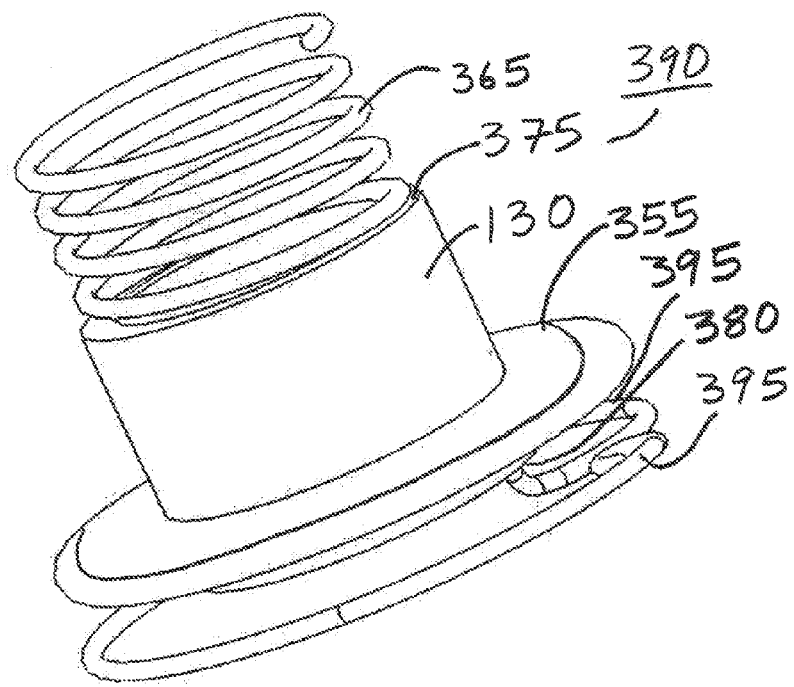
FIGS. 22–24 are perspective front, top, and bottom views of a vascular coupler having two wire petals.
Figure 23:
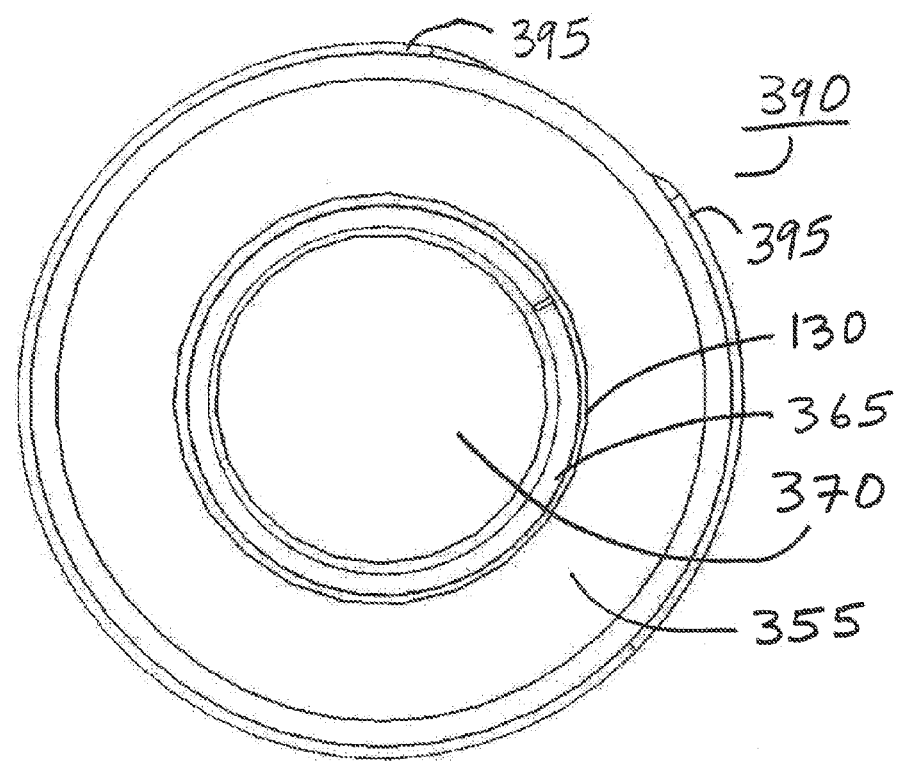
Figure 24:
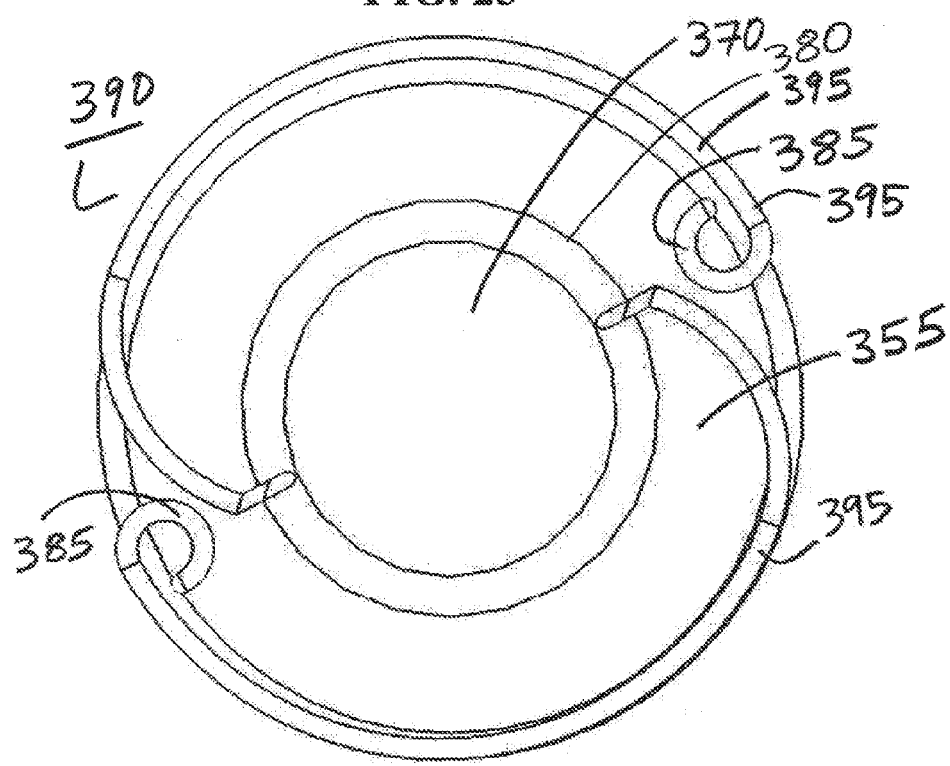

Referring to FIGS. 22–24, a vascular coupler 390 includes the stem 130, the ridge 355, the strain relief 365, and a pair of petals 395. The primary difference between the coupler 350 and the coupler 390 is the substitution of a pair of petals 395 for the single petal 360.

Figure 25:
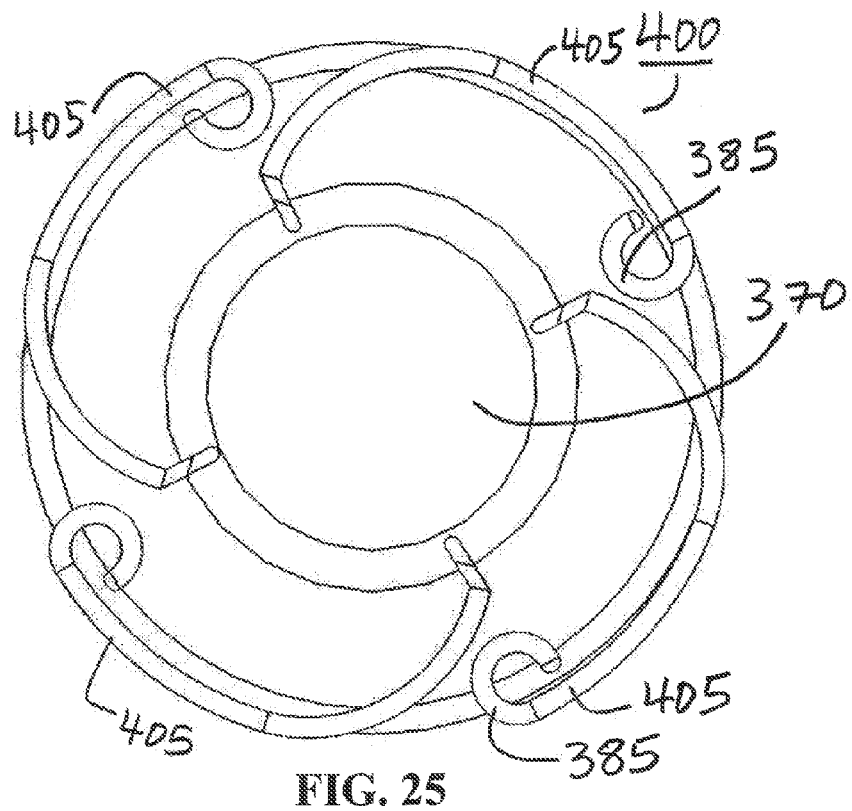
FIG. 25 is a bottom view of a vascular coupler having four wire petals.

Referring to FIG. 25, a vascular coupler 400 includes four petals 405, but otherwise is similar to the vascular couplers 350 and 390. The figures indicate that one or more petals can be used on the couplers.

Figure 26:
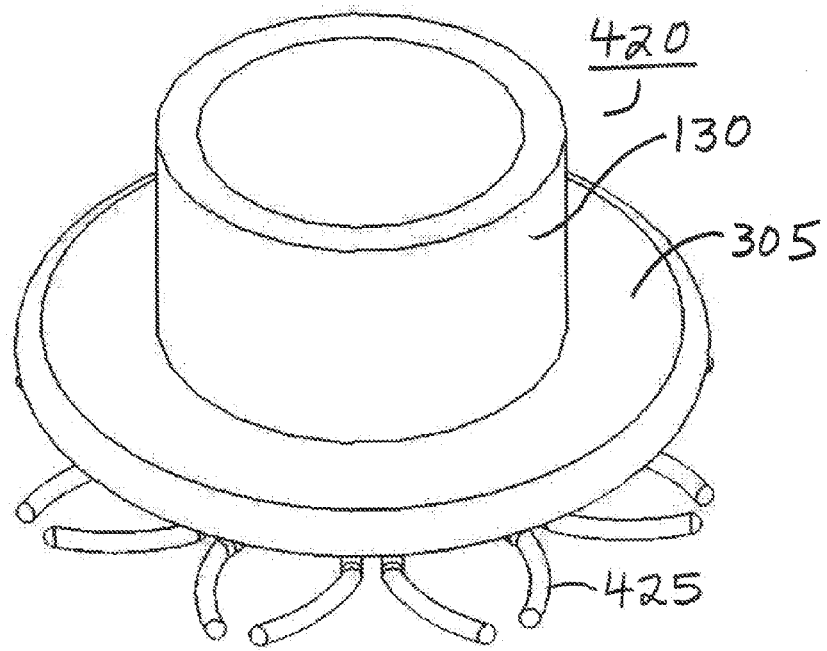
FIG. 26 is a perspective side view of a vascular coupler having wire or rod petals.
Figure 27:
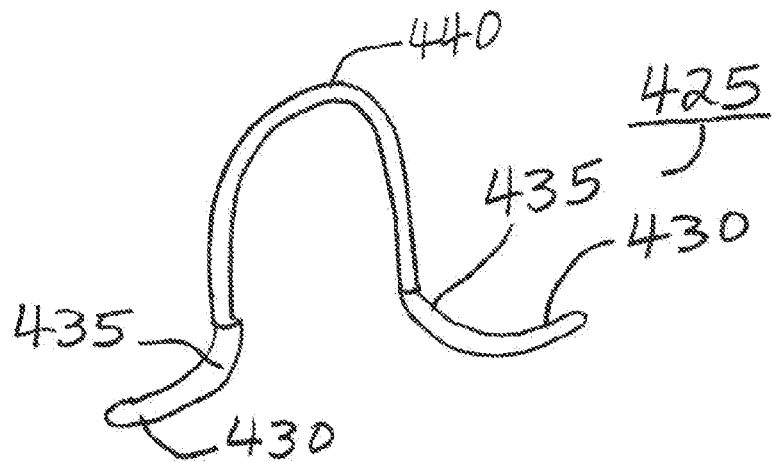
FIG. 27 is a perspective side view of the wire or rod petals.
Figure 28:
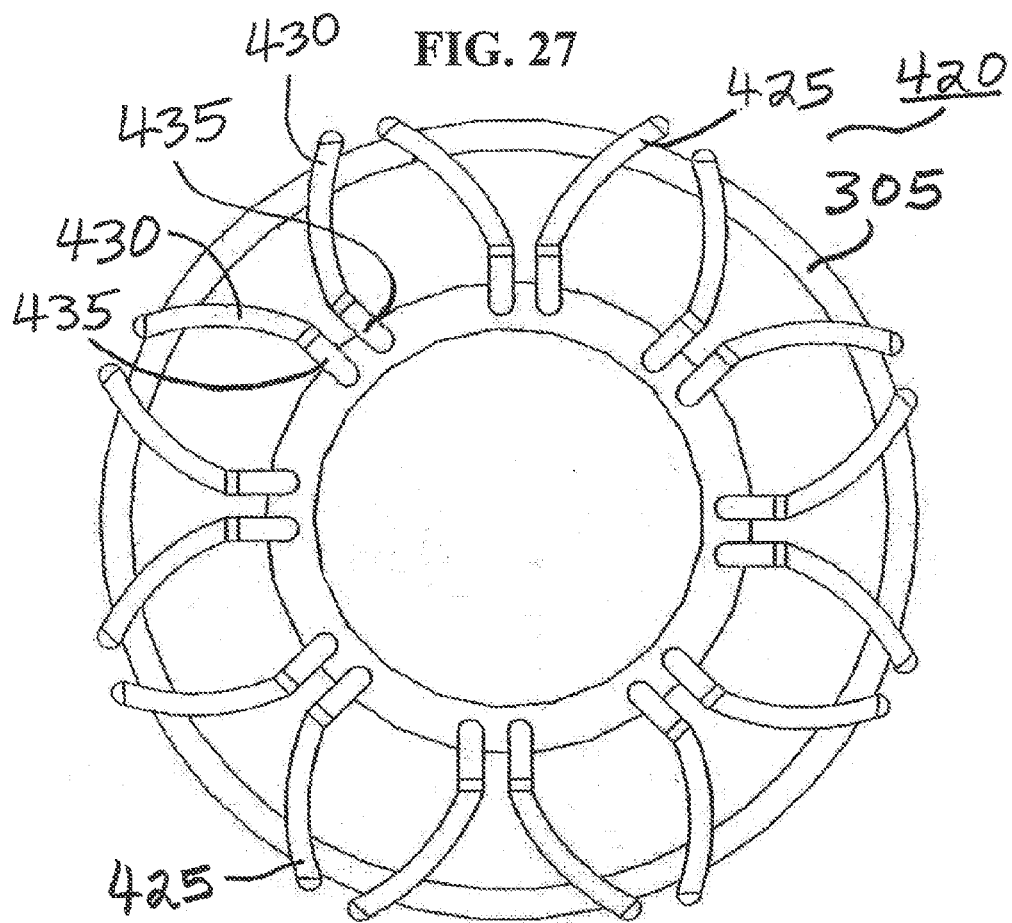
FIG. 28 is a bottom view of the vascular coupler of FIG. 26.

Referring to FIGS. 26–28, a vascular coupler 420 includes the stem 130, the ridge 305, and petals 425. The petals 425 are formed from a wire or rod and bent to have a pair of outwardly flared arms 430, a pair of parallel intermediate sections 435, and a generally U-shaped segment 440 connecting the parallel intermediate sections 435. The U-shaped segment 440 is embedded in the overmolded stem. The wire or rod petals advantageously reduce the amount of foreign material in the blood stream. Although FIGS. 26–28 illustrate an overmolded system in which the petals are overmolded when the stem is formed. However, the overmolded stem can be fabricated initially and channels left in the stem to receive the petals. This technique can be used for all of the overmolded couplers described herein. The securing members can likewise be fabricated.

Figure 29:
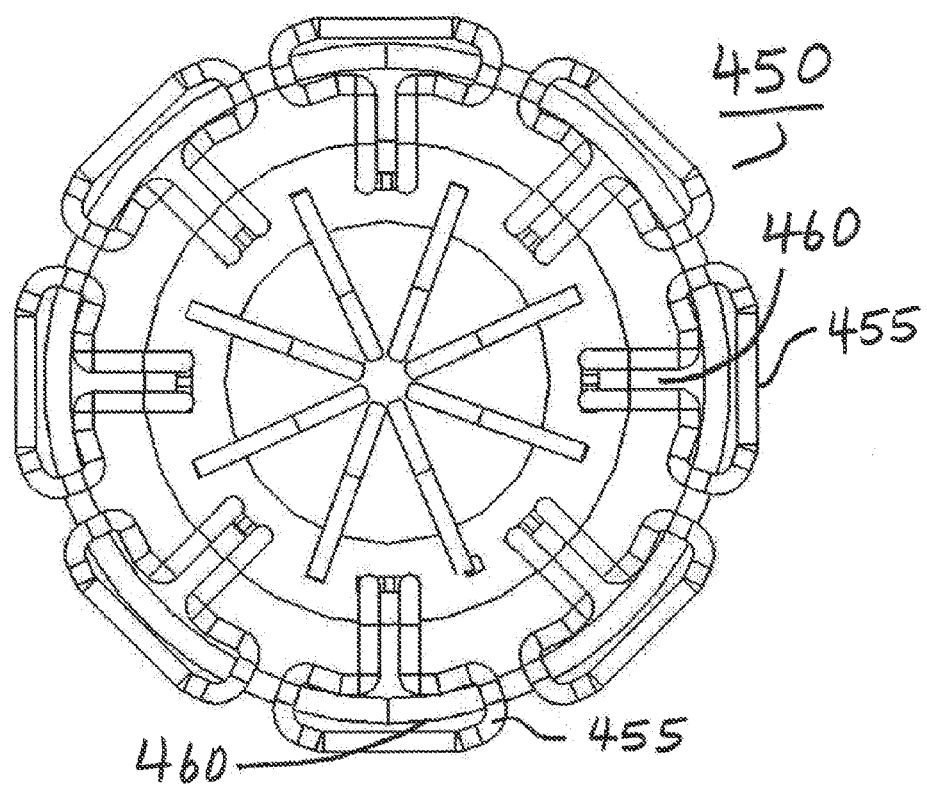
FIG. 29 is a bottom view of a vascular coupler having generally T-shaped wire or rod petals.
Figure 30:
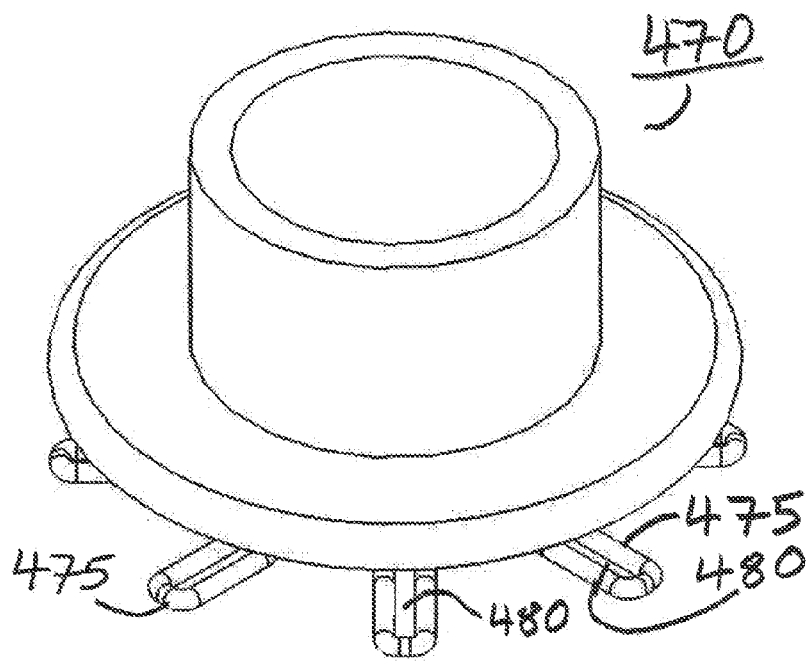
FIGS. 30 and 31 are perspective front and bottom views of a vascular coupler having U-shaped wire or rod petals.
Figure 31:
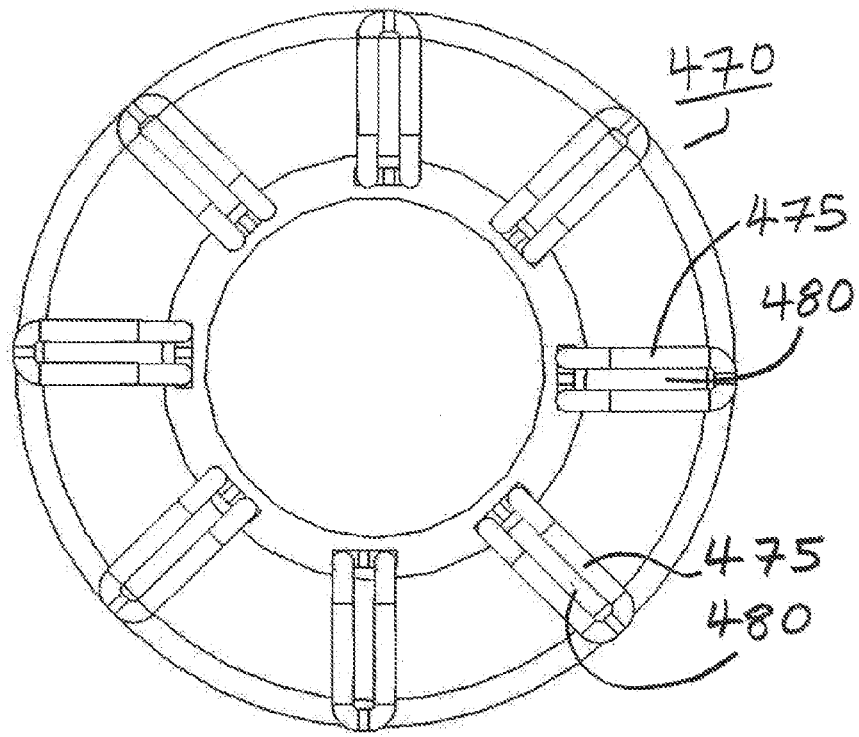
Figure 32:
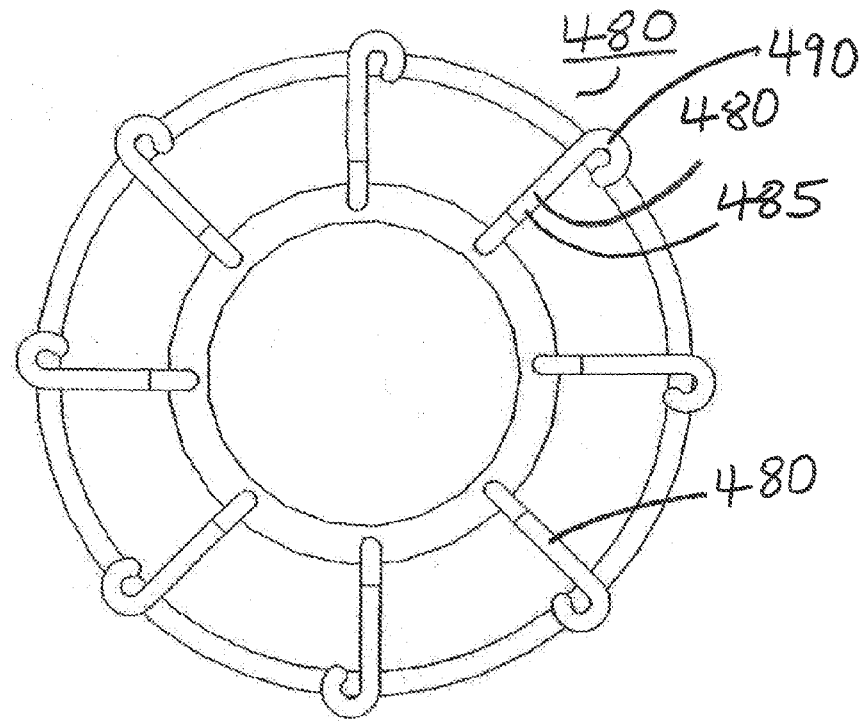
FIGS. 32–36 illustrate bottom views of vascular coupler having a variety of petal configurations.

Referring to FIG. 29, a vascular coupler 450 includes wire or rod petals 455 that are generally T-shaped. The wire or rod forms the T-shape with an open region 460 between the wire or rod. Referring to FIGS. 30 and 31, a vascular coupler 470 includes U-shaped wire or rod petals 475. The wire or rod forms the U-shape with an open region 480 between the wire or rod. Referring to FIG. 32, a vascular coupler 480 includes wire or rod petals 480, each petal includes a single arm 485 that terminates in a coiled, atraumatic tip 490.

Figure 33:
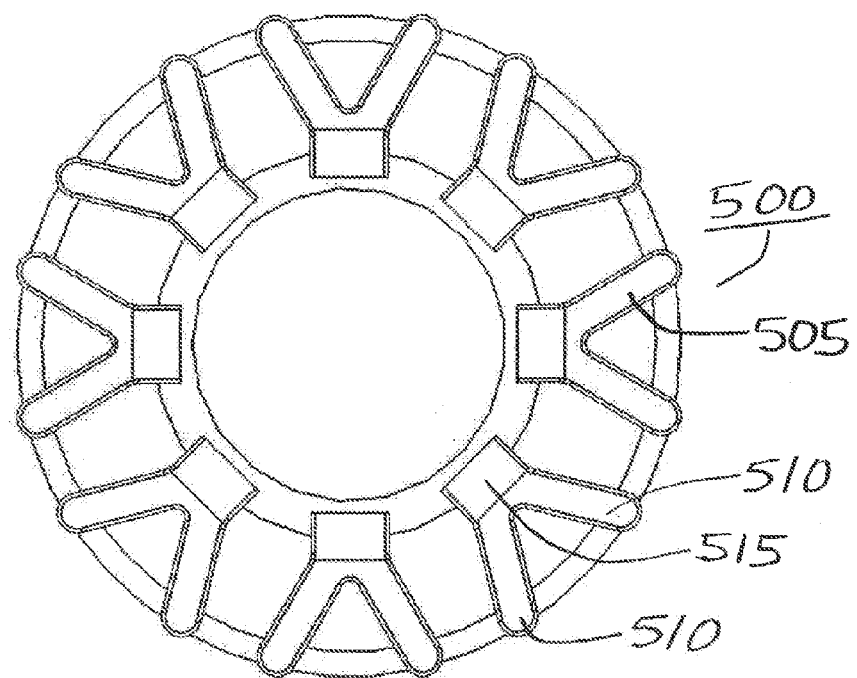
Figure 34:
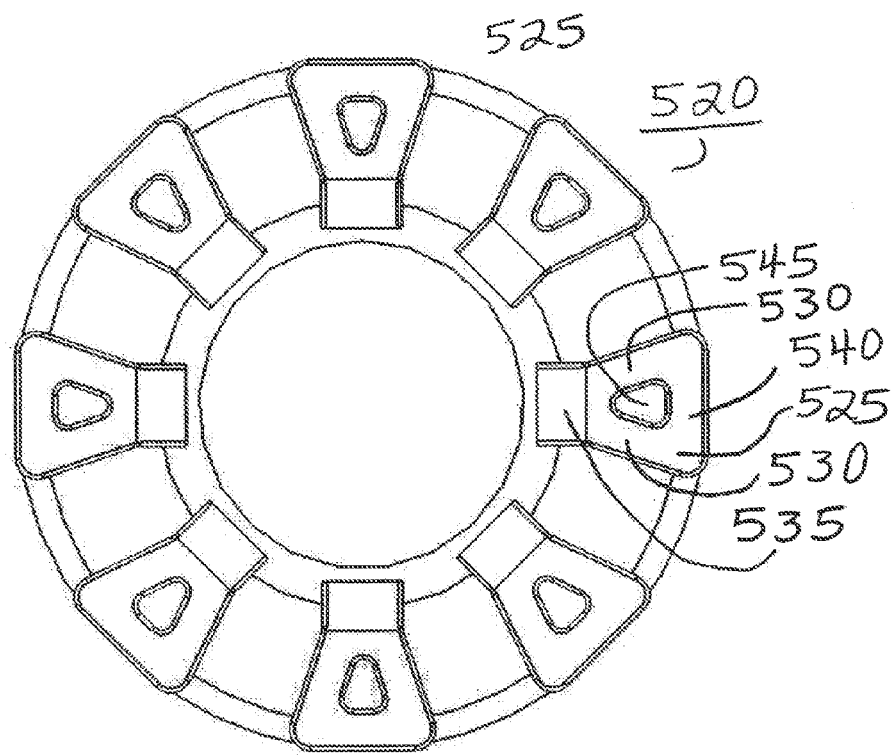
Figure 35:
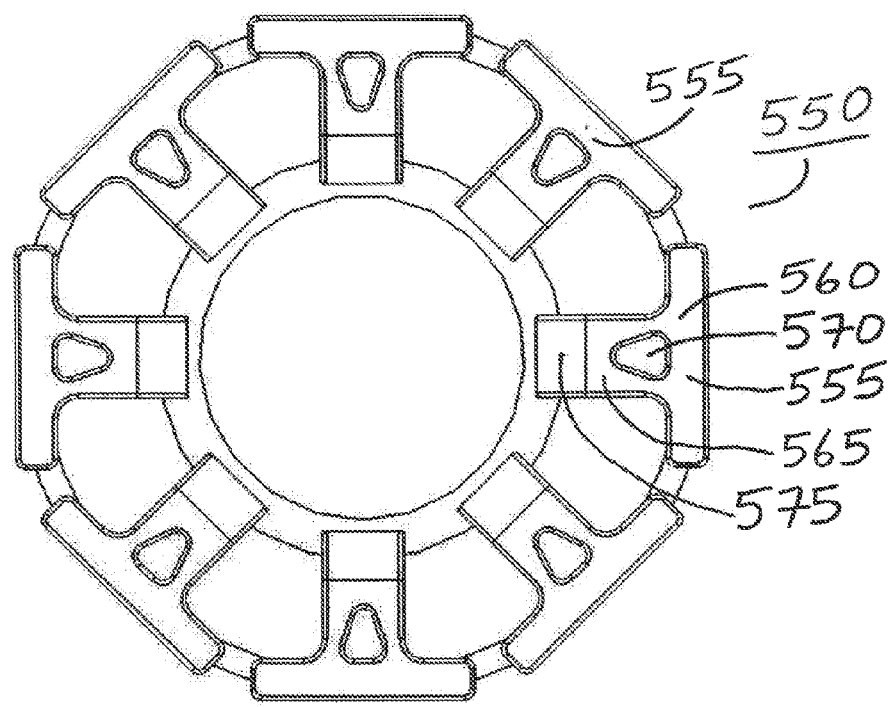

Although using wire or rod petals to minimize the amount of foreign material in the blood provides advantages, the petals may be fabricated from sheets or plates, as described above. For example, referring to FIG. 33, a vascular coupler 500 includes V-shaped petals 505 that are formed from a sheet or plate by, for example, etching. Each petal 505 includes a pair of arms 510 that are connected at a base 515. The base extends into the overmolded stem. Referring to FIG. 34, a coupler 520 includes petals 525 that are formed from a sheet or plate by, for example, etching. Each petal 525 includes a pair of arms 530 that are connected at a base 535 and at an end 540 opposite the base. The connections result in an open region 545 between the arms 530. This configuration reduces the amount of material in the blood stream and in contact with tissue while yet providing adequate pull-out resistance. Referring to FIG. 35, a coupler 550 includes petals 555 formed from sheets or plates, as described above. The petals 555 are generally T-shaped and include a pair of perpendicular arms 560 and 565 and an opening 570. The arm 565 extends from a base 575 that extends into the overmolded ridge.

Figure 36:
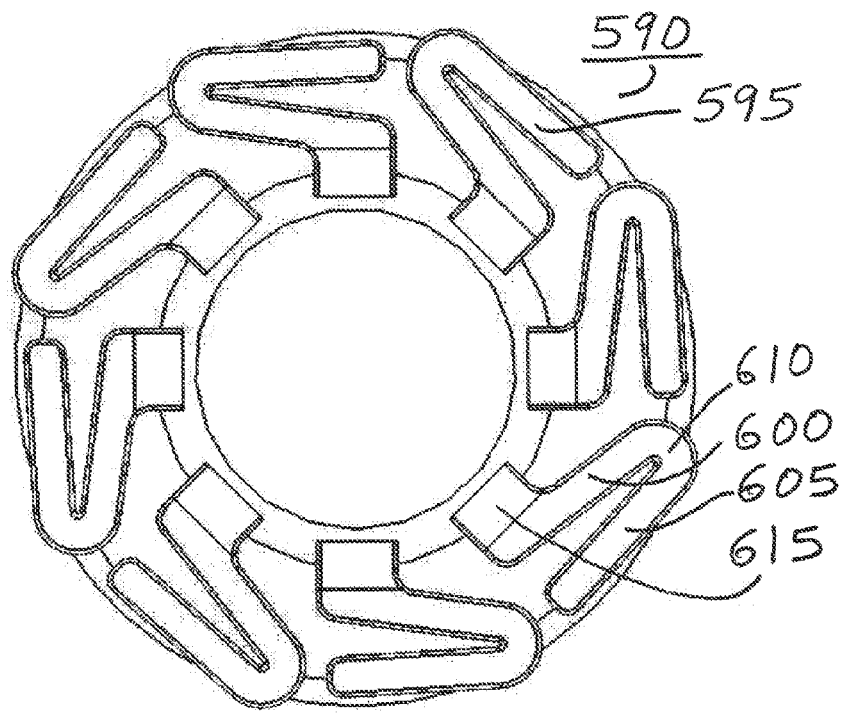

Referring to FIG. 36, a vascular coupler 590 includes partially Z-shaped petals 595. The Z-shaped petals 595 include a pair of arms 600, 605 connected at a joint 610. The arm 600 extends at an opposite end from the joint 610 from a base arm 615. The base arm 615 extends from the overmolded stem. Although the petals 595 have more material within the lumen than other versions described herein, they advantageously provide perceived and/or actual increases in the attachment of the coupler 590 to the vessel 120.

Figure 37:
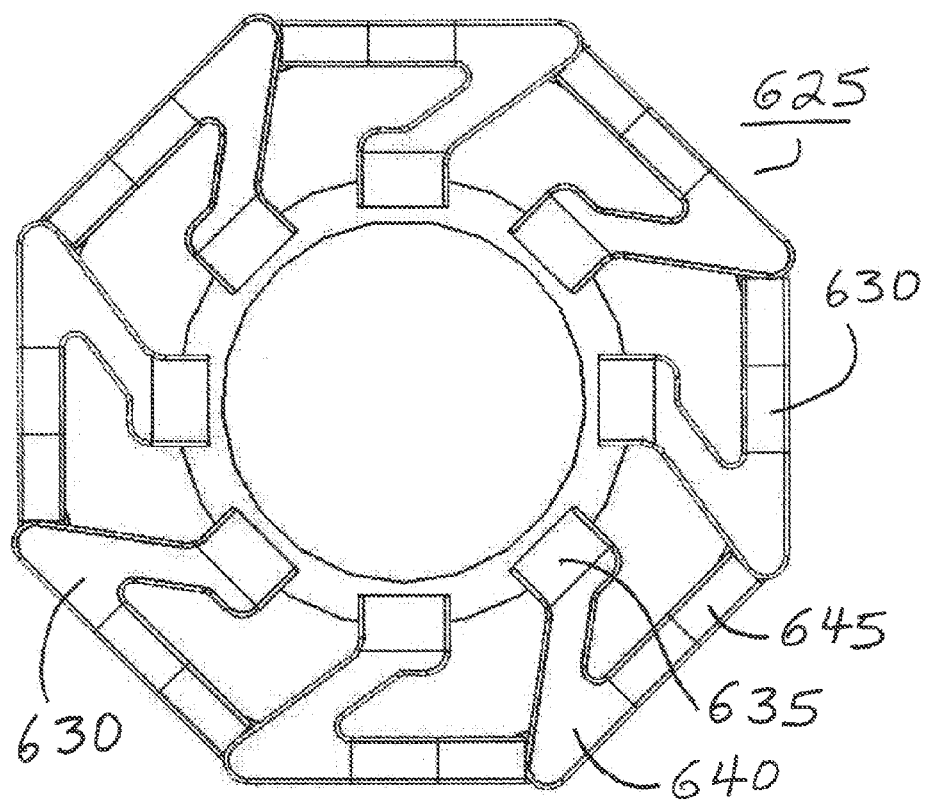
FIGS. 37 and 38 illustrate bottom and side views of a vascular coupler having overlapping petals.
Figure 38:
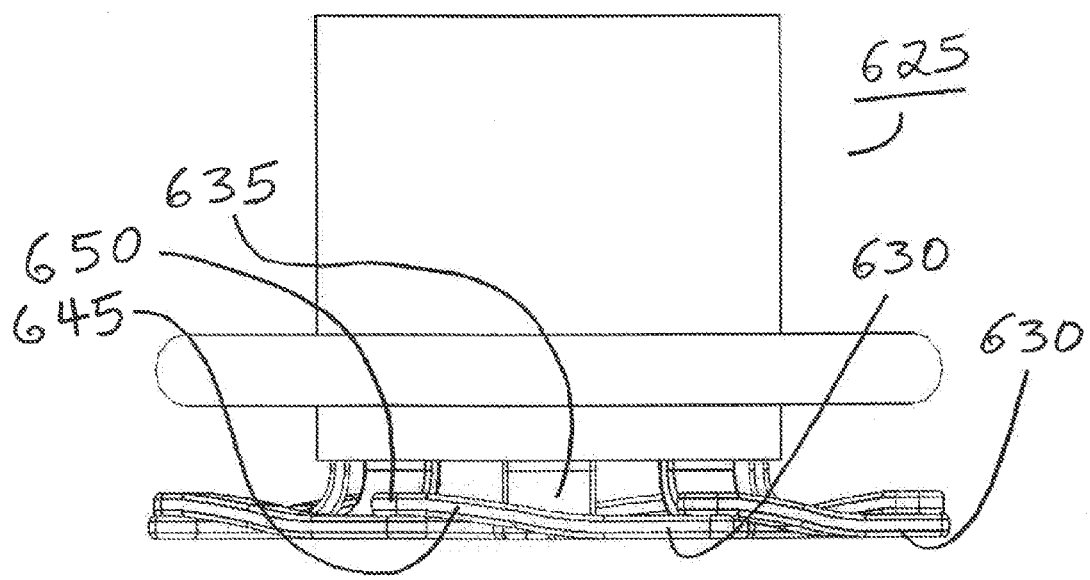
Figure 39:
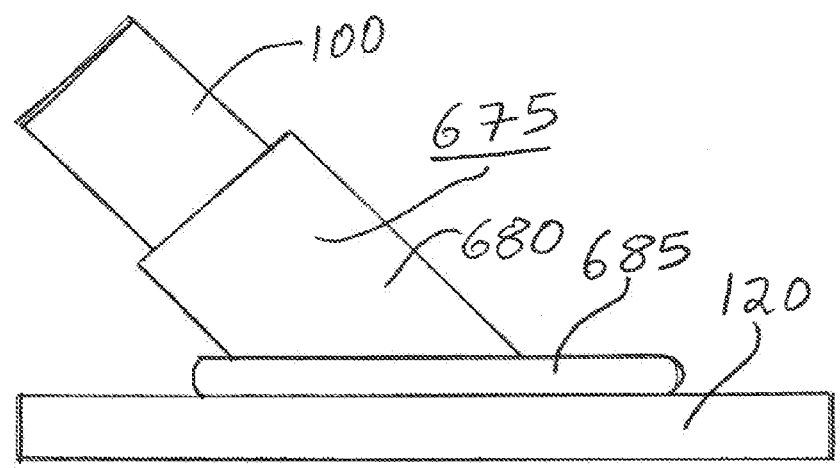
FIGS. 39–42 are side, bottom, and cross-sectional side views of vascular coupler formed at an angle of approximately 45° between the stem and the ridge.
Figure 40:
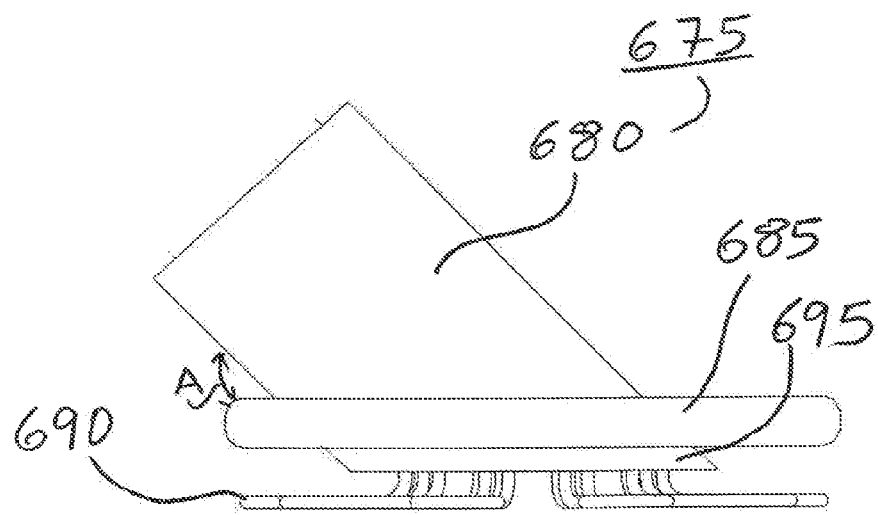
Figure 41:
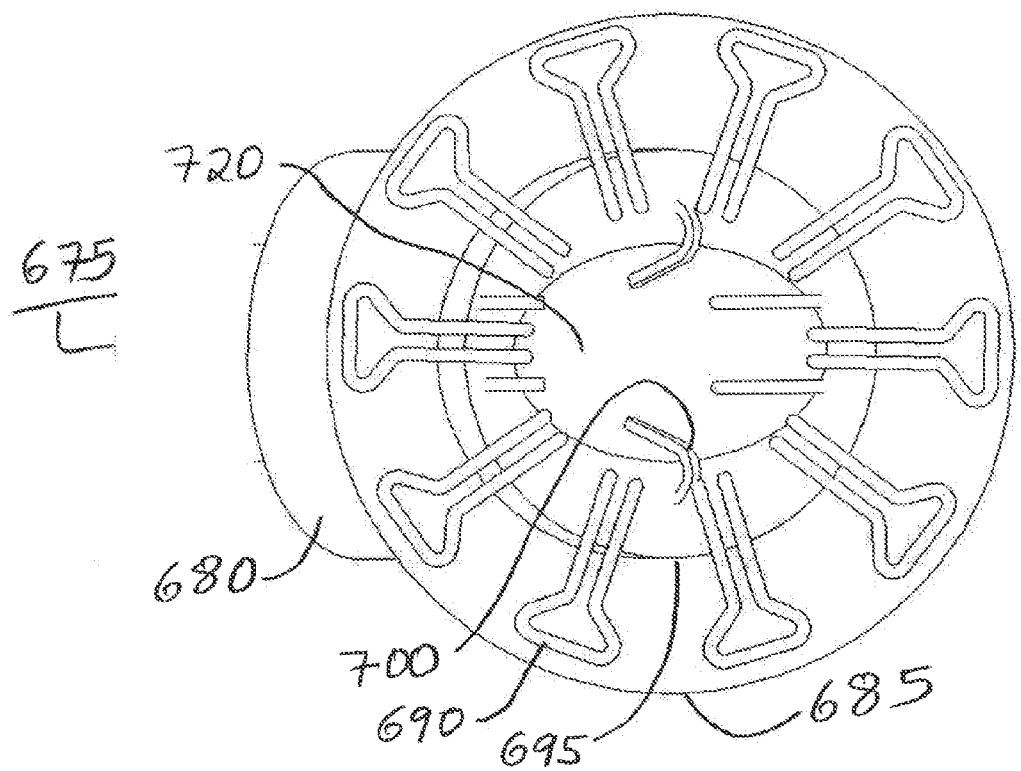

Referring to FIGS. 37 and 38, a vascular coupler 625 includes overlapping petals 630. Each petal 630 includes a base 635 that extends into the overmolded stem, a first arm 640 that extends from the base to a second arm 645. The second arm 645 includes a tip 650 that overlaps an adjacent first arm 640.

Figure 42:
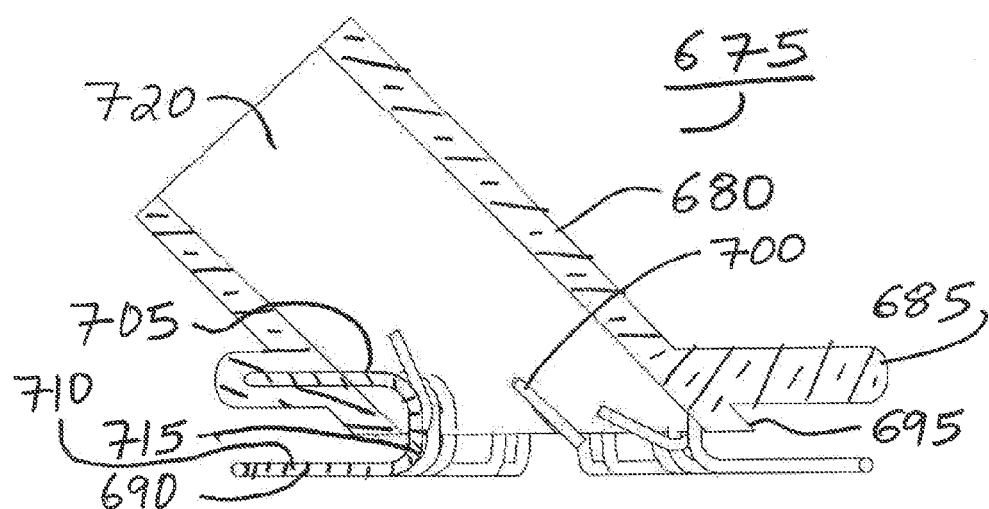

The above vascular couplers are illustrated showing a 90° angle formed between the stem and the overmolded ridge. However, other angles can be formed, based in part on the location in the body in which the coupler is to be placed. For example, referring to FIGS. 39–42, a vascular coupler 675 includes a stem 680, a ridge 685, petals 690, a hemostatic gasket 695, and securing members 700. The axis of the stem 680 forms an angle A with the plane formed by the ridge 685. The angle A is 90° in the versions illustrated above, but is shown in FIGS. 39–42 at an angle of approximately 45°. Suitable angles range between approximately 15° and 75° and, more particularly, between approximately 30° and 60°. For example, the aorta (proximal) can have an angle of approximately 45° and the coronary (distal) can have an angle of approximately 30°. Studies suggest that a 45° angle for the aorta (proximal) coupler is useful to preventing bypass graft kinking. As illustrated in FIG. 42, the petals 690 include a first arm 705, a second arm 710, and a connecting portion 715. The first arm 705 is embedded within the stem 680 and the ridge 685. Extending the first arm 705 into the ridge 685 provide additional elastic strength to the ridge 685. An additional difference between the vascular couplers above and the vascular coupler 675 is the oval cross-sectional profile of the lumen 720 of the stem 680 and the opening into the vessel 120.

Figure 43:
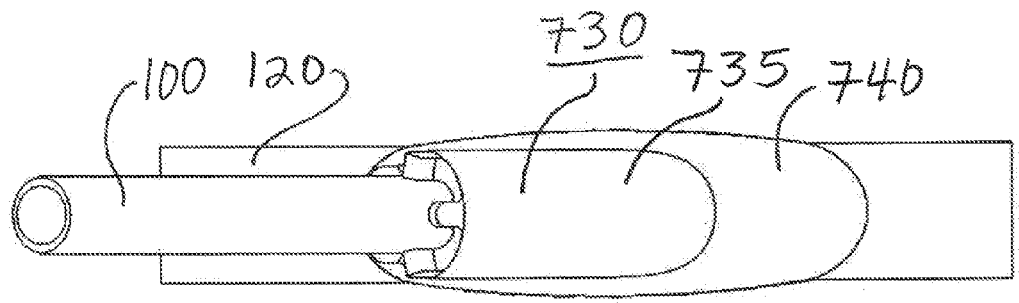
FIGS. 43–45 are top, cross-sectional front, and cross-sectional side views of a vascular coupler that includes circumferential petals and longitudinal petals.
Figure 44:
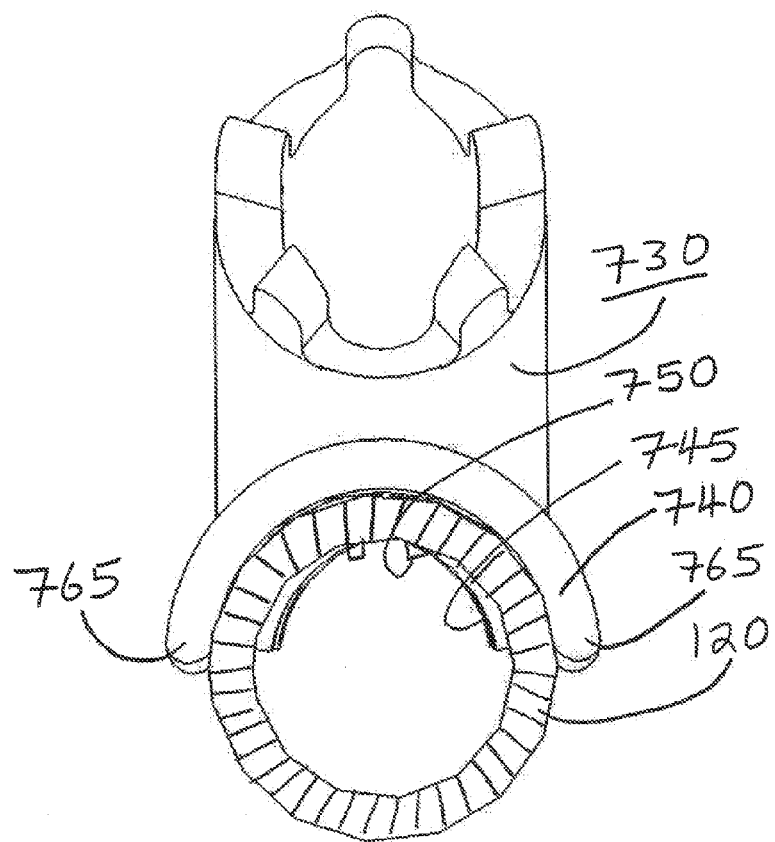
Figure 45:
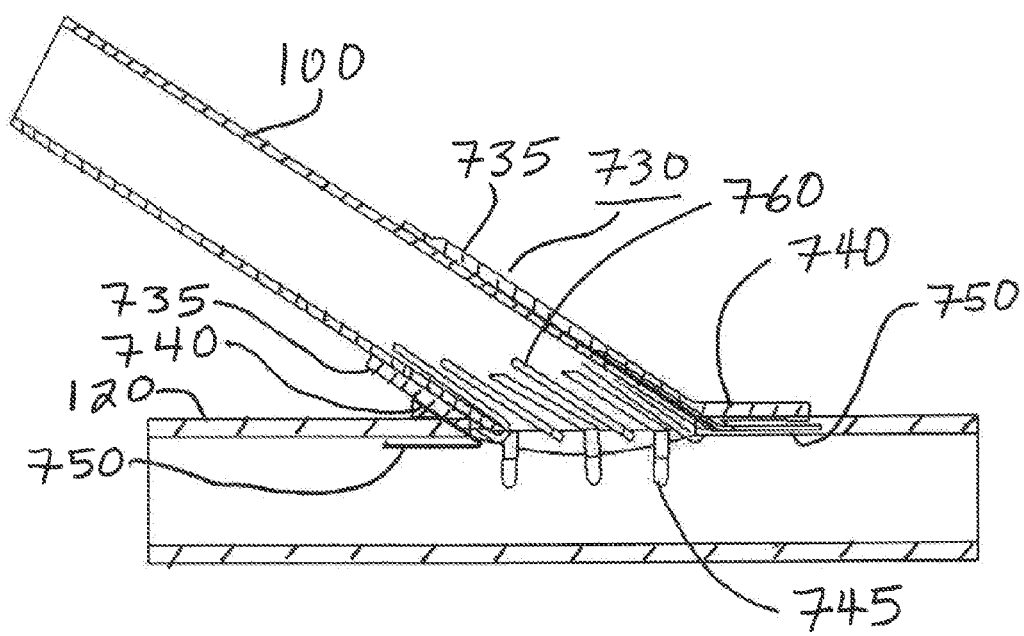
Figure 46:
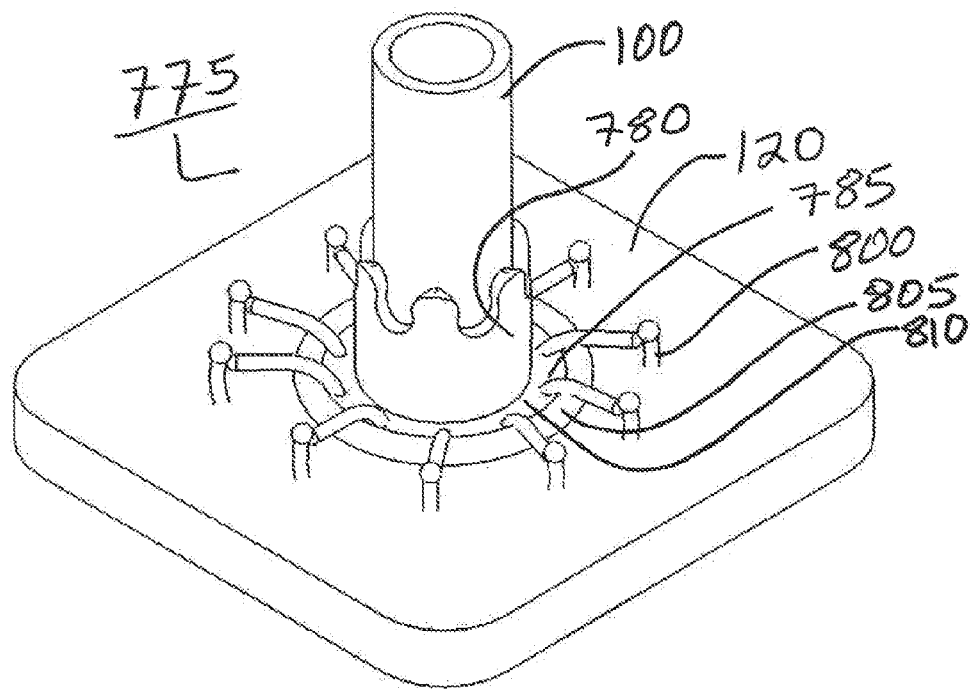
FIGS. 46–49 are perspective front, side, top, and cross-sectional side views of a vascular coupler that includes mounting clips.
Figure 47:
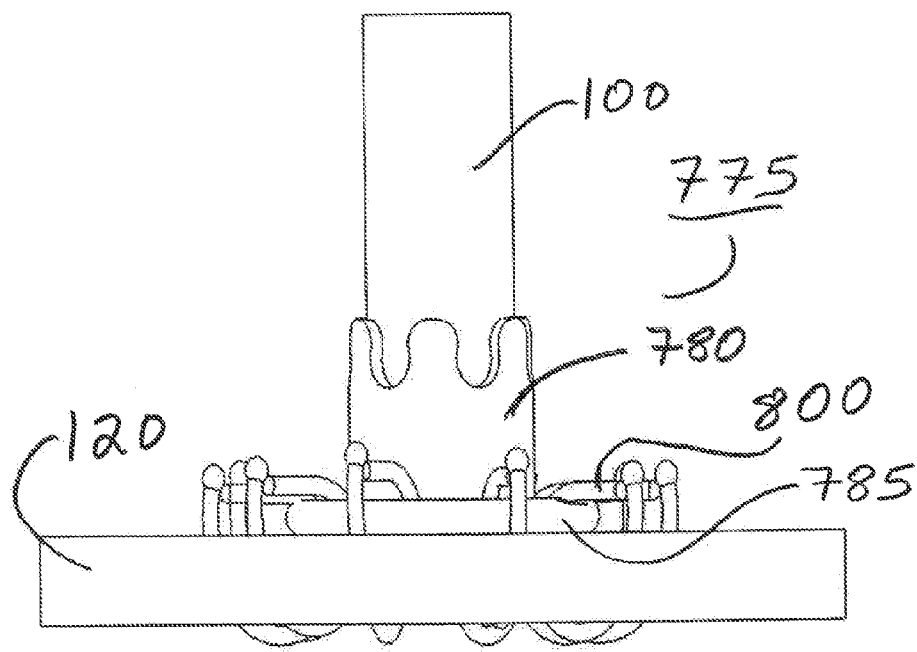
Figure 48:
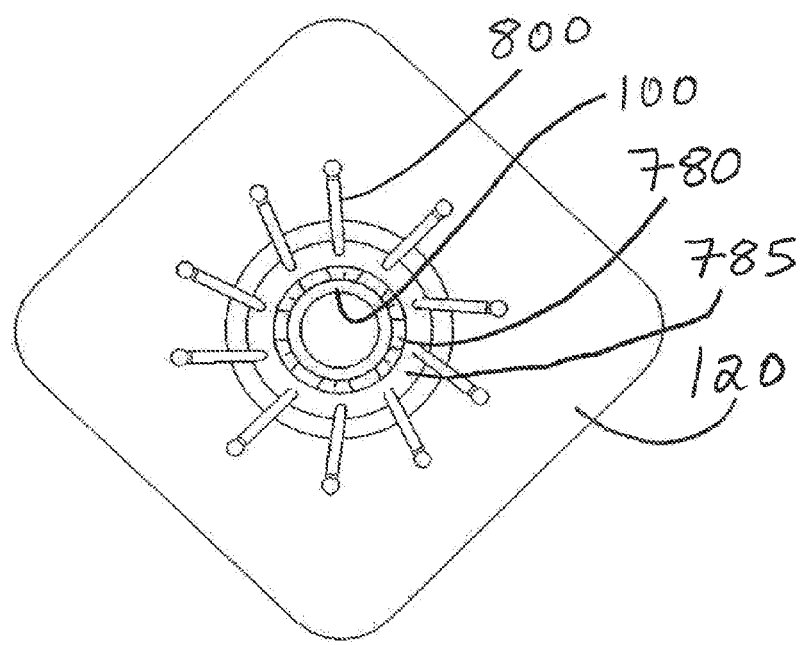
Figure 49:
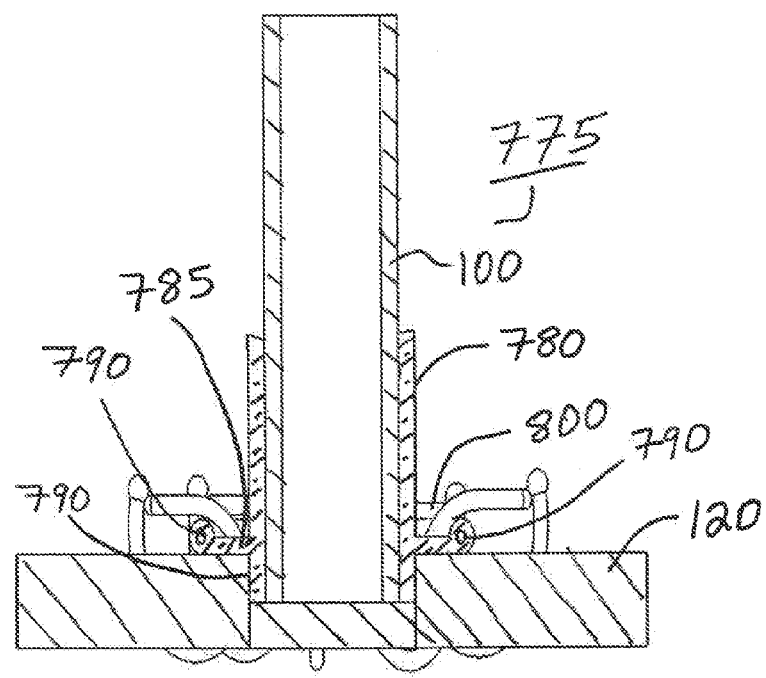

Referring to FIGS. 43–45, a vascular coupler 730 includes a stem 735, a ridge 740, circumferential petals 745, longitudinal petals 750, a hemostatic gasket 755, and securing members 760. The vascular coupler 730 is particularly configured to conform to the geometry of the vessel 120 in which the coupler is implanted. For example, the ridge 740 is curved to match the circumference of the vessel 120. As illustrated in FIG. 44, the ridge 740 includes a pair of circumferential regions 765 that encircle a portion of the circumference of the vessel. Similarly, the circumferential petals 745 are configured to conform to the inner circumference of vessel 120 by having a curved shape. The longitudinal petals 750 extend proximally and distally of the coupler along the longitudinal axis of the vessel 120. This arrangement of the petals 745, 750 contributes to increased pullout resistance of the coupler from the vessel. Similar to the vascular coupler 675, the stem 735 is at an angle relative to the ridge 740 that is less than 90°.

Referring to FIGS. 46–49, a vascular coupler 775 includes a stem 780, a ridge 785, a reinforcing ring 790, a hemostatic gasket 795, and mounting clips 800. The ridge includes a large thickness lip 805 and a thinner connecting region 810 extending between the lip 805 and the stem 780. The primary difference between the coupler 775 and the couplers above is that the mounting clips 800 are used in place of the petals in this configuration. The mounting clips 800 pass through the vessel 120 and the ridge 785, and more specifically, through the thinner region 810. The mounting clips 800 can be made, for example, of a traditional suture material or a superelastic metal, such as Nitinol. One commercially available suitable mounting clip is that marketed by Coalescent Corporation of Sunnyvale, Calif. The mounting clips 800 are used to attach the vascular coupler 775 to the vessel 120 in manners known to those of skill in the art. The reinforcing ring 790 provides strength to the ridge 785 and prevents, if necessary, pull-though of the mounting clips 800 through the ridge when the mounting clips are tightened.

Figure 50:
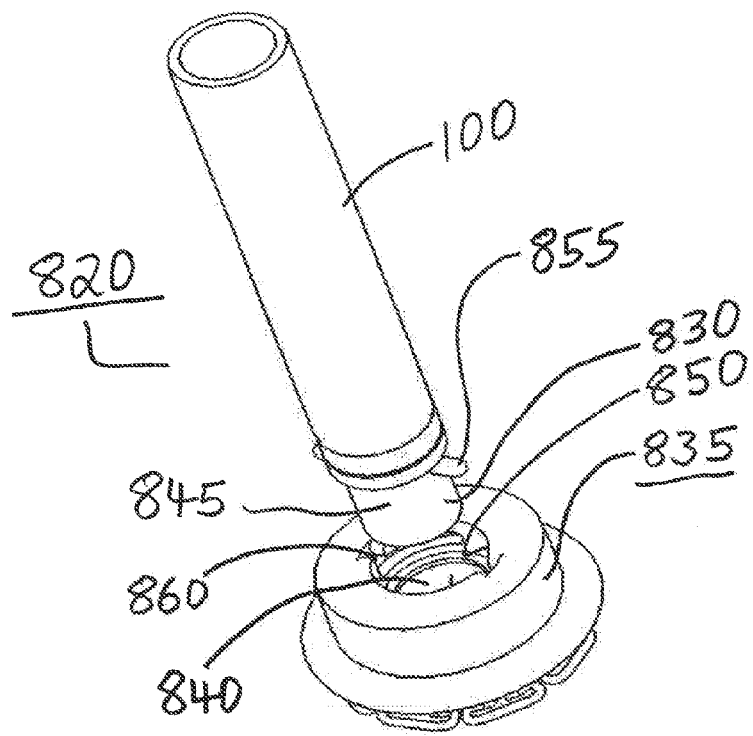
FIGS. 50–52 are perspective front, front, and cross-sectional front views of a valved coupler that includes a base and a fitting that is configured to receive a bypass vessel and be inserted into the base.
Figure 51:
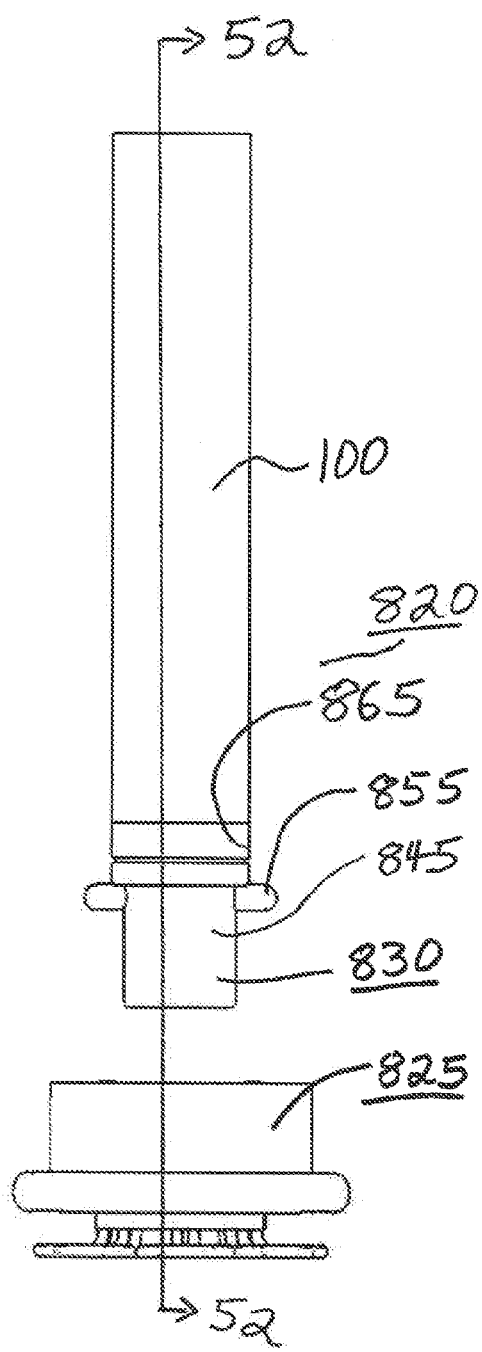
Figure 52:
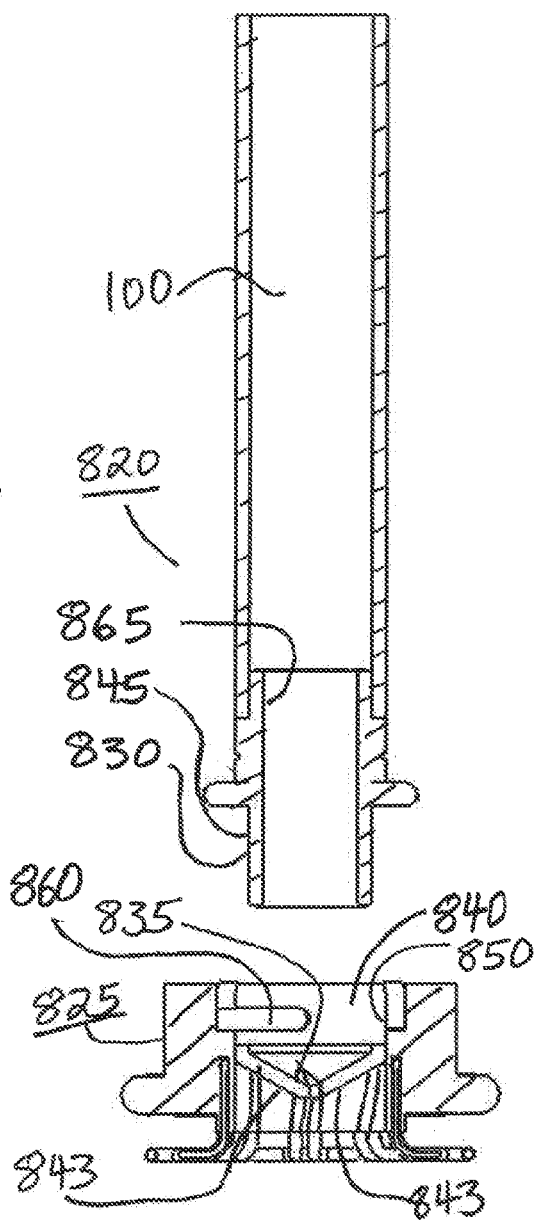
Figure 53:
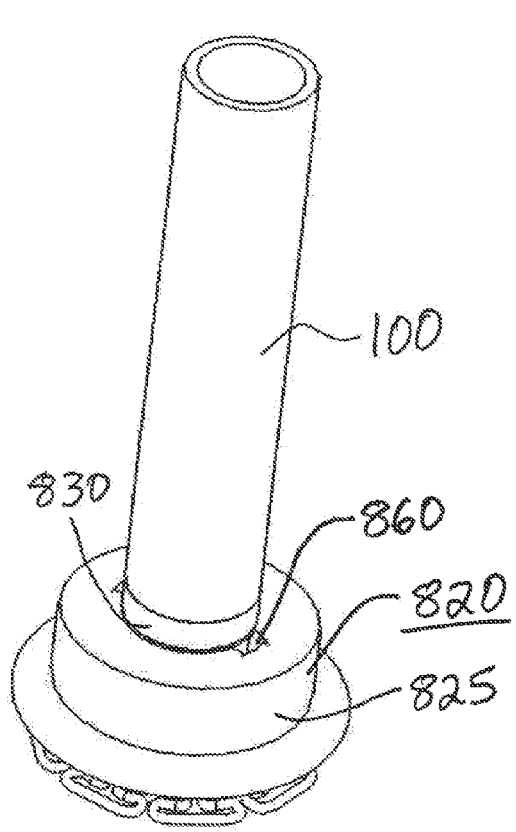
FIGS. 53–55 are perspective front, front, and cross-sectional front views of the valved coupler of FIG. 50 illustrating the bypass vessel inserted into the base.
Figure 54:
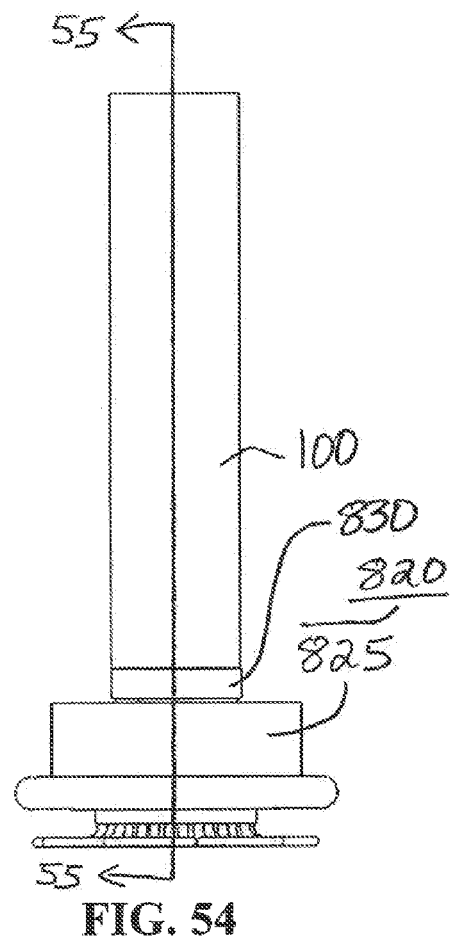
Figure 55:
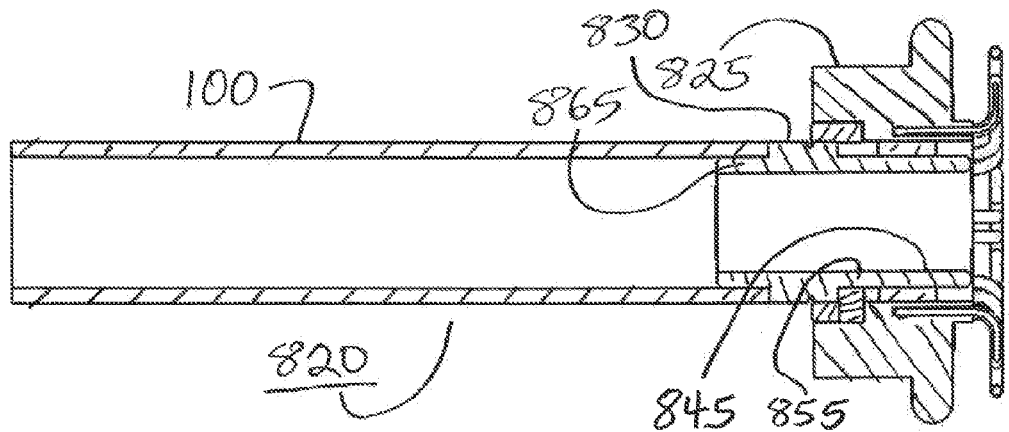

Referring to FIGS. 50–55, a valved coupler 820 includes a base 825 and a fitting 830 that is configured to receive a connecting tube 100 and be inserted into the base. The base 825 includes a bi-leaflet valve 835 mounted to the base within a lumen 840 of the base. The valve 835 is configured such that inserting the fitting 830 into the lumen 840 moves the leaflets 843 to an open position such that blood can flow from the connecting tube 100 into a vessel 120 (FIGS. 53–55). Similarly, the valve 835 is configured such that removing the fitting 830 causes the leaflets 843 to return to a closed position (FIGS. 50–52). In the open position, a first section 845 of the fitting 830 physically displaces the leaflets 843 such that they are pressed against or adjacent to an inner wall 850 of the base. The fitting 830 is retained in the base 825 by one or more tabs 855 that slide into and twist through one or more channels 860 that are formed in the wall 850 of the base. Such twist lock methods are well known in the art.

Figure 56:
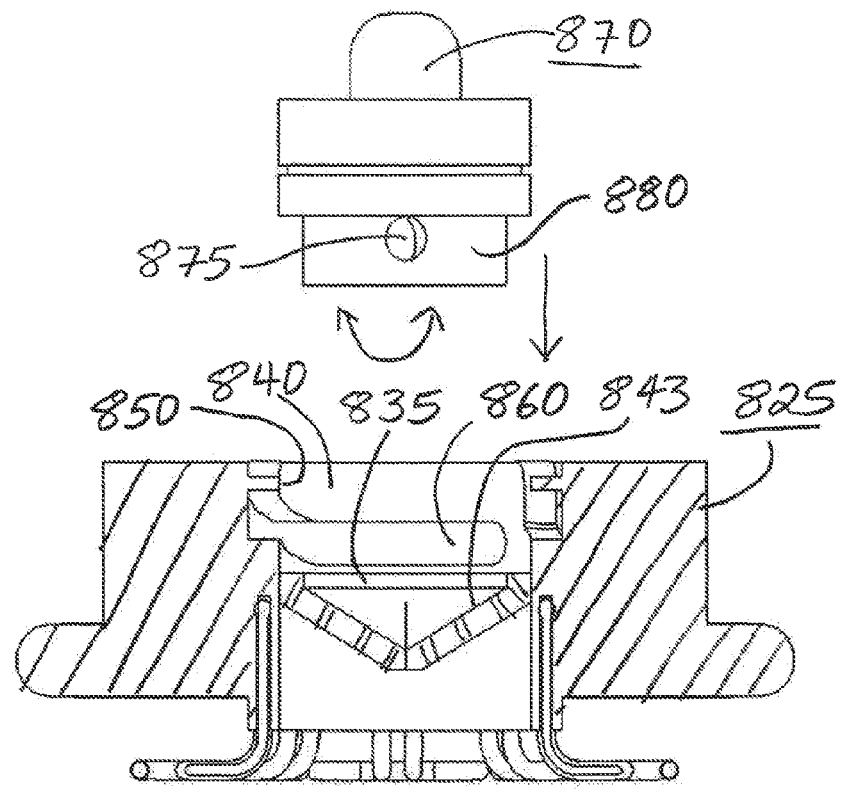
FIGS. 56 and 57 are cross-sectional side views of a closure cap being inserted and inserted, respectively, in the valved coupler of FIG. 53.
Figure 57:
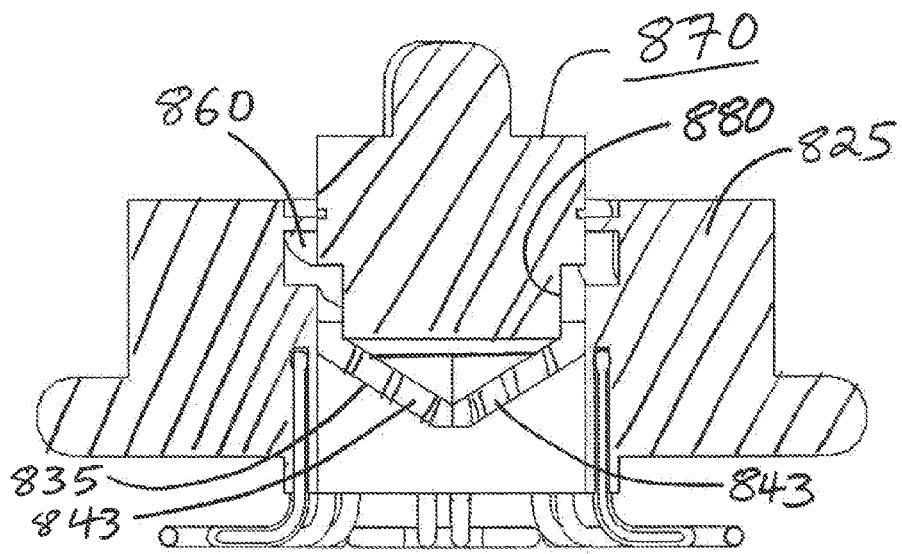

Referring also to FIGS. 56 and 57, the base 825 can be configured to receive a closure cap 870 that, similarly to the fitting 830, includes one or more tabs 875. In contrast to the fitting 830, the closure cap 870 has a reduced length first section 880, relative to the first section 845 of the fitting 830. In this manner, when the tabs 875 are inserted within the channels 860, the valve leaflets 843 are not displaced into the open position.

Figure 58:
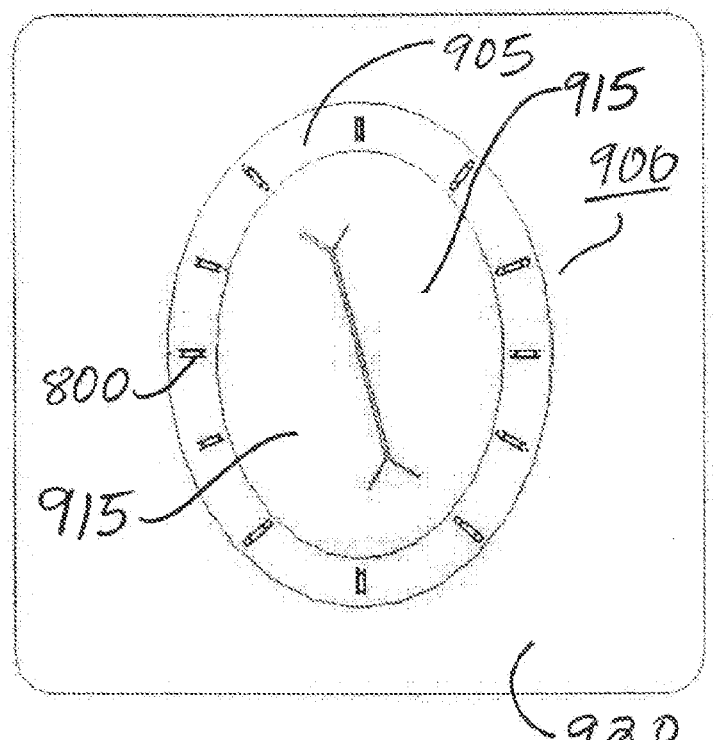
Figure 59:
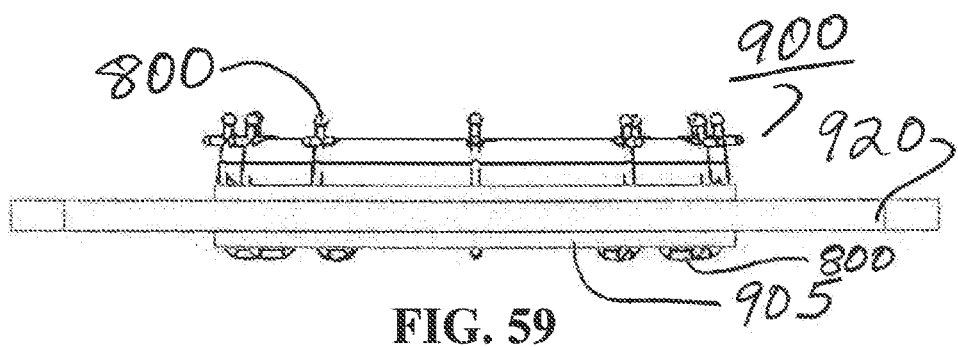
Figure 60:
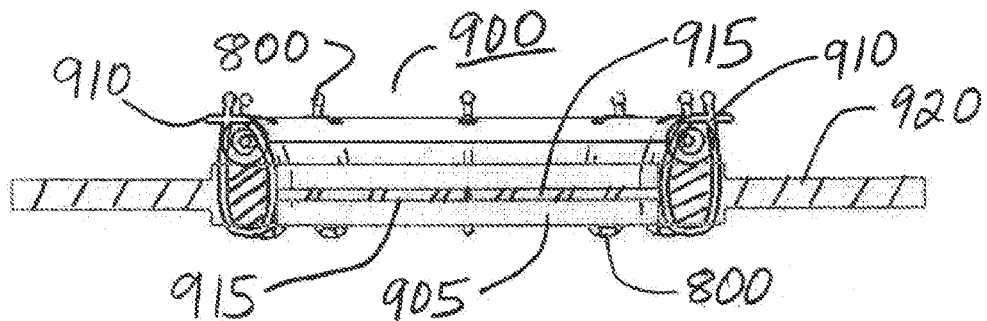

Referring to FIGS. 58–60, is a stand-alone reinforcement 900 that is comprised of many of the features above including a ridge 905 and a reinforcing ring 910. The native pair of valve leaflets 915 are prevented from separating by the ridge and ring preventing the diameter of the valve from opening up too much. Multiple sutures or mounting clips, e.g., mounting clips 800, are used to secure the reinforcement 900 to the tissue. The reinforcing ring 910 passes through the inside of the ridge 905 along all or part of the circumference of the ring. The reinforcement 900 advantageously can be easily implanted in tissue 920 through a minimally invasive surgical procedure.

The reinforcing ring can be a Nitinol hoop or band and may form a complete circumference or a partially circumference (e.g., complete or incomplete cross sectional circle, to maintain the same, or smaller diameter than a complete circle, depending on the annealed geometry and diameter). While Nitinol has many unique features and benefits, other materials may also be used for the reinforcing ring. The ring may have a square, rectangular, round, oval, combination or other shape or geometry. The surface of the metal or metal alloy, may be electropolished, or have a coating to enable or assist the healing process. Bonding and securing to tissue can be accomplished by sutures (traditional, Nitinol, or other), adhesive, combination or other. The ring may be expanded from its resting, annealed configuration, and attached to a deployment tool. The ring may then be attached to tissue (such as a valve annulus) and secured, using sutures, adhesive or a combination. The deployment tool may then be removed, allowing the ring to recover back to its resting, or as annealed configuration, cinching, placating, bunching, or otherwise bringing the tissue(s) together to resist increase in the valve annulus diameter, e.g., caused by chronic cardiac conditions.

A second configuration is similar to that above but further includes an overmolded jacket with a proximal strain relief in the stem region. Holes, slots, reduced thickness areas in the wall, combination or other may be used to guide and or enable the use of sutures.

A third configuration that is similar to those above does not include a stem region. This configuration resembles a circle and may have a reinforcing band, ring or other.

A fourth configuration includes holes, slots, reduced thickness areas, combination or other to guide, assist or enable the use of sutures with the anastomotic coupler.

The valved coupler can provide a safe, effective, quick and intuitive-to-use vascular coupler that incorporates a valve and quick connect, quick disconnect features. The purpose of the valve, when in its closed position, is to prevent, obstruct and or limit fluid or air flow. Another purpose is to prevent or obstruct flow, until a tube or other is inserted into the inner diameter of the coupler, opening the valve and allowing flow. Once the tube or other is removed, the valve would close. Alternatively, the coupler may not contain a valve—a replaceable plug, cap or occluding piece may be used when flow is not desired (in between treatments for example). The cap (or plug) may also be used with the valved coupler. When inserted, it may be shorter, and not be in contact with the valve (and thus the opening), but close enough to provide a reinforcement to the valve or valve assembly components.

Additional uses for the valved coupler include being used as a permanent or temporary access port for cardiovascular, gastrointestinal, neurological, reproductive, lymphatic, respiratory or other applications. The valved coupler may be used during therapeutic infusion, diagnostic monitoring or sampling, blood flow rerouting to provide ventricular assist for congestive heart failure (from femoral artery to another vessel, with or without the assistance of a pump). The valved coupler can be permanently closed by using a cap or other component or method. Sealing may be accomplished by mechanical interference fit, adhesive, combination or other. The coupler, with or without modifications, may be used as a device and method to deploy, and or secure (temporarily or permanently) medical devices, including, but not limited to, such devices as a ventricular conduit (between ventricle and coronary artery, or other) from companies including Ventrica (Fremont, Calif.) and HeartStent (Minneapolis, Minn.), and AV shunts from companies such as Vasca (Tewksbury, Mass.). The valved coupler also can be used for therapeutic infusion, diagnostic monitoring or sampling, and reinforcement/replacement of cardiac valves. The valved coupler also can be removed, and replaced with another device. The replacement device may be another valved coupler, non-valved coupler, or other device.

The valved coupler can be of any diameter (e.g., from 1 mm to 20 mm or larger), any angle (e.g., from 15 to 120 degrees), any geometry (e.g., round, oval, square, combination, etc.), and have any suitable stem length (e.g., from 2 mm to 20 mm or longer). In addition, the ridge section may be a different geometry than the stem (e.g., the stem may be round, while the ridge may be oval).

The design of the valve can include a separate piece bonded inside the inner diameter of coupler (i.e., using an adhesive, solvent, heat, combination or other suitable process), a removable valve assembly, an overmold and valve fabricated as one piece with the coupler petals, on the connection tube end the coupler piece may utilize a removable/replaceable plug or cap rather than a valve, or the valve may be designed to not completely close to allow a restricted flow to pass through the coupler. The valve type can be a duck bill, a flapper, a check valve, a dilating membrane, or other suitable type and design. The valve can be located at any location inside and or on the outside of the coupler. The preferred location is inside the inner diameter of the stem. Moreover, one or more valves may be used.

The engagement of the valved coupler with the connecting tube (e.g., bypass graft or vessel) can be by using mating threads, a push in/twist to lock, a tapered tube/friction fit, or an expandable, complete or partial circumferential balloon (or other expanding/engaging structure) on or near the end of the connecting tube. The expandable structure may provide both a mechanical connection, as well as a fluid tight seal between the OD of the connecting tube end, and the ID of the valve structure.

The connecting tube may have reference markings, and or a larger diameter section to abut up against the edge of the stem, or other method to confirm that the tubing end has been fully inserted, and that the valve is in the open position.

The valve material may be made of the same or different material from coupler or coupler overmold component. The valve may contain a reinforcing material, such as Nitinol, to act as a hinge, and or a reinforcing support. The hinge or support may be on the inside, outside, in-between or combination of the valve structure. The reinforcing hinge or support material may be flat, round, combination or other.

Figure 61:
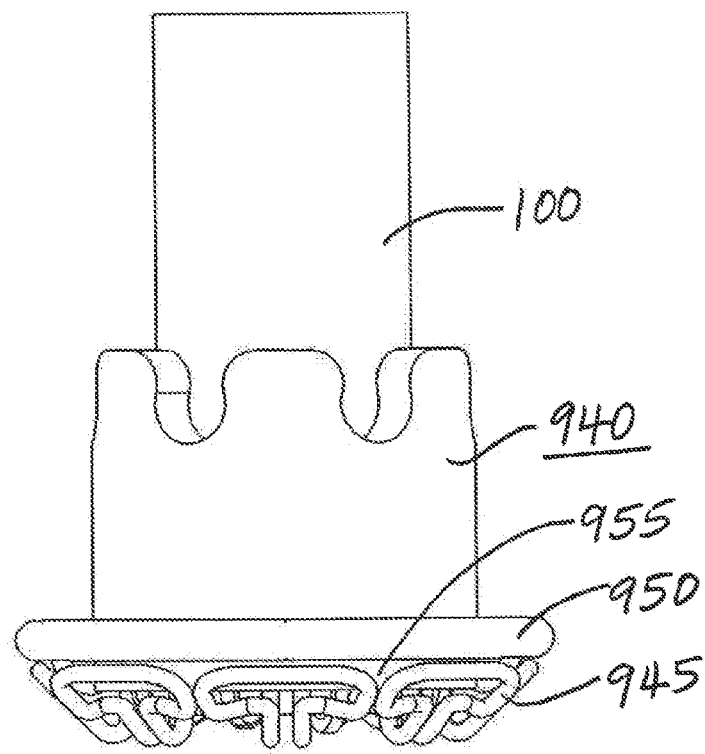
FIGS. 61 and 62 are side and cross-sectional side views of a vascular coupler that includes multiple petals that are oriented in the general direction of the ridge.
Figure 62:
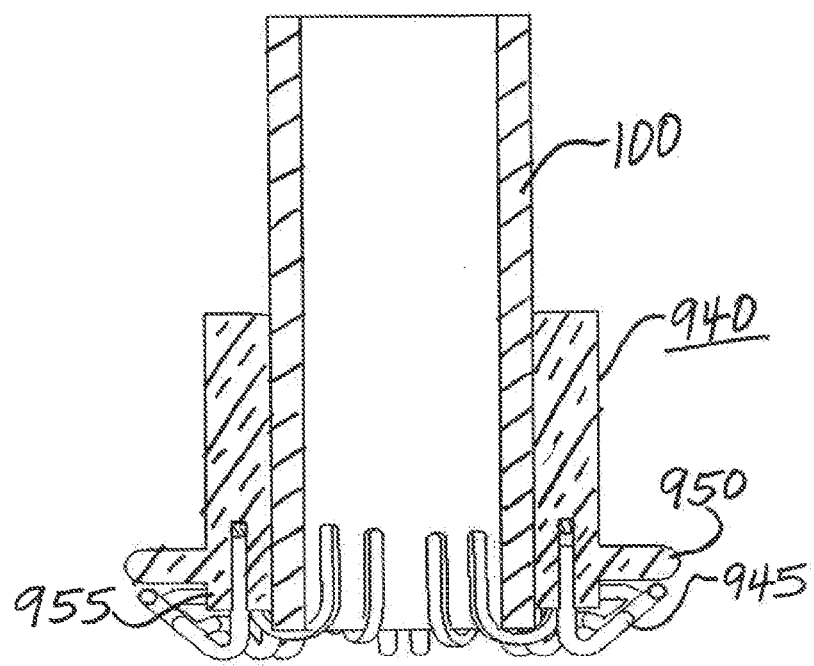
Figure 63:
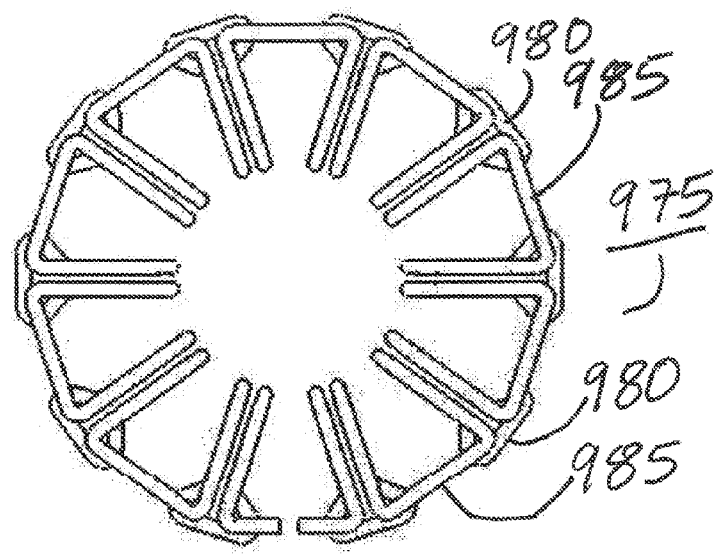
FIGS. 63–65 are top, side, and perspective views of a single wire or rod petal member.
Figure 64:
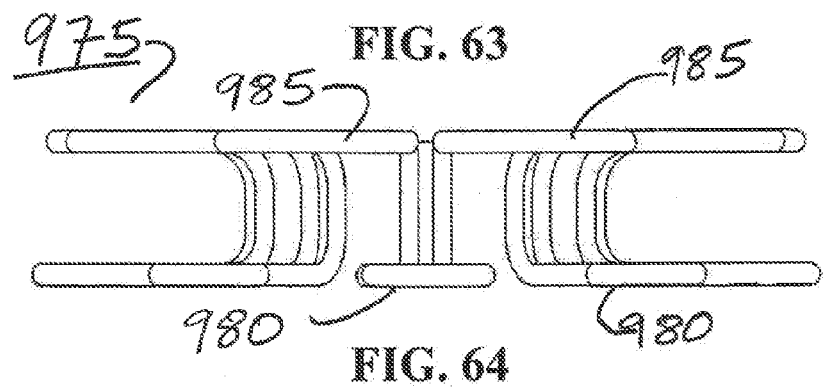
Figure 65:
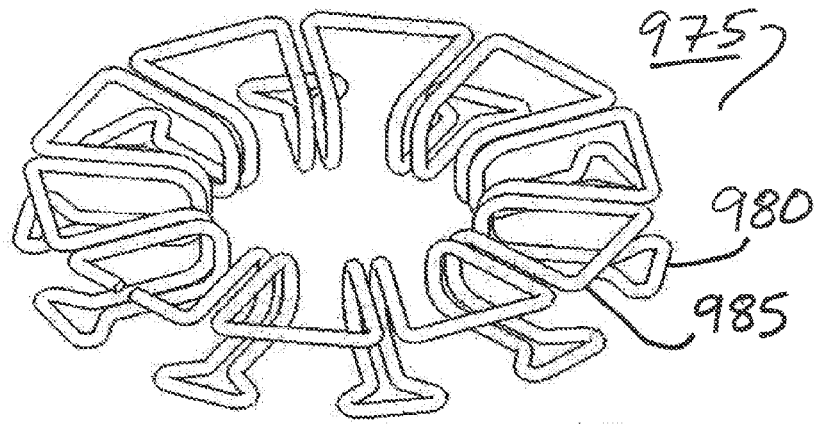
Figure 66:
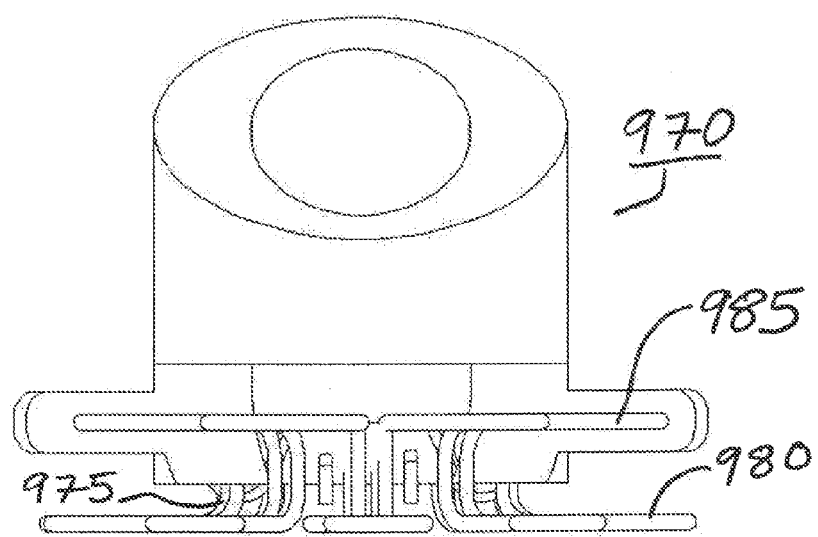
FIG. 66 is a cross-sectional side view of a vascular coupler incorporating the single wire or rod petal member of FIG. 63.

Of course, the vascular couplers described above can be implemented with numerous variations in the components. For example, referring to FIGS. 61 and 62, a vascular coupler 940 includes multiple petals 945 that are oriented in the general direction of the ridge 950. For example, the angle between the petals 945 and the hemostatic gasket 955 can be approximately 45 degrees. In this configuration, there is increased binding of the vessel 120 between the petals 945 and the ridge 950.

Referring to FIGS. 63–66, a vascular coupler 970 similar to those described above differs by including a petal member 975 that is fabricated from a single wire, rod or etched sheet having joined ends, although it is not strictly necessary to join the ends. In forming the petal member 975, the wire or rod is bent to form petals 980 and ridge reinforcements 985. The petal member 975 may have a pair of ends 990 that are separated (as illustrated) or adhered together.

Figure 67:
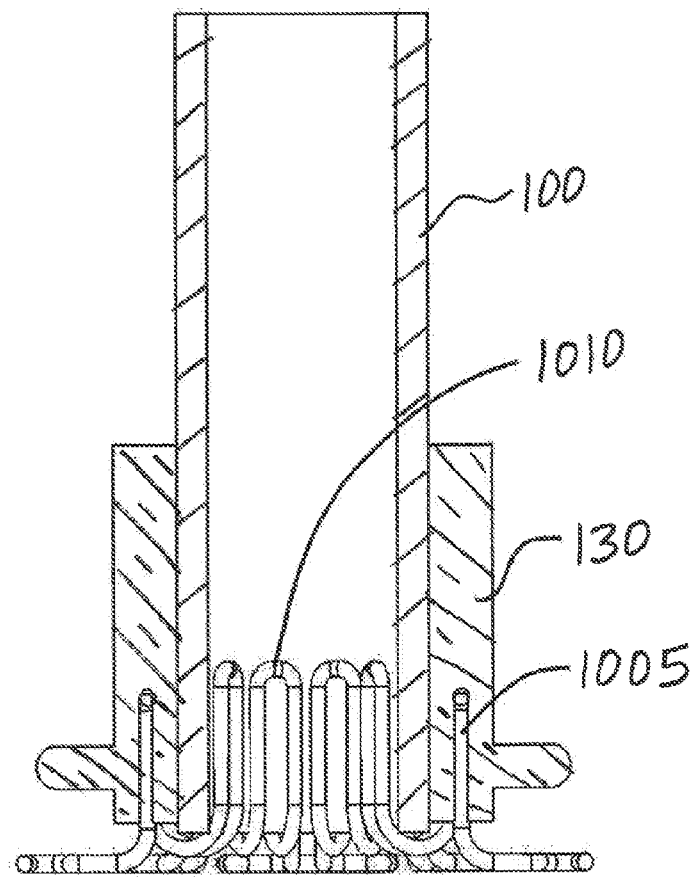
Figures 71, 72, 73:
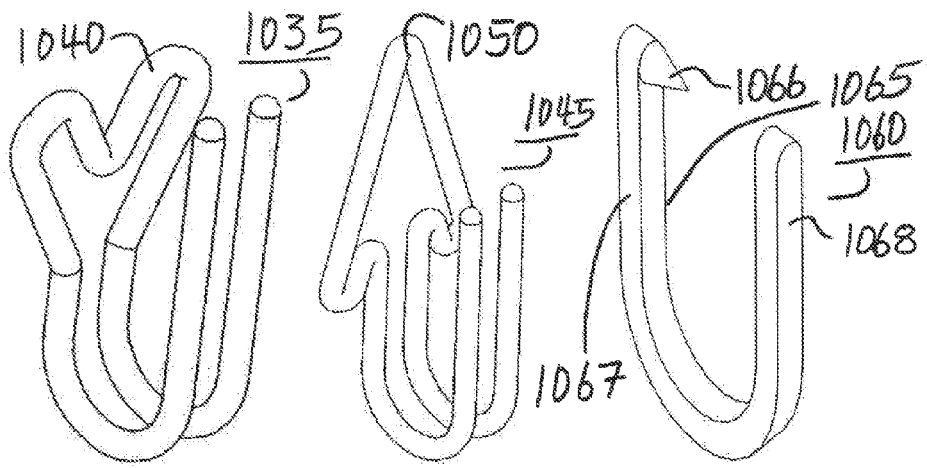

In another variation of the vascular couplers described above, the securing members also can be varied in numerous manners. For example, referring to FIGS. 67 and 68, a securing member 1000 includes a pair of parallel sections 1005 that are joined by a U-shaped tissue contacting member 1010. The parallel sections 1005 are either embedded within the stem 130 or positioned on the outer surface of the stem. The U-shaped tissue contacting member 1010 extends into and along the inner wall of the coupler to compress the vessel 100 against the coupler. Similarly, referring to FIGS. 69 and 70, a securing member 1020 includes a pair of parallel sections 1025 that are joined by an inverted V-shaped tissue contacting member 1030. The parallel sections 1025 are either embedded within the stem 130 or positioned on the outer surface of the stem. The inverted V-shaped tissue contacting member 1030 extends into and along the inner wall of the coupler to compress the vessel 100 against the coupler. Similarly, FIG. 71 illustrates a securing member 1035 that includes a broad V-shaped tissue contacting member 1040 that provides additional contact against the vessel. Likewise, FIG. 72 illustrates a securing member 1045 that includes a triangular shaped tissue contacting member 1050 that provides additional contact against the vessel.

The securing members also can be configured to have a J-shape. In this configuration, the shorted segment is positioned below the ridge and then the longer segment extends unto the lumen of the coupler to secure the vessel to the coupler. In this manner, the ridge does not need channels to receive the securing member.

Figures 74, 75, 76:
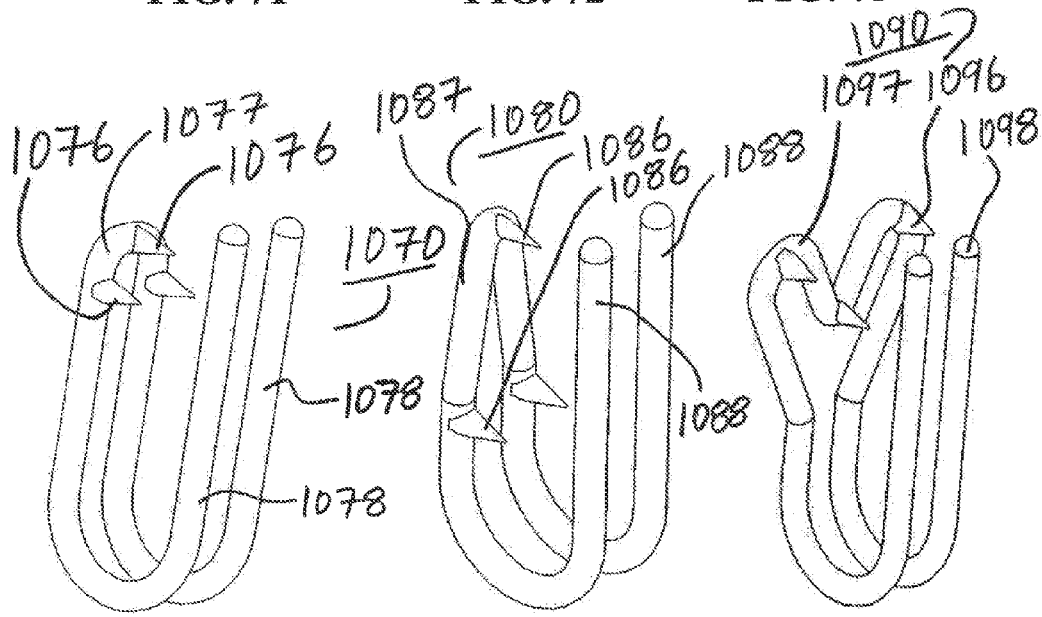

The securing members can be further modified to increase the retention strength for retaining the vessel 100 within a coupler by including tissue penetrating members. For example, a securing member 1060 includes a U-shaped member 1065 and a tissue penetrating member 1066. The tissue penetrating member 1066 is directed inwardly from a first arm 1067 in the direction of a second arm 1068. Referring to FIG. 74, a securing member 1070 that is similar to the securing member 1000 further includes tissue penetrating members 1076 that are directed inwardly from an inverted U-shaped first arm 1077 in the direction of second arms 1078. Referring to FIG. 75, a securing member 1080 that is similar to the securing member 1020 further includes tissue penetrating members 1086 that are directed inwardly from an inverted U-shaped first arm 1087 in the direction of second arms 1088. Referring to FIG. 76, a securing member 1090 that is similar to the securing member 1035 further includes tissue penetrating members 1096 that are directed inwardly from a broad V-shaped first arm 1097 in the direction of second arms 1098. Referring to FIG. 77, a securing member 1100 that is similar to the securing member 1045 further includes tissue penetrating members 1106 that are directed inwardly from a triangularly-shaped first arm 1107 in the direction of second arms 1108. Referring to FIG. 78, a securing member 1110 that is similar to the securing member 1060 further includes angled tissue penetrating members 1116 that are directed inwardly and downwardly from a first arm 1117 in the direction of a second arm 1118.

Referring to FIGS. 79–81, the petals can be configured as longitudinal wires or rods that compress the vessel wall between the petals and the ridge. Specifically, a vascular coupler 1150 includes an overmolded ridge 1153 in which a longitudinal petal 1155 is partially embedded. In particular, the longitudinal petal 1155 includes a longitudinal section 1160 that is oriented along the axis of the vessel 120 in which the coupler 1150 is implanted. The petal 1155 also includes a first circumferential section 1165 and a second circumferential section 1170. The circumferential sections 1165, 1170 extend from the longitudinal section 1160 and connect to parallel longitudinal sections 1175. An opposite petal 1155 is positioned on the opposite side of the coupler, separated laterally for the first petal.

Another variation in the vascular couplers described above is the use of a circumferential spring member. For example, referring to FIGS. 82–84, a vascular coupler 1200 includes a stem 1205, a ridge 1210, a hemostatic gasket 1215, and a circumferential spring member 1220. The circumferential spring member 1220 includes petals 1225 that are separated by inverted U-shaped connectors 1230. The spring member 1220 provides radial reinforcement to the stem 1205. In particular, the stem 1205 can be made of a weak, compliant material and the spring member used to provide radial strength to the coupler. The spring member provides radial expansion and contraction similar to a sutured or native anastomosis. The spring also provides a dynamic response to the pulsatile forces in the circulatory system. The spring member can be made through a number of techniques. For example, a sheet or a superelastic/shape memory material, such as Nitinol, can be cut or etched to have the pattern of the spring member. The etched or cut sheet then can be annealed to the shape illustrated in FIGS. 82–84, placed in a mold, and overmolded. The two edges of the sheet used to form the spring member can be joined or left separated by a slight gap 1235. The spring member can be fabricated from the same material as the petals.

Figure 85:
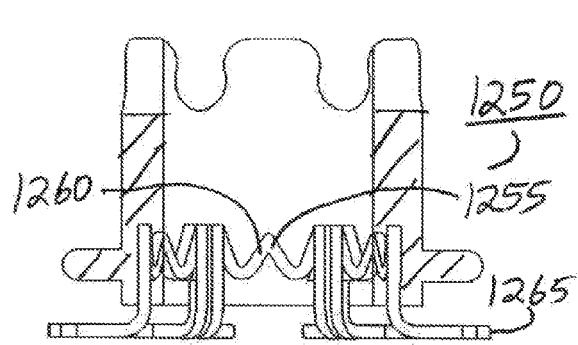

Referring to FIG. 85, a vascular coupler 1250 that is similar to the vascular coupler 1200 includes a narrower spring member 1255 that has reduced height, inverted U-shaped connectors 1260 connecting the petals 1265.

Figure 86:
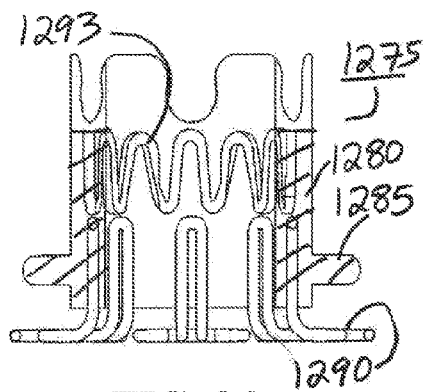
Figure 87:
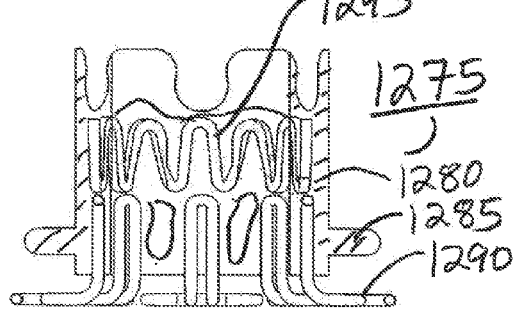

Referring to FIGS. 86 and 87, a vascular coupler 1275 includes a stem 1280, a ridge 1285, petals 1290, and a spring member 1293. The spring member 1293 is formed, for example, by etching a sheet of a superelastic/shape memory material and then annealing the shape of the finished spring member 1293. As illustrated, the spring member 1293 is separate from and unattached to the petals 1290. The spring member 1293 and the petals 1290 are formed within the stem 1280 by placing them in a mold and overmolding them with the material used to form the stem. Although the spring member 1293 is shown as having a generally sinusoidal configuration, other configurations may be used in this embodiment. The spring member provides a response to deflection that can be modified by the material used, the geometry, width, thickness, etc. The response can also be modified by the design of the spring element. The spring member may also be useful as a radial reinforcement for the overmolded coupler.

Figure 88:
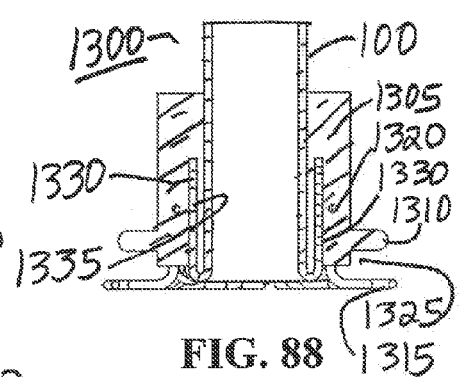
FIG. 88 is a cross-sectional side view of a vascular couplers having a groove configured to receive an everted end of a bypass vessel.
Figure 89:
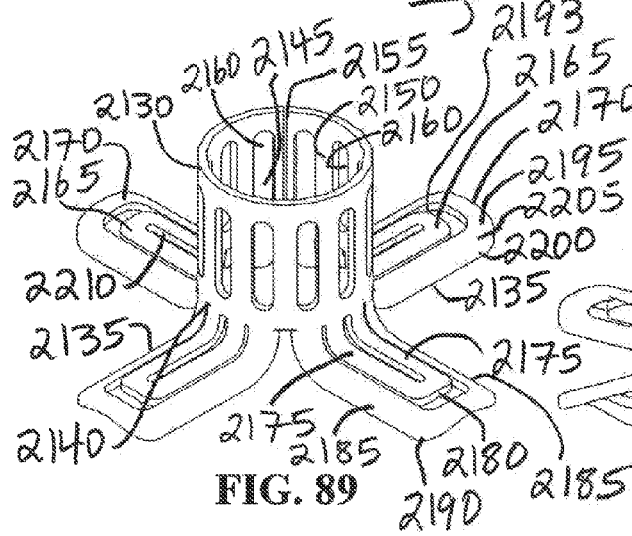
FIGS. 89–92 are perspective and bottom views of a second general class of vascular couplers based on non-overmolded tubes.
Figure 90:
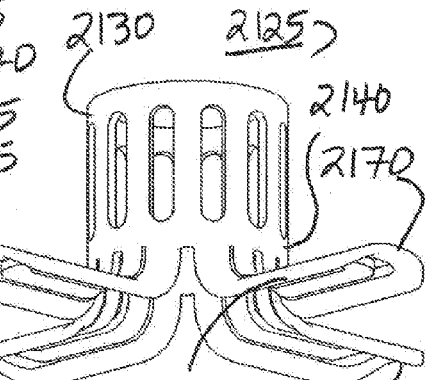
Figure 91:
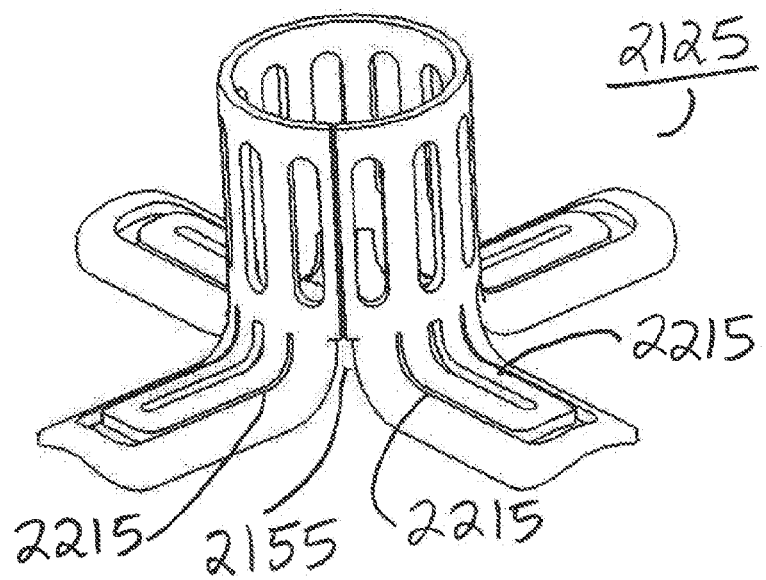
Figure 92:
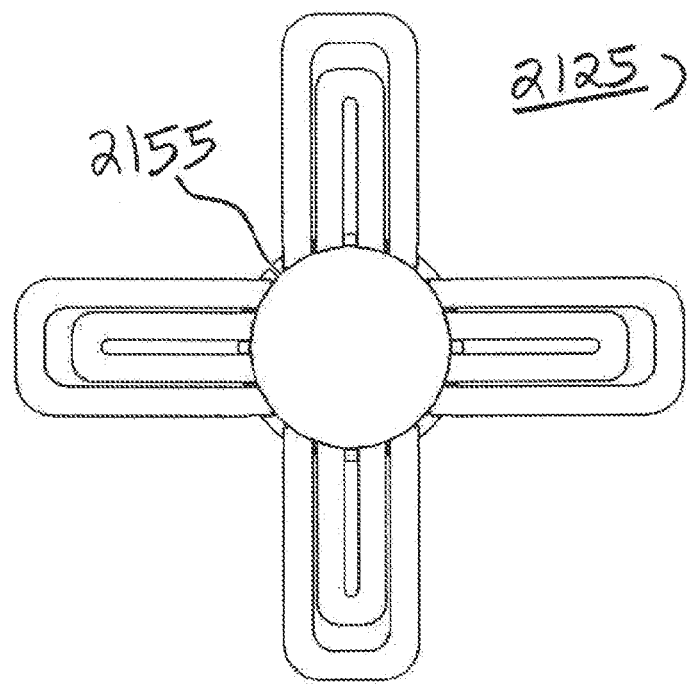

Referring to FIG. 88, the vascular couplers herein may be modified to include a groove within the distal coupler wall to receive an everted end of the bypass vessel 100. A vascular coupler 1300 includes a stem 1305, a ridge 1310, petals 1315, a reinforcing ring 1320, and a hemostatic gasket 1325. The coupler 1300 includes a groove 1330 that is coaxial with the longitudinal axis of the coupler and is large enough to receive an everted end 1335 of the vessel. A tool can be used to insert the everted end of the vessel into the groove. The vessel may be additionally secured to the coupler 1300 using the securing members described above, sutures, adhesives, mechanical interference fit, or a combination of these or other suitable methods and materials.

Although the above vascular couplers have generally been formed to include an overmolded portion, vascular couplers of a non-overmolded design also can be fabricated. For example, referring to FIGS. 89–92, a vascular coupler 2125 includes a stem 2130 and petals 2135 that extend from a base 2140 of the stem. The angle formed between the stem 2130 and the petals 2135 is between approximately 80 degrees and 100 degrees and, more particularly, approximately 90 degrees.

The stem 2130 includes an upper opening 2145, a channel 2150 passing between the upper opening 2145 and the base 2140, and a lengthwise slot 2155 along the entire length of the stem and passing from an outer surface of the stem to the channel 2150. As described in more detail below, the lengthwise slot 2155 allows the cross-sectional profile of the stem 2130 to be advantageously reduced during loading of the bypass vessel on or in the coupler and during implantation of the vascular coupler 2125. The stem 2130 also includes lengthwise slots 2160 that pass from the outer surface of the stem to the channel 2150. However, the slots 2160 do not extend the entire length of the stem 2130 but instead extend only a portion of the length of the stem. The slots 2160 remove material from the stem and thereby, when the coupler is implanted in a vessel, reduce the amount of foreign material in contact with tissue and blood.

The petals 2135 include an inner clip 2165 and an outer clip 2170, both of which extend from the base 2140. The petals 2135 are used to attach the vascular coupler 2125 to a vessel, such as the aorta. In particular, either of the inner clips 2165 or the outer clips 2170 are inserted through an opening in the vessel and allowed to expand to contact the inner lumen of the vessel. The other of the inner clips 2165 and the outer clips 2170 are positioned on the outside of the vessel. In this manner, the vessel is positioned between the inner clips 2165 and the outer clips 2170.

The inner clip 2165 is in the form of a pair of lengthwise edges 2175 that extend from the base 2140 at a first end of the edges and a widthwise edge 2180 at a second, opposite end of the edges. The lengthwise edges 2175 and the widthwise edge 2180 are surrounded by a pair of lengthwise edges 2185 and a widthwise edge 2190 of the outer clip 2170. The various edges of the outer clip 2170 are separated from the various edges of the inner clip by a channel 2193 that extends from the base 2140 to the widthwise edge 2185. Like the edges of the inner clip 2165, the lengthwise edges 2185 extend from the base 2140 at a first end of the edges and the widthwise edge 2190 is at a second, opposite end of the edges and connects the lengthwise edges 2185.

The various lengthwise and widthwise edges have upper surfaces 2195 and lower surfaces 2200 that are connected by side surfaces 2205. The joints between the side surfaces 2205 and the upper surfaces 2195 and the lower surfaces 2200 may be smoothed, angled, gradual, or sharp. In general, the joints will be configured to limit the likelihood of damage to tissue or blood when, as described below, the coupler 2125 is implanted in a vessel.

The inner clip 2165 also includes an optional slit 2210 along its length. The slit 2210 can be wide or narrow and its shape is not particularly limited. Moreover, the slit 2210 can have widthwise slits (not shown) extending into the lengthwise edges 2175 and the widthwise edge 2180. Similarly, the lengthwise edges 2185 and the widthwise edge 2190 of the outer clip 2170 optionally may have slits (not shown) extending from the slit 2210 into the edges 2185 and 2190. These optional slits are used to provide more flexibility to the clips 2165 and 2170 and, further, to reduce the amount of foreign material in contact with the recipient's blood and tissue. The inner clip 2165 and the outer clip 2170 are curved to generally have a radius of curvature that matches the inside of the vessel in which the coupler 2125 is to be implanted.

FIGS. 89–92 illustrate one configuration of the interface 2215 between the channel 2193 and the base 2140 of the stem 2130. Although FIGS. 89–92 show the interface 2215 being of a constant width, the interface can be wider than the width of the channel 2193 such that, when implanted, more tissue can be received within the interface without pinching of the tissue between the outer clip 2170 and the inner clip 2165. For example, the interface 2215 can be formed as a round opening.

Figure 93:
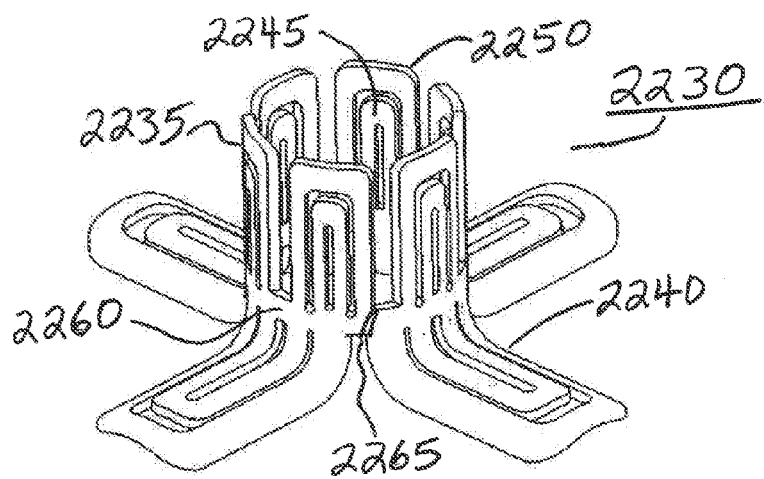
FIGS. 93 and 94 are perspective and side views of a non-overmolded vascular coupler having a slot.
Figures 94, 95:
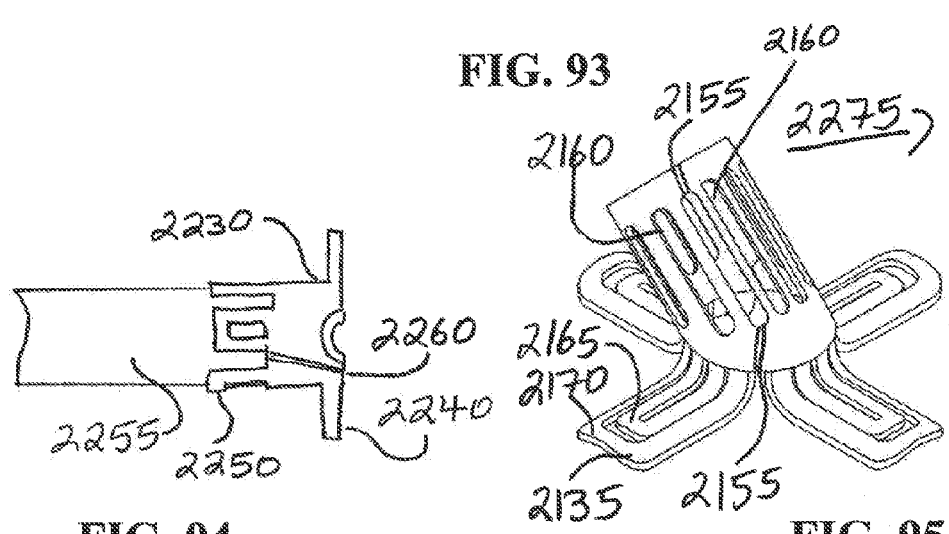
FIGS. 95–98 are perspective, side, and bottom views of a non-overmolded, angled vascular coupler having a slot.
Figure 96:
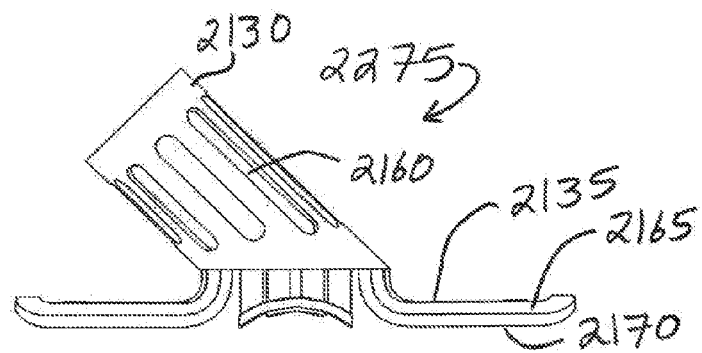
Figure 97:
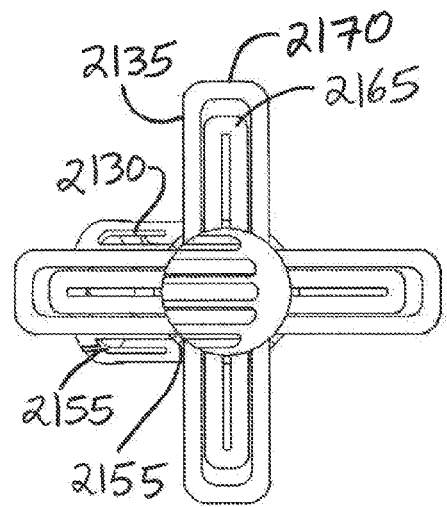
Figure 98:
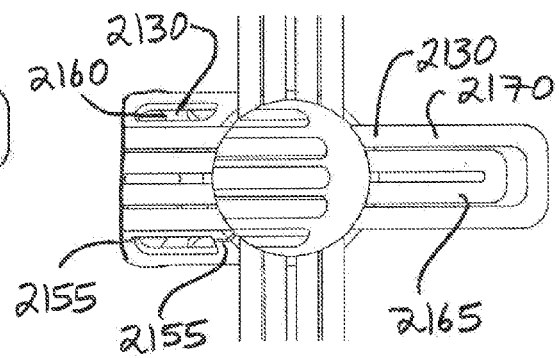
Figure 99:
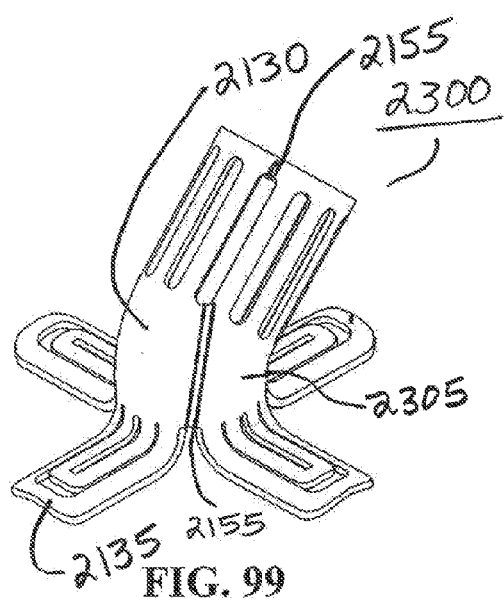
FIGS. 99–102 are perspective, side, and bottom views of a non-overmolded, angled vascular coupler having a slot and an extended base.
Figure 100:
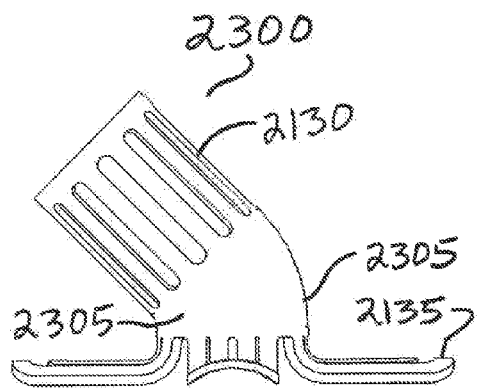
Figure 101:
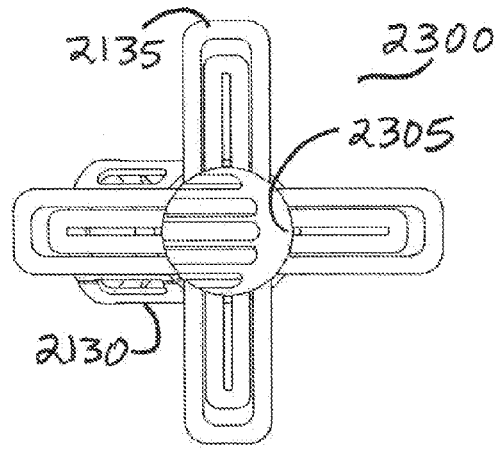
Figure 102:
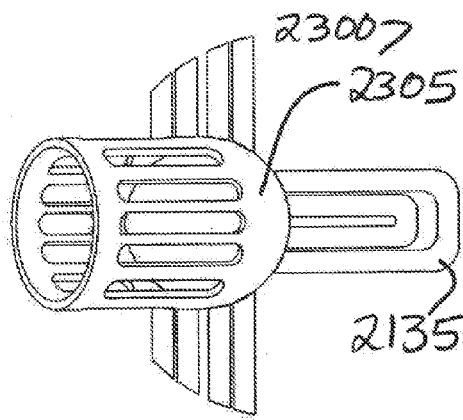
Figure 103:
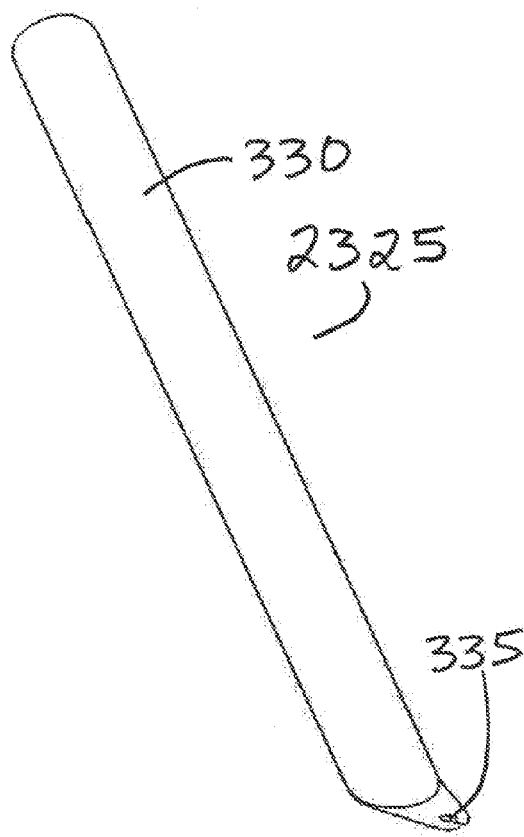
FIGS. 103–107 illustrate various views of a deployment tool for deploying, e.g., a non-overmolded, angled vascular coupler.
Figure 104:
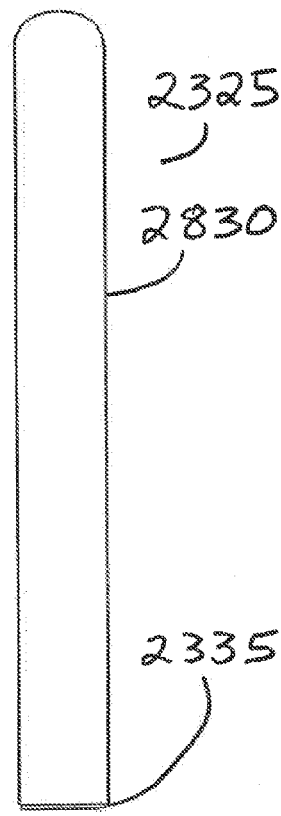
Figure 105:
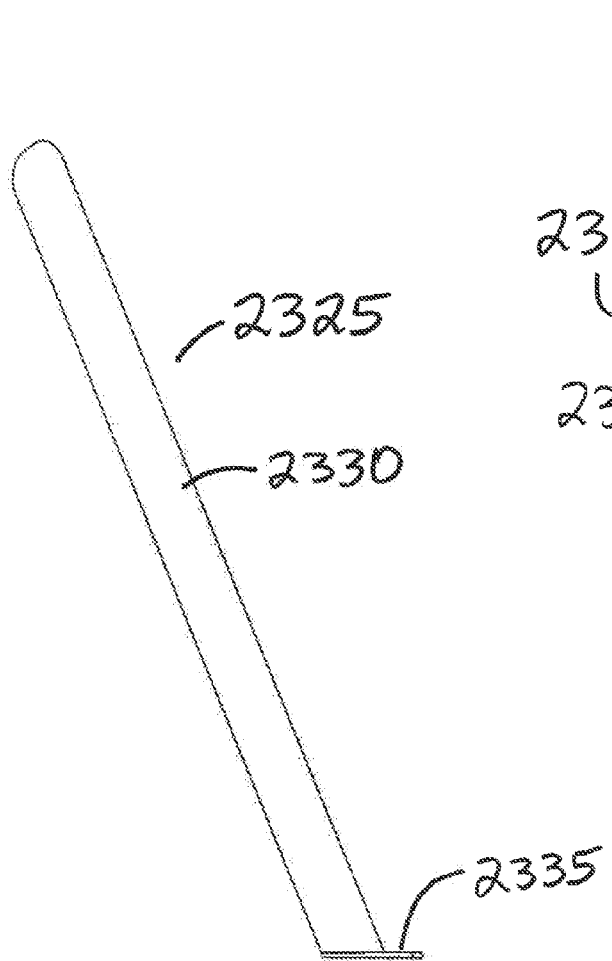
Figure 106:
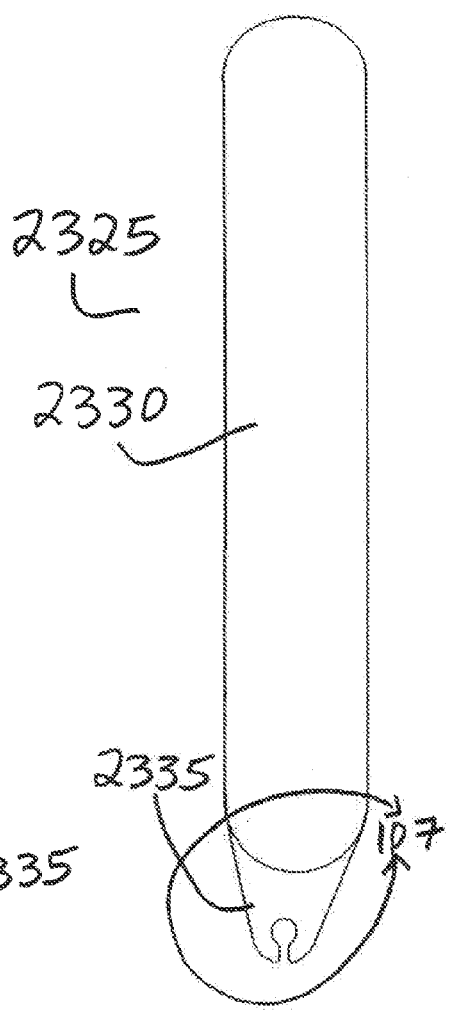
Figure 107:
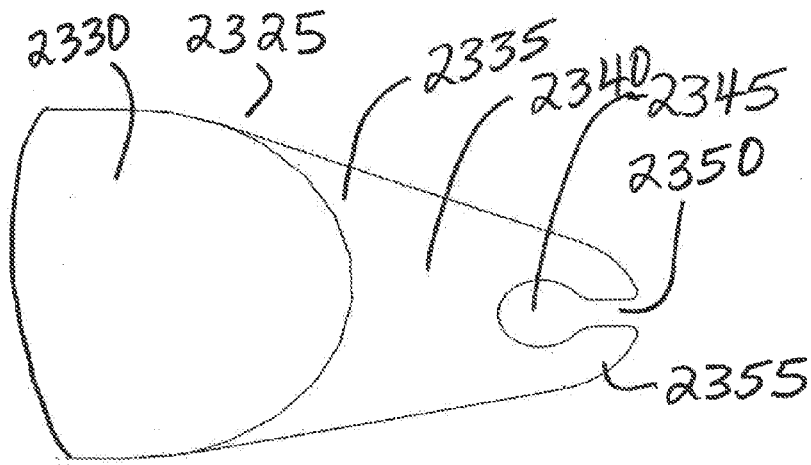

Referring to FIGS. 93 and 94, a coupler 2230 includes a stem 2235 and petals 2240. Like the petals 2240, the stem 2235 includes multiple inner clips 2245 and outer clips 2250. The petals 2240 are used to mount a bypass vessel 2255, such as a synthetic or natural vascular graft, to the coupler 2230. As illustrated in FIG. 94, one of the inner clips 2245 or the outer clips 2250 are positioned on the inside lumen of the bypass vessel 2255 and the other of the inner clips 2245 and outer clips 2250 are positioned on the outside of the lumen. Like the coupler 2125, the coupler 2230 has an angle of between approximately 80 degrees and 100 degrees, and more particularly, approximately 90 degrees.

As illustrated in FIG. 93, the coupler 2230 includes a wall section 2260 in the stem 2235 between adjacent outer clips 2250. The wall section 2260 extends to the petals 2240. The wall section 2260 can be removed to provide additional flexibility in the stem 2235 so that stem can be compressed to reduce its profile. However, like the coupler 2125, the coupler 2230 includes a slit 2260 through the stem 2235 such that the profile of the stem can be reduced when the coupler 2230 is being implanted. The slit 2260 can be longitudinal or, as illustrated in FIGS. 93 and 94, formed as a partial spiral around its circumference.

Referring to FIGS. 95–98, a coupler 2275 is similar to the coupler 2125 with respect to the slots 2160 in the stem 2130 and the inner clips 2165 and the outer clips 2170 in the petals 2135. However, a primary difference between the coupler 2125 and the coupler 2275 is the angle formed between the stem 2130 and the petals 2135. In particular, whereas the angle formed within the coupler 2125 is between approximately 80 degrees and 100 degrees, the angle formed within the coupler 2275 is between approximately 35 degrees and 55 degrees, and more particularly, approximately 45 degrees. Like the coupler 2125, the coupler 2275 includes a slot 2155 that passes through the stem 2130 such that the profile of the stem can be reduced. The slot 2155 is illustrated as being positioned in the front region of the stem 2130 in FIG. 98 for illustrative purposes. Similarly, the slot 2155 is illustrated as being in the rear of the stem 2130 in FIGS. 97 and 98 for illustrative purposes. Of course, it is intended that the slot 2155 can be positioned in any region of the stem 2130 in so much as the profile of the stem can be reduced.

Referring to FIGS. 99–102, like the coupler 2275, a coupler 2300 includes the stem 2130 and the petals 2135. However, unlike the coupler 2275, the coupler 2300 includes an extended section 2305 between the stem 2130 and the petals. The extended section 2305 is defined as a section that extends perpendicularly from the petals 2135 and joins the stem 2135 such that the stem forms an angle with the extended section. The angle between the stem and the extended section 2305 is between approximately 35 degrees and 55 degrees, and more particularly, approximately 45 degrees. The inventors believe that one advantage of the extended section 2305 is a reduced amount turbulence in the blood that flows into the vascular coupler 2300. The coupler 2300 also includes the slot 2155 positioned in the front of the coupler. Of course, the slot 2155 can be formed in various other positions within the stem 2130 and extended section 2305.

Figures 108A, 108B:
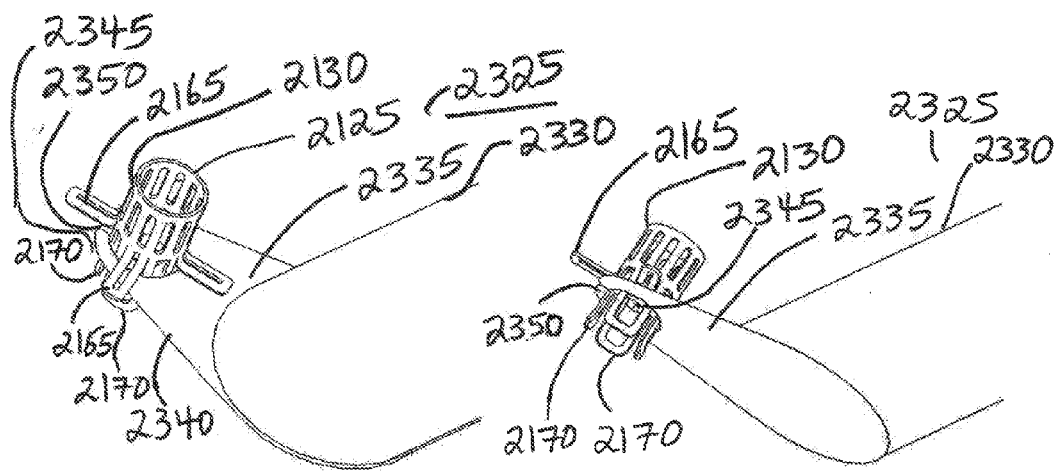
Figures 109, 110:
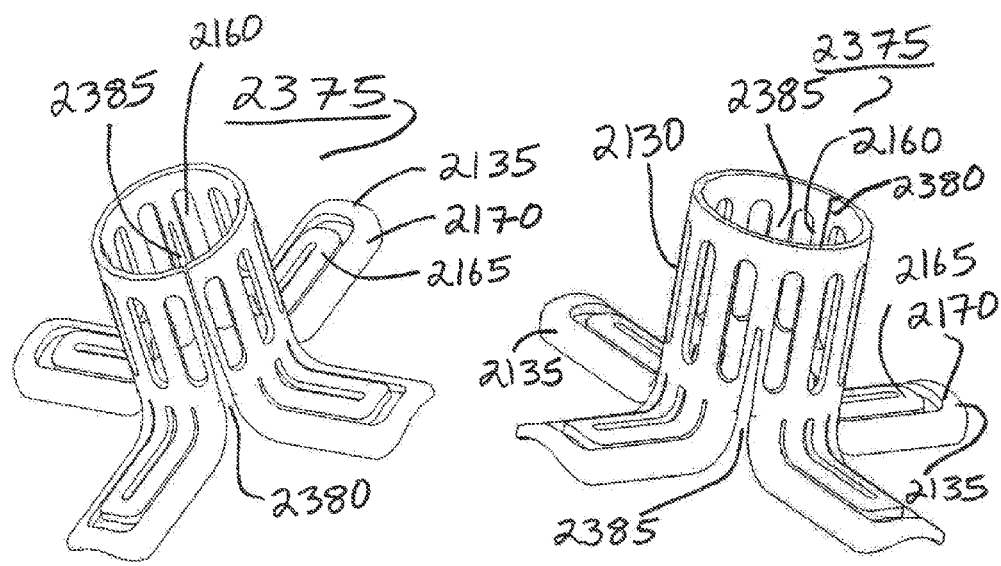
Figure 111:
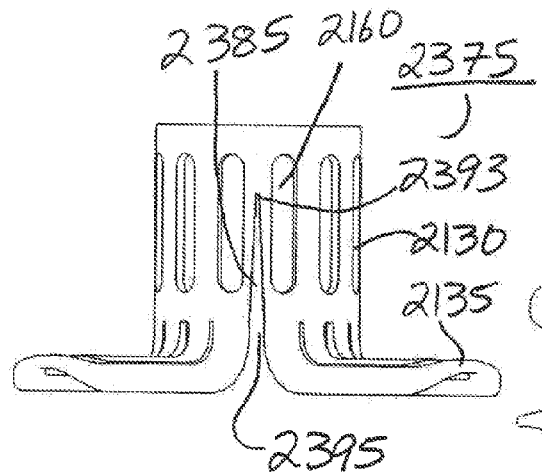
Figure 112:
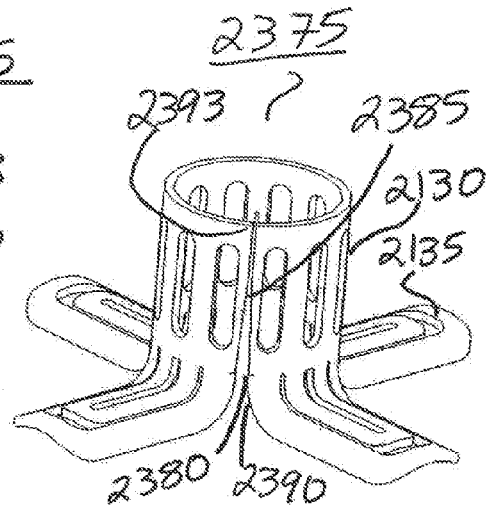
Figure 113:
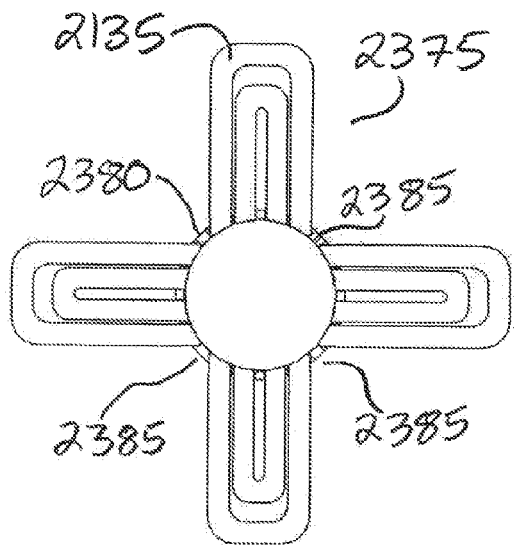
Figure 114:
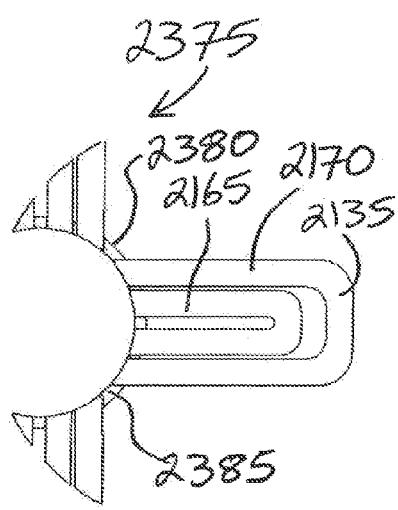
Figure 115:
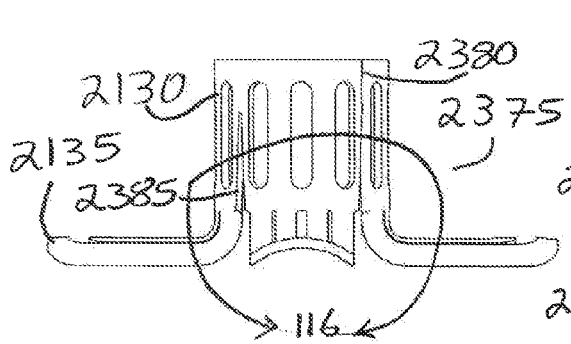
Figure 116:
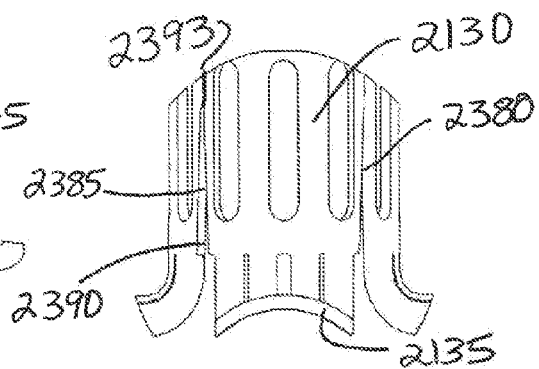
Figures 117, 118:
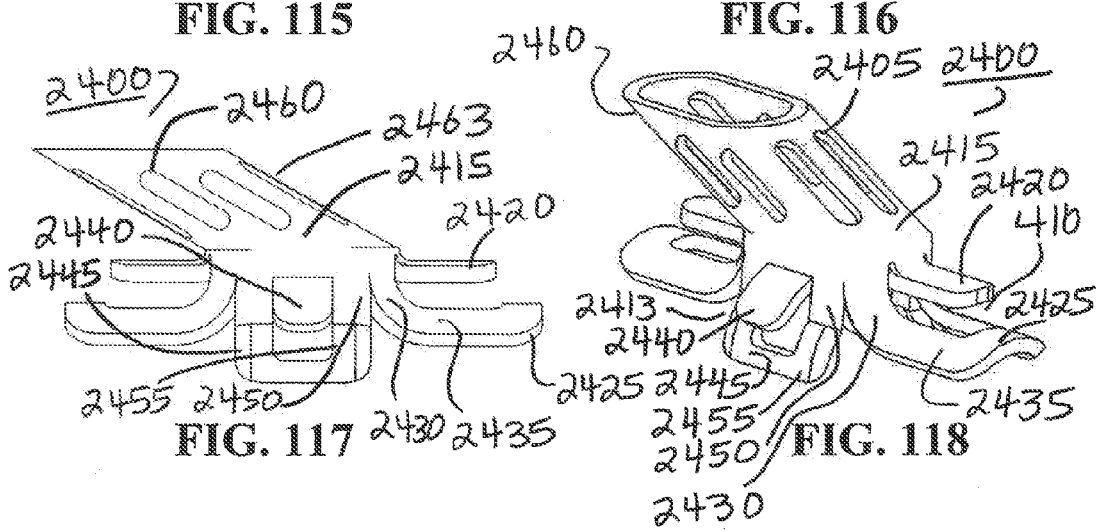
FIGS. 117 and 118 are side and perspective views of a flat-sided vascular coupler.
Figure 119:
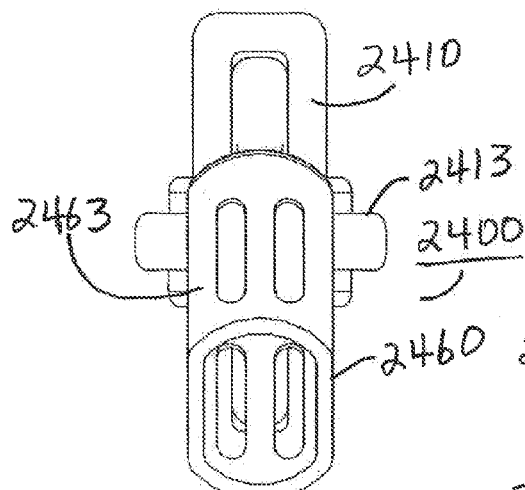
FIG. 119 is a top view of the flat-sided vascular coupler of FIG. 117.
Figure 120:
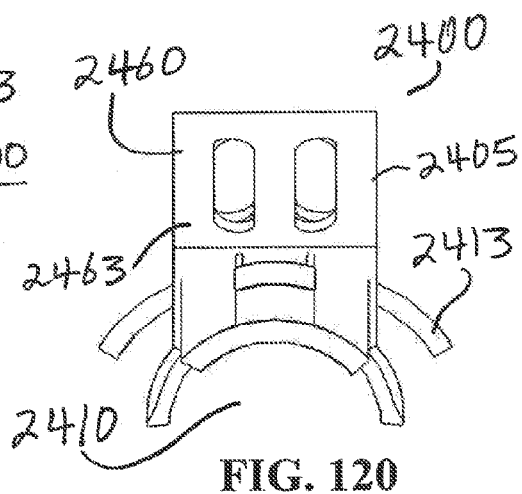
FIG. 120 is a front view of the flat-sided vascular coupler of FIG. 117.

Referring to FIGS. 103–107, a deployment tool 2325 having similarities to the deployment tools described above includes a handle 2330 and a coupler holder 2335 positioned at the distal end of the handle. The holder 2335 includes a plate 2340 through which a channel 2345 passes. A slot 2350 passes from an exterior edge 2355 of the plate 2340 to the channel 2345. Any of the vascular couplers described herein can be delivered and deployed using the deployment tool 2325. In particular, as further illustrated in FIGS. 108a and 108b, the vascular coupler 2125 is held within the channel 2345 with the outer clips 2170 being deflected inwardly by the inner edges of the channel 2345. The plate 2340 and the external petals 2165 additionally can function as depth stops to prevent the physician from inserting the vascular coupler too deeply into the vessel by pressing against tissue surface.

To deploy the coupler 2125, the physician simply uses one hand to hold the coupler while removing the deployment tool from around the coupler, through the slot 2350, which removes the compressive force on the outer clips 2170 such that the clips are released within the lumen of the vessel. The outer clips 2170 expand in the direction of the inner vessel wall. Because the inner clips 2165 are in contact with the outer vessel wall, when the outer clips 2170 expand against the inner vessel wall, the vessel wall will be secured between the clips 2165 and 2170. In this manner, the coupler 2125 and attached bypass graft (not shown) will be securely attached to the vessel. Of course, whether necessary or not, the physician can use stay sutures to additionally ensure that the coupler 2125 will remain secured to the vessel.

Of course, the vascular couplers described herein also can be deployed using a hand held retractor, hemostat, tweezers, or other similar device, including those described above.

Referring to FIGS. 109–116, like the vascular couplers described above, and in particular the vascular coupler 2125, a vascular coupler 2375 includes a stem 2130 and petals 2135. However, unlike the vascular coupler 2125, the vascular coupler 2375 includes a V-shaped slot 2380 that runs the length of the stem 2130 and one or more V-shaped slots 2385 that run a part of the length of the stem 2130. As noted, the slots 2380 and 2385 differ in their length along the stem 2130. Otherwise, they are very similar. For example, the slots 2380, 2385 can be formed by using a laser to cut the slots; with the slot 2385 not being cut the entire length of the stem whereas the slot 2380 is cut the entire length of the stem. The V-shaped slots have a wider distal end 2390 and a narrower proximal end 2393. This configuration of the slots 2380, 2385 allows the physician to even further reduce the profile of the coupler in the region of the wider distal end 2390 of the slot.

Although the vascular coupler 2375 is illustrated as having the slots 2380 and 2385, a vascular coupler can be formed with either or both of the types of slots, and/or one or more of the slots 2385. For example, a vascular coupler can be formed with four slots 2385 such that the coupler can have its profile maximally reduced at the interface between the petals and the stem. Similarly, a vascular coupler can be formed with the slot 2380 and no slots 2385, or the slot 2380 and, for example, one slot 2385.

In general, the vascular couplers 2125, 2230, 2275, 2300, and 2325 are configured for deployment in a vessel, such as the aorta. The angles between the stem and petals described above, i.e., approximately 35 degrees to 55 degrees and approximately 80 degrees to 100 degrees, may be selected based on considerations, such as fluid dynamics and the flow path of the blood between the blood supplying vessel (e.g., the aorta) and the bypassed vessel (e.g., a coronary artery). A vascular coupler placed in the coronary artery has a generally smaller angle formed between the stem and the petals of the coupler, although there may be some overlap in the range of acceptable angles. For example, typically, that angle is between approximately 20 degrees and 45 degrees, and more particularly, approximately 30 degrees. Vascular couplers for the coronary arteries are described next.

Referring to FIGS. 117–120, a vascular coupler 2400 includes a stem 2405 and one or more longitudinal petals 2410 that extend from a base 2415 of the stem in a longitudinal direction and one or more lateral petals 2413 that extend from the base 2415 of the stem in a lateral direction. Each longitudinal petal 2410 includes an inner clip 2420 and an outer clip 2425. Like the vascular couplers described above, one of the clips 2420 and 2425 is placed on the inside of the blood vessel against the luminal wall and the other of the clips 2420 and 2425 is placed on the outside of the blood vessel against the vessel's outer wall. The outer clips 2425 are configured such that they include a first section 2430 and a second section 2435 that is generally perpendicular to the first section. The length of the first section 2430 is selected to approximate the thickness of the vessel wall through which it passes and against the inner surface of which the second section 2435 is placed. The angle formed between the stem 2405 and the longitudinal petals 2410 is between approximately 20 degrees and 45 degrees and, more particularly, approximately 30 degrees.

The lateral petals 2413 each include an inner clip 2440 and an outer clip 2445. The inner clip 2440 is configured to be placed around the outer coronary artery wall of the coronary artery in which the vascular coupler 2400 is implanted. In particular, the inner clip 2440 may be configured to have a radius of curvature that is similar to that of the outer diameter of the coronary artery wall. Similarly, the outer clip 2445 is configured to be placed inside the coronary artery and engage the wall of the lumen of the coronary artery. As such, the outer clip 2445 has a radius of curvature that approximates that of the inner diameter of the coronary artery. The outer clips 2445 are configured such that they include a first section 2450 and a second section 2455 that it is at an angle to the first section 2450. The length of the first section 2450 is selected to approximate the thickness of the vessel wall through which it passes and against the inner surface of which the second section 2455 is placed.

Differences between the lateral petals 2413 and the longitudinal petals 2410 include the relative length and the relative curvature of the outer clips. For example, the diameter or cross-sectional profile of the stem is close to that of the vessel (e.g., coronary artery) in which the coupler is inserted or mounted. As such, there is more length of the artery to use the petals 2410 to secure the coupler to the vessel than there is width of the artery to use the petals 2413 to secure the coupler to the vessel. Because of these constraints, there is no need to have a radius of curvature of the outer clip 2425 along its length, although there is a need to specify a radius of curvature of the outer clip along its width. In contrast, because there is little width of artery to use to secure the coupler to the vessel, there is an increased need to fabricate the radius of curvature of the outer clip 2445 such that it will engage a substantial amount of the circumference of the inner luminal wall of the artery. The vascular couplers 2125, 2230, 2275, 2300, and 2325 are designed for insertion into the aorta, which has an inner diameter that is significantly greater than that of the stem of the coupler, and, as such, the petals that are aligned with the circumference will have less of a need to be short or have a sharp radius of curvature because the radius of curvature of the inner diameter of the vessel is not as tight as in a coronary artery.

The stem 2405 of the vascular coupler 2400 is formed from flattened or parallel walls 2460 and curved front and rear walls. In contrast, the vascular couplers described above had curved front, rear, and side walls, although they could easily be formed with flattened side walls and curved front and rear walls. The flat sides maximize cross-section area through the lumen of the vascular coupler, with the limitation on the diameter of the coupler being that of the opening into the artery in which the vascular coupler is to be placed. To increase the cross-sectional area of the tube through which blood flows, the inventors have increased the length of the cross-section while leaving the width the same as approximately the width of the opening in the artery. As described below, when the vascular coupler 2400 is implanted in a coronary artery, the vascular coupler advantageously forms a fit that maximizes the cross-sectional area of the entry of the blood into the coronary artery from the vascular coupler. This is believed to advantageously promote hemodynamics and reduce damage to the blood cells as well as the posterior vessel wall (opposite from the site of the anastomosis). By having flattened, extended sides and longer side clips, there is potentially better engagement and securement because there is a greater amount of vessel in contact with the coupler.

Referring to FIGS. 121–124, the vascular coupler 2400 is shown in the process of being implanted (FIG. 121) or already implanted in a coronary artery 2465 (FIGS. 122–124). To implant the vascular coupler 2400, the artery is first prepared by, for example, making a longitudinal cut 2470 along a part of the length of the artery. The physician then places the outer clips 2425 and 2445 in a restrained position by using a restraining force provided by either the physician's finger or a deployment tool, as described above. In this position, the outer clips 2425 and 2445 are inserted straight into the longitudinal cut 2470 (i.e., arteriotomy) and then the physician removes the restraining force, which releases the clips 2425 and 2445 such that they can return to their unrestrained position. In the unrestrained position, the coronary artery wall is positioned between the outer clips 2425 and inner clips 2420, and between the outer clips 2445 and inner clips 2440. As seen in FIG. 121, the length of the flattened side wall 2460 is approximately the length of the slit 2470.

Figures 125, 126:
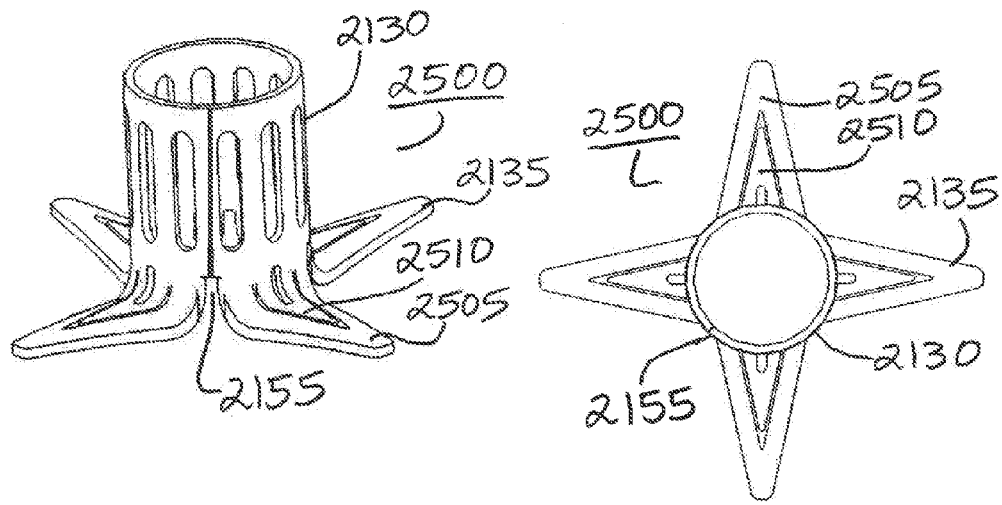
FIG. 125 is a perspective front view of a vascular coupler having V-shaped petals.
FIG. 126 is a top view of the vascular coupler of FIG. 125.
Figures 127, 128:
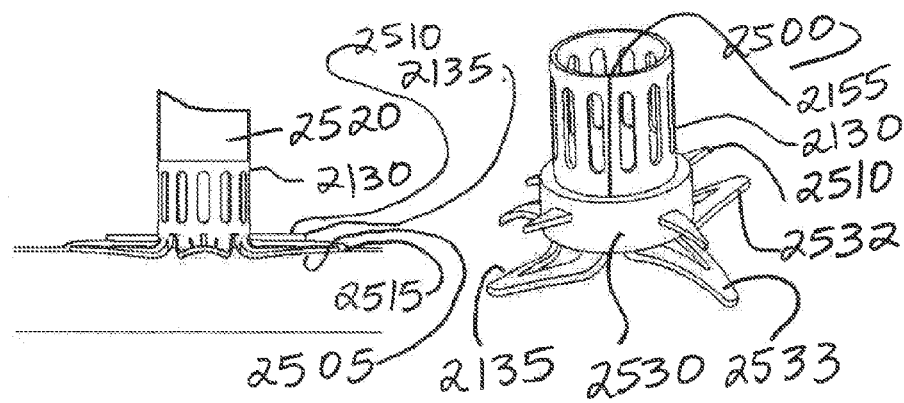
FIG. 127 is a front view of the vascular coupler of FIG. 125 implanted in a vessel.
FIG. 128 is a perspective front view of the vascular coupler of FIG. 125 having a gasket.
Figures 129, 130:
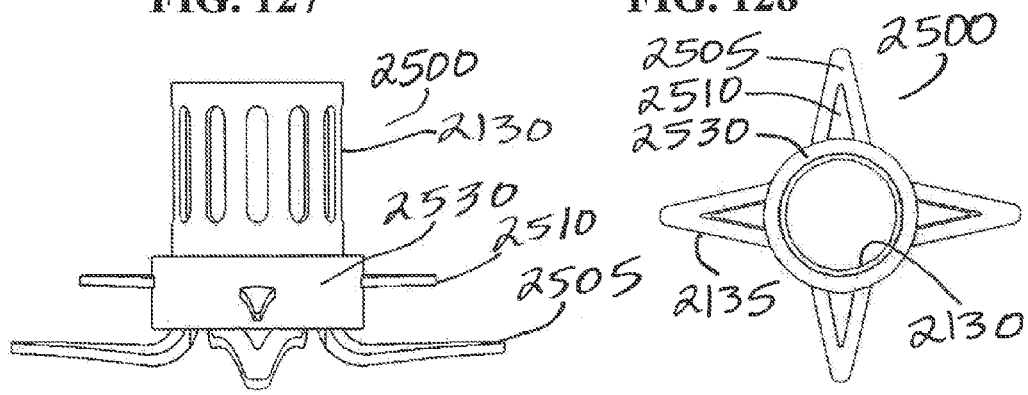
FIG. 129 is a side view of the vascular coupler and gasket of FIG. 128.
FIG. 130 is a top view of the vascular coupler and gasket of FIG. 128.
Figure 131:
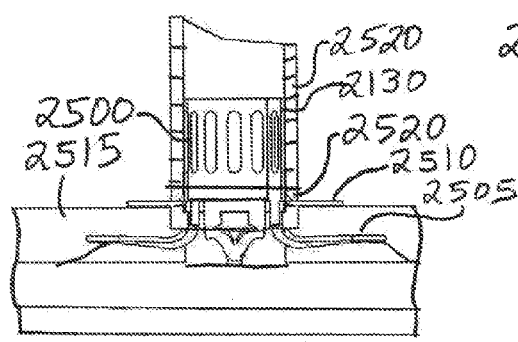
FIG. 131 is a side view of the vascular coupler and gasket of FIG. 128 implanted within a vessel.

Referring to FIGS. 125–127, a vascular coupler 2500 is similar to the vascular coupler 2125 with respect to the stem 2130 and the slot 2155 in the stem. However, the petals 2135 are less rectangular in shape and instead are more V-shaped. Although each petal 2135 includes an outer clip 2505 and an inner clip 2510 like the vascular coupler 2125, the V-shaped configuration reduces the amount of foreign body material within the vessel and in contact with blood. In comparison to the vascular coupler 2400, the vascular coupler 2500 has almost no space along the length of the stem between the outer clip 2505 and the inner clip 2510 when the vascular coupler is deployed. This characteristic can be advantageously used to even more securely retain the vessel wall between the outer clips and the inner clips. The vascular coupler 2500 is shown deployed within a large diameter vessel, such as the aorta 2515, and providing a conduit for shuttling blood into a bypass vessel 2520. Because the diameter of the aorta 2515 is much larger than the diameter of the stem 2130, the opening or slit into the aorta is unlikely to encompass a majority of the diameter of the aorta. As such, the curvature of the outer clips 2505 is less critical and can, in fact, be almost perpendicular to the stem 2130. Of course, depending upon the size of the aorta, or vessel in which the vascular coupler is being deployed, the radius of curvature of the petals can be easily modified to mate with the inner surface of the vessel wall.

Referring to FIGS. 128–131, the vascular coupler 2500 is shown having a compliant gasket 2530 mounted on the stem 2130 between the outer clips and the inner clips. In contrast to the vascular coupler illustrated in FIG. 127, there are two configurations of the outer clips in the vascular coupler of FIGS. 128–131. In particular, the vascular coupler 2500 includes longitudinal outer clips 2532 and lateral outer clips 2533. The longitudinal outer clips 2532 are generally planar to mate with the generally planar surface of the length of the artery whereas the lateral outer clips 2533 are generally curved to mate flush with the generally curved surface of the width of the artery. However, the longitudinal outer clips 2532 are curved across their width to mate with the width of the tissue against which they are deployed. The gasket 2530 advantageously provides a seal between the vascular coupler 2500 and the longitudinal cut 2470. Generally, the gasket 2530 is compliant so that it will conform to the longitudinal cut 2470 and limit excessive blood flow between the longitudinal slit and the gasket. The gasket 2530 can be advantageously configured to cause a separation along the length of the stem 2130 that is similar to the thickness of the vessel in which the vascular coupler is deployed. Of course, the gasket 2530 can be as easily configured such that there is very little separation along the length of the stem 2130 so that there is more pressure on the vessel wall between the inner clip 2510 and the outer clips 2532 and 2533.

The vascular couplers described above, and in particular the vascular couplers illustrated in FIGS. 89–131, are individually described with some of the features and without some of the features. In general, any of the features described above can be implemented on any of the vascular couplers. For example, the longitudinal slot 2155 can be implemented in any and all of the vascular couplers described above. Similarly, the longitudinal slot 2155 does not need to be implemented in any of the vascular couplers.

Figure 132:
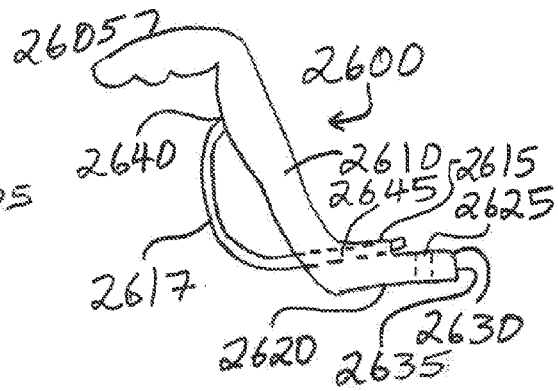
FIG. 132 is a side view of another embodiment of a deployment tool for deploying vascular couplers.

Similarly, although deployment tools have been disclosed, alternative versions of these deployment tools can be used. For example, referring to FIG. 132, a deployment tool 2600 includes a handle 2605, an arm 2610, a coupler holder 2615 positioned at the distal end of the arm, and a pusher tube 2617. The coupler holder 2615 includes a plate 2620 through which a channel 2625 passes. A slot 2630 passes from an exterior edge 2635 of the plate 2620 to the channel 2625. The pusher tube 2617 is connected at a proximal end 2640 to the handle 2605 or arm 2610 and passes through a channel 2645 in the plate 2620. A distal end 2650 extends from the channel 2645 and terminates in proximity to the channel 2625. The pusher tube includes a middle section 2650 between the proximal end 2640 and the distal end 2650. The pusher tube is made of a flexible material, such as a flexible metal or polymer, and by pressing the middle section 2650 in the direction of the arm 2610, the distal end 2650 extends further out of the channel 2645. Any of the vascular couplers described herein can be delivered and deployed using the deployment tool 2600. In particular, a vascular coupler can be held within the channel 2625 with the outer clips being deflected inwardly by the inner edges of the channel 2625.

To deploy a coupler that has been installed in the channel 2625, the physician merely applies pressure on the pusher tube 2617 to urge the coupler through the slot 2630, which removes the compressive force on the outer clips such that the clips are released within the lumen of the vessel. The outer clips expand in the direction of the inner vessel wall. Because the inner clips are in contact with the outer vessel wall, when the outer clips expand against the inner vessel wall, the vessel wall will be secured between the inner and outer clips.

The gasket (e.g., vascular coupler 2500) may be configured to have circumferential grooves that improve acute hemostasis by using the elasticity of the blood vessel to tightly mate within one of the grooves. The grooves and the gasket may be coated with an adhesive, therapeutic agent, and/or other beneficial material.

Figure 133:
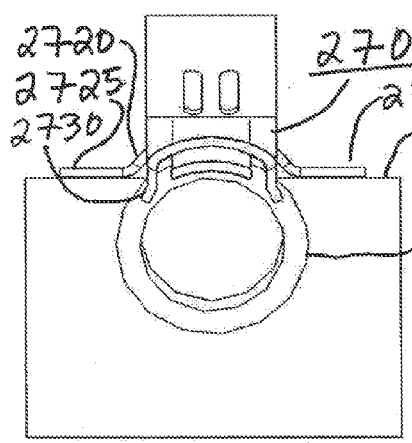
FIG. 133 is a front view of a vascular coupler having longer and wider outer clips deployed in an artery.
Figure 134:
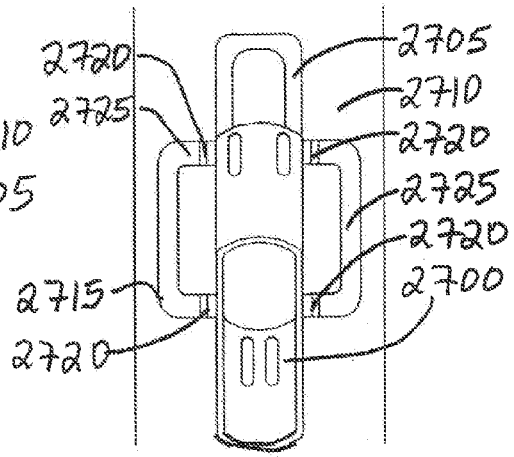
FIG. 134 is a top view of the deployed vascular coupler of FIG. 135.
Figure 135:
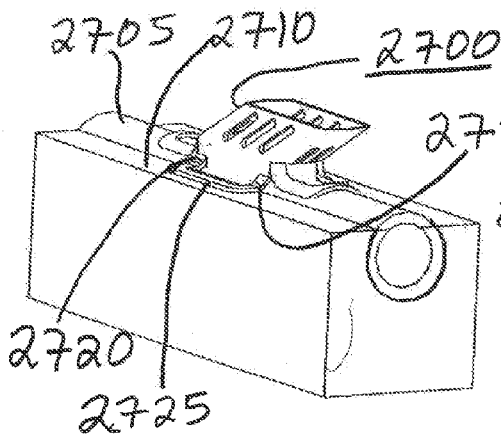
FIG. 135 is a perspective side view of the deployed vascular coupler of FIG. 134.
Figure 136:
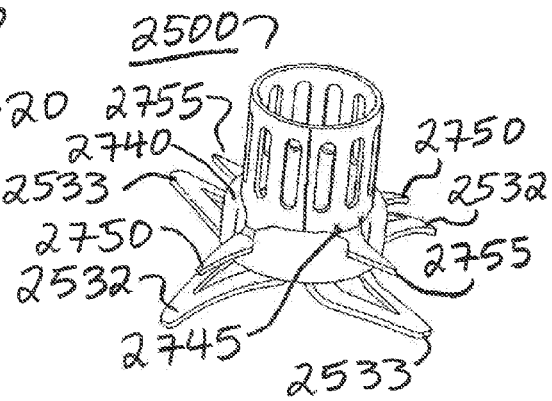
FIG. 136 is a perspective front view of a vascular coupler having a notched gasket.
Figure 137:
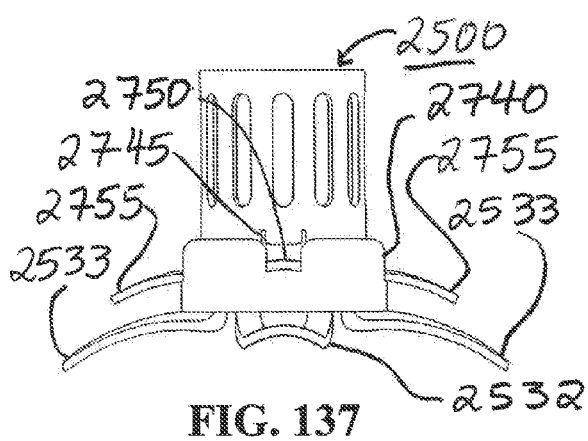
FIG. 137 is a top view of the vascular coupler of FIG. 136.
Figure 138:
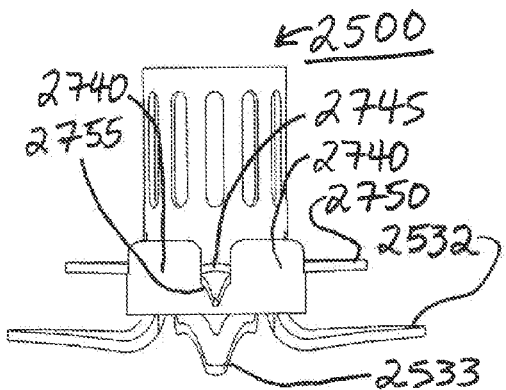
FIGS. 138 and 139 are side views rotated by 90° of the vascular coupler of FIG. 136.
Figure 139:
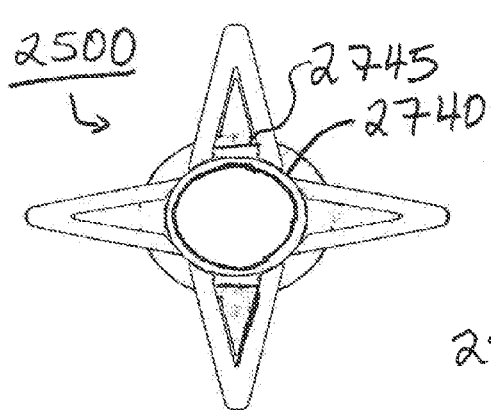
Figure 140:
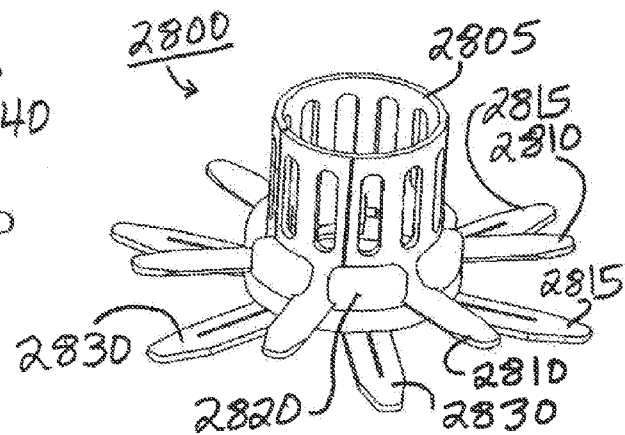
FIG. 140 is a perspective view of a multi-element vascular coupler having a gasket.
Figure 141:
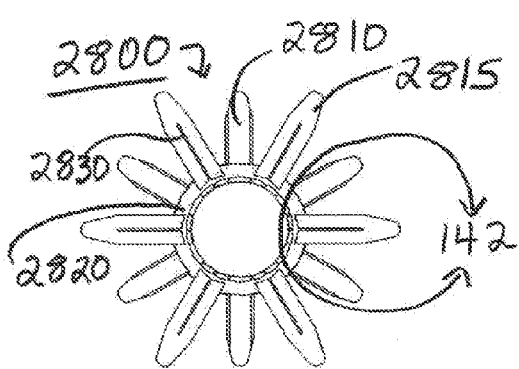
FIG. 141 is a top view of the multi-element vascular coupler of FIG. 140.
Figure 142:
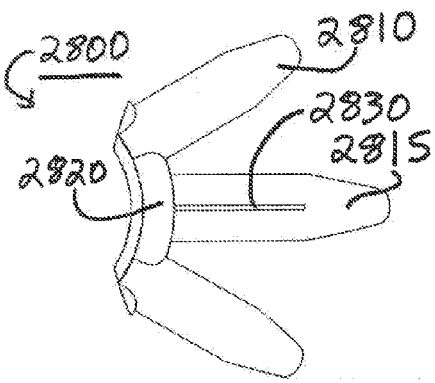
FIG. 142 is a top view of the multi-element vascular coupler of FIG. 140 taken at section line A.
Figure 143:
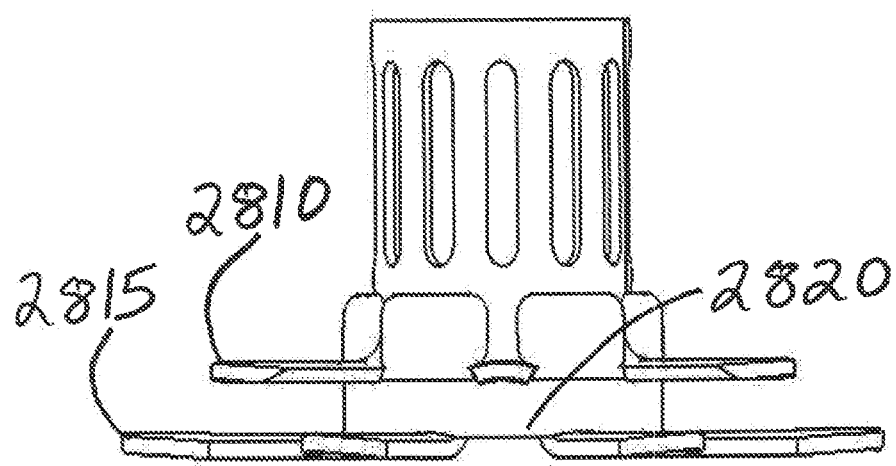
FIG. 143 is a side view of the multi-element vascular coupler of FIG. 140.

Referring to FIGS. 133–135, a vascular coupler 2700 is implanted in a coronary artery 2705. To provide better support of the vascular coupler 2700 against the coronary artery and the epicardial surface 2710, the outer clips 2715 on the side of the vessel are longer and wider than in the vascular couplers described above. In particular, the side outer clips 2715 have a first section 2720 and a second section 2725. The first section 2720 extends from the base of the stem and is selected to have a length and form an angle with the base such that the first section extends to approximately the epicardial surface 2710. The second section 2725 extends from the first section 2720 and is generally flush with the epicardial surface, although it likely will compress the epicardial surface. However, the coronary artery tissue is more compressed by the interaction of the inner clip 2730 and the first section 2720. The use of wider and/or longer outer clips 2715 on the outside of the coronary artery and against the epicardial tissue optionally may be used on any of the vascular coupler described herein.

Referring to FIGS. 136–139, the vascular coupler 2500, described above, is provided with a notched gasket 2740. The gasket 2740 includes longitudinal notches 2745 through which extend the inner clips. The inner clips are shown as having two configurations, longitudinal inner clips 2750 and lateral inner clips 2755. The longitudinal inner clips 2750 have a generally planar surface along its length to mate with the outer surface of the artery. However, the longitudinal inner clips 2750 have a radius of curvature across its width to mate with the radius of curvature of the artery across its width. The lateral inner clips 2755 have a generally curved surface along its length to mate with the outer circumferential surface of the artery. The notches 2745 remove an impediment to the complete deployment of the inner clips 2750 and 2755. The gasket 2740 also can include an upper ridge between adjacent notches to function as an additional aid to hemostasis. The gasket also can include circumferential grooves, as described above.

Referring to FIGS. 140–143, another vascular coupler 2800 includes a stem 2805, multiple upper elements 2810, multiple lower elements 2815, and a compliant gasket 2820. The upper elements 2810 are configured to be placed on the outer surface of a vessel and the lower elements 2815 are configured to be placed on the inside surface of a vessel. The compliant gasket, like the gaskets described above, advantageously covers any potential blood leakage between the recipient vessel and the coupler. The gasket also provides a compliant material to improve acute hemostasis after the coupler has been deployed. The gasket 2820 also can include circumferential grooves to receive the edge of the arteriotomy. The gasket 2820 also can include an adhesive, a therapeutic agent, and/or another beneficial material or agent. The lower elements 2815 include slots 2830 that advantageously remove material from blood and tissue contacting surfaces. In addition, if the slots are made wide enough, a securing suture can be passed through the vessel wall, into the and through the slot 2830, and used to ensure that the vascular coupler 2800 is securely deployed within the artery. The multiple elements 2810 and 2815 advantageously provide attachment of the vascular coupler to the vessel around the entirety of the arteriotomy.

Referring to FIGS. 144–147, a vascular coupler 2900 is configured to connect a first tubular vessel 100 to an aperture in a second tubular vessel 120. For example, the first tubular vessel 100 may be a vascular graft or other bypass vessel and the second tubular vessel 120 may be an artery such as a coronary artery. The coupler includes a tubular conduit 2905 having a proximal end 2910 and a distal end 2915, and one or more pairs of flexible members 2920 extending radially from the distal end 2915 of the tubular conduit 2905. Each pair of flexible members 2920 includes an inner member 2925 and an outer member 2930. The outer member has a first end 2935, a second end 2940, and a length section 2945 extending between the first end 2935 and the second end 2940. The inner member 2925 is completely surrounded by the outer member 2930. The outer member 2930 may be formed as, for example, a U-shaped member. Similarly, the inner member 2925 also may be formed as, for example, a U-shaped member. Of course, referring specifically to FIGS. 145 and 146, either or both of the inner member 2925 and the outer member 2930 may be formed to have a generally straight configuration and, optionally, the other may have a generally U-shape that fits around the other member. The outer member 2930 and the inner member 2925 generally extend radially from the tubular conduit 2910 at a common length position of the tubular conduit.

Referring again to FIG. 144 and FIG. 147, although similarly applicable to the configurations of FIGS. 145 and 146, in use, the distal end 2915 of the tubular conduit 2905 is inserted into the aperture in the second vessel 120 and the inner members 2925 and the outer members 2930 are deployed in the aperture such that the inner members are inside of the second vessel 120 and press against the vessel wall and the outer members are outside of the second vessel and press against the vessel wall.

The coupler 2900 optionally may contain a slot 2950 passing completely through the wall thickness of the tubular conduit and passing between the proximal end 2910 and the distal end 2915. The configuration of the slot 2950 is not limited and may be, for example, straight and along the entire length of the tubular conduit 2905 (FIG. 144), straight and along a portion of the length of the tubular conduit (FIG. 148), spiral-shaped (FIG. 149), or multiple spiral shaped slots 2950 (FIG. 150). The configuration of the slot 2950 is selected so that the cross-sectional profile of the tubular conduit 2905 can be reduced by, for example, being rolled lengthwise (FIG. 151) or otherwise compressed, such as with fingers or surgical tools, so that it can be easily inserted through a small diameter opening. The flexible members may be extended longitudinally to reduce its profile (FIG. 152). Referring to FIG. 148, the slot also can be configured such that it passes through less than the entire length of the tubular conduit 2905. In this manner, a portion of the tubular conduit 2905 can be deformed to reduce the cross-sectional profile of, for example, the distal end 2915. Referring to FIGS. 153 and 154, in one method of implanting the coupler 2900 in which no deployment tools are needed, the physician inserts the distal end of the coupler completely into the arteriotomy such that the inner and outer members are positioned completely within the vessel 120 (FIG. 153). The physician then gently pulls the coupler 2900 out of or away from the vessel until the outer members spring back against the vessel wall, trapping the vessel wall between the inner and outer members (FIG. 154).

Figure 155:
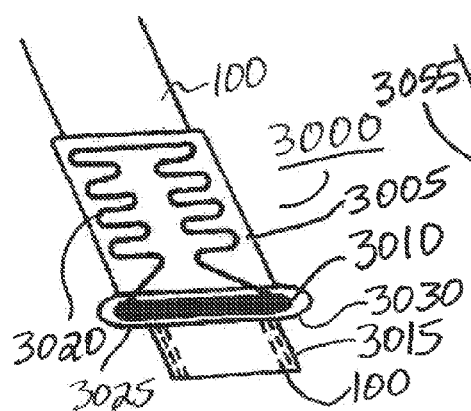
FIGS. 155–162 illustrate various configurations of strain relief members within vascular couplers configured to be placed in a vessel without the use of petals.

Although the vascular couplers described above have been generally described as including petals or other members to assist in the securing the coupler to a vessel arteriotomy, such petals are not strictly necessary. For example, referring to FIG. 155, a vascular coupler 3000 includes an overmolded stem 3005, an overmolded ridge 3010, and an overmolded connecting member 3015. The stem 3005 includes a strain relief 3020 that connects to an elastic or superelastic/shape memory ring 3025 that is positioned within the ridge 3010. The ring 3025 maintains an open lumen through the coupler. The connecting member 3015 is inserted into the arteriotomy and the coupler 3005 is adhered to the vessel 120 using, for example, an adhesive placed on a tissue contacting surface 3030 of the ridge and/or the connecting member 3015. Of course, additional or substitute securing methods can be used to retain the coupler in the host vessel, such as sutures, clips, or other methods known to those of skill in the art.

The primarily metallic vascular couplers described above may be made of a superelastic or shape memory metal or plastic that can be deformed during deployment to have its cross-sectional profile reduced as described above. For example, the stem can be made of Nitinol. The inner and outer surfaces of the stem also or optionally can be electropolished. The inner and outer surfaces of the stem can be configured to have increased biocompatibility and blood compatibility, such as by having a textured surface that promotes endothelial cell growth and adhesion, as described in more detail below.

Materials other than superelastic shape memory alloys may be used as the stem, the inner clips, and/or the outer clips provided they can be elastically deformed within the temperature, stress, and strain parameters required to maximize the elastic restoring force thereby enabling the device recover to a specific diameter and/or geometry once deployed over or on top of the vessel or other location. Such materials include other superelastic metal alloys, spring stainless steel 17-7, other spring metal alloys such as Elgiloy™, Inconel™, superelastic polymers, etc.

The vascular coupler could contain a single or multiple superelastic/shape memory metallic alloy component such as a wire, rod, hoop, tube, coil, sheet, strip, band, or other geometry in the middle, outer, in between, side, horizontal and or vertical plane, or combination on the device. The superelastic/shape memory elements could be located in a single, or multiple plane configuration(s). The thickness could be between 0.005" to 0.040" or other. The superelastic/shape memory alloy material could be annealed in one configuration during manufacture and processed (and packaged) in another configuration. When the material is exposed to normal body temperature (37° C.), will expand to engage the vessel wall, recovering to the optimum size, diameter and geometry to provide acute hemostasis and mechanical securement. Alternatively, a superelastic material could be used, being deformed/deflected during deployment, and designed to recover and provide acute hemostasis and mechanical securement to the vessel.

It is important to understand basic terminology when describing metals with elastic, superelastic, or shape memory behavior. Elasticity is the ability of the metal, under a bending load, for example, to deflect (strain) and not take a permanent "set" when the load (stress) is removed. Common elastic metals can strain to about two percent before they set. Superelastic metals are unique in that they can withstand up to about ten percent strain before taking a set. This is attributed to a "stress-induced" phase change within the metal to allow it to withstand such dramatic levels of strain. This is a desirable feature in anastomosis connection devices. Depending on the composition of the metal, this temperature that allows such a phase change can vary. And if the metal is "set" at one temperature, and then the temperature is changed, the metal can return to an "unset" shape. Then, upon returning to the previous "set" temperature, the shape changes back. This is a "shape memory" effect due to the change in temperature changing the phase within the metal. This summary describes these different metal behaviors, along with the compositions of various shape memory alloys.

When a metal is loaded (stressed) and undergoes, for example, bending, it may deflect (strain) in a "springy" fashion and tend to return to its original shape when the load is removed, or it may tend to "set" and stay in a bent condition. This ability to return to the original shape is a measure of the elasticity or "resilience" of the metal. This ability for a metal to be resilient is desirable for such things as springs, shock absorbing devices, and even wire for orthodontic braces, where the ability to deflect, but not deform (set) is important to maintain an applied force. Thus, elasticity is a highly desirable feature for a flexible, anastomosis device for connecting arterial grafts.

If, under a bending load, the metal takes a set, it is said to have plastically (versus elastically) deformed. This is because the imposed stress, produced by the bending load, has exceeded the "yield strength" (stress) of the metal. Technically, this level of stress that produces a set, is referred to as the "elastic limit", but is about the same as the yield strength. If the applied load increases past the yield strength of the metal, it will produce more plasticity and can eventually break. The higher the yield strength of the metal, the more elastic it is. "good" elastic metals can accommodate up to about two percent strain prior to taking a set. But this is not the only factor governing "elasticity".

Another factor that determines the ability of a metal to deflect to a given, desired amount, but not take a set, is the "elastic modulus", or often called the modulus of elasticity. The "modulus" of the metal is an inherent property. Steels, for example, have a relatively high modulus (30 msi) while the more flexible aluminum has a lower modulus of about 10 msi. The modulus for titanium alloys is generally between 12 and 15 msi.

Resilience is the overall measure of elasticity or "springback ability" of a metal. The ratio of the yield strength divided by the modulus of the metal is the resilience. Although it is one thing for a metal to be resilient, it must also have sufficient strength for the intended service conditions.

As discussed above, when a metal is loaded, each increment of load (stress) produces a given increment of deflection (strain) within the metal. And the metal remains elastic if the applied is below the yield stress. However, there is a unique class of metal alloys that behave in an even more elastic manner. These are the "superelastic" metals, where, for a given applied stress (load) increment, the strain in the metal can reach 5 or 6 percent or more without taking a set. In these type metals, the overall strain required to produce a set can reach an impressive 10 percent. This phenomenon is related to a phase change within the metal, and which is induced by the applied stress. This "stress-induced" phase change can also allow the metal to be set at one temperature and return to another shape at another temperature. This is a "shape memory" effect which is discussed later.

The most common superelastic metal, used in many commercial applications, is an alloy comprised of about equal parts of nickel (Ni) and titanium (Ti), and has a trade name of "Nitinol". It is also referred to as "NiTi". By slightly varying the ratios of the nickel and titanium in Nitinol, the stability of the internal phases in the metal can be changed. Basically, there are two phases. An "austenite" phase and a lower-temperature, "martensite" phase. When the metal is in an austenitic phase condition and is stressed, then a stress-induced martensite forms, resulting in the superelasticity. This is reversible, and the original shape returns upon release of the applied stress.

It is preferred that the Ni-to-Ti ratio in the Nitinol be selected so that the stress-induced martensite forms at ambient temperatures for the case of superelastic brace and support devices, which are used in ambient conditions. The specific composition can be selected to result in the desired temperature for the formation of the martensite phase (Ms)

and the lower temperature (Mf) at which this transformation finishes. Both the Ms and Mf temperatures are below the temperature at which the austenite phase is stable (As and Af). The performance of an anastomosis connecting device can be further enhanced with the use of superelastic materials such as Nitinol. The superelasticity allows for greatly improved collapsibility, during deployment, such as by finger manipulation, with a surgical tool, or utilizing a delivery device or catheter, and which will return to its intended original shape when released within the vessel. The high degree of flexibility is also more compatible with the stiffness of the engaged vessel.

By manipulating the composition of Nitinol, a variety of stress-induced superelastic properties can result, and over a desired, predetermined service temperature range. This allows the metal to behave in a "shape memory" or "shape recovery" fashion. In this regard, the metal is "set" to a predetermined, desired shape at one temperature when in a martensitic condition, and which returns to the original shape when the temperature is returned to the austenitic temperature.

The shape memory phenomena occurs from a reversible crystalline phase change between austenite and the lower-temperature martensite. In addition to this transformation occurring from an induced stress as described previously, it can, of course, also change with temperature variations. This transformation is reversible, but the temperatures at which these phase changes start and finish differ depending on whether it is heated or cooled. This difference is referred to as a hysteresis cycle. This cycle is characterized by the four temperatures mentioned previously, As, Af, Ms, and Mf. Upon heating from a lower-temperature martensite, the transformation to austenite begins at the As, and will be fully austenite at Af. And upon cooling, austenite will begin to transform back to martensite at the Ms temperature, and become fully martensitic at the Mf. Again, the specific composition of the alloy can result in a desired combination of these four transformation temperatures.

In the malleable martensite state, the alloy can be easily deformed (set). Then upon heating back to the austenitic temperature, the alloy will freely recover back to it's original shape. Then if cooled back to the martensitic state, the deformed shape re reform. The typical sequence of utilizing this shape memory property is to set the shape of, for example, a stent or anastomosis coupler, while in the higher-temperature austenitic state. Then, when cooled, deform the martensite material, and then heat to recover the original shape.

With the background given above, it can be seen that, if the Nitinol material requires and exceptionally tight bend, and one that would normally exceed the elastic limit of the material, and thus permanently deform it, a bend can be placed in the device and the device annealed to relieve the bending stresses within the device. Following this first bend, the device can be bent further to produce an even sharper bend, and then re-annealed to alleviate the stress from this additional bending. This process can be repeated to attain the desired, sharp bend or radii that would otherwise permanently deform the device if the bend were attempted in a single bending event. The process for recovery from the position of the most recent bend is then performed as described above.

This shape memory ability is very useful for the delivery and deployment of several types of medical devices, including self-expanding coronary stent devices and anastomotic couplers. These devices are deformed and maintained in their martensitic state (can require a cooling agent if Mf is below room temperature) until they are introduced and released in the body. A warm, sterile solution, short electrical activation, or other suitable means (free recovery if Af is less than 37C) and trigger the recovery to the predetermined shape. Ideally, the material remains austenitic after cooling to body temperature. This is achieved by choosing an alloy composition with a hysteresis such that Ms is never reached upon cooling to normal operating conditions (Ms below body temperature). High-temperature martensite shape memory alloys are also an alternative solution.

Although the example of Nitinol, discussed above, is, by far, the most popular of the superelastic metals, there are other alloys that can also exhibit superelastic or shape memory behavior. These include Copper-40 at % Zinc; Copper-14 wt % Aluminum-4 wt % Nickel; Iron-32 wt % Manganese-6 wt % Silicone; Gold-5 to 50 at % Cadmium; Nickel-36 to 38 at % Aluminum; Iron-25 at % Platinum; Titanium-40 at % Nickel-10 at % Copper; Manganese-5 to 35 at % Copper; and Titanium-49 to 51 at % Nickel (Nitinol).

The unique ability of Nitinol to serve in a superelastic or shape memory capacity, along with the excellent corrosion resistance and biocompatibility afforded this material by the large amount of titanium in the composition, render this alloy ideal for anastomosis connecting devices. Such devices are designed to connect blood vessel segments, including vascular grafts to arteries. This alloy can be expected to allow for improved deflection while being deployed, such as by finger manipulation or by deployment tool, and memory required for the device to return to its intended service shape when released within the blood vessel. Further, this highly elastic alloy can allow for an inherently lower-stiffness design, and thus less mismatch with the elasticity of the engaged blood vessel.

In summary, there are various ways of describing elasticity, but the main criteria is the ability of the metal to return to its initial, pre-loaded shape. Some metals can only deflect a couple percent and remain elastic while others, such as superelastic Nitinol, can deflect up to about ten percent. Nitinol is also biocompatible and corrosion resistant. This unique combination of properties allows a device made of Nitinol, such as an anastomosis connecting device, to be deflected, constrained, and be subsequently released, at a particular site within the vessel, to form its intended service shape.

The vascular couplers formed from a sheet of Nitinol described herein can be formed to have single or multiple layers. To form the vascular coupler, the material is first processed into the desired shape. The device and/or elements (i.e., clips) could then the positioned over a forming fixture. The forming fixture would have one or more surfaces where the device and/or elements would be constrained into the final, as in vivo deployed configuration. The annealing fixture is then partially, or completely subjected to temperatures sufficient to cause the desired effect. The heat source can be an oven, or salt pot. To anneal superelastic/shape memory alloys, the temperature is approximately 300 to 600° C. After a predetermined time, the fixture containing the superelastic/shape memory (SE/SM) alloy elements is then removed from the heat source (such as a salt pot) and quickly quenched in cold water. This process may be repeated as many times as needed to make small incremental changes in the radius, angle or other, during each annealing cycle, to prevent over stressing the material when securing to the fixture. Once the desired final shape has been achieved, and the fixture is cool to the touch, the device and/or elements are removed from the fixture for further processing.

To anneal a thermoplastic polymer, the heat must be above the glass transition (Tg) temperature of the particular polymer. After a predetermined time, the fixture is then removed from the heat source (for this application, an oven) the fixture is removed and allowed to cool gradually. Once the fixture is cool to the touch, the device and/or elements are removed from the fixture for further processing.

The annealing fixture may be made from a metallic material able to withstand the annealing temperatures, and may have single or multiple components or sections. In the case of multiple components or sections, the various components or sections could be held together with clamps, screws, rods combination or other, and may have the ability to anneal devices and/or elements for a single, or multiple devices at one time.

When thermally forming superelastic/shape memory component layer, the superelastic material(s), previously cut into the desired pattern and/or length, are stressed and constrained into the desired resting configuration over a mandrel, or other forming fixture having the desired resting shape of the device depending on the vessel size or other location where the device is intended to be used, and secured. The material is heated to between 300 and 600 degrees (or other) Celsius for a period of time, typically between 30 seconds and 30 minutes, or other. Once the volume of superelastic/shape memory material reaches the desired temperature, the material is quenched by inserting into chilled water or other fluid, or otherwise allowed to return to ambient temperature. As such the superelastic/shape memory component layer(s) are fabricated into their resting configuration. This process may be repeated with the material being annealed in smaller increments of bending or shaping, so as to not stress the material past its elastic limit (approximately 8 to 10%). The superelastic/shape memory layer(s) may be located full or partial length or width of the device.

Any metal or metal alloy that comes in contact with blood and/or tissue can be electropolished. Electropolishing may reduce platelet adhesion causing thrombosis, and encourage endothelization of the exposed metallic areas. Electropolishing also beneficially removes or reduces flash and other artifacts from the fabrication of the device.

The superelastic/shape memory elements could be processed into the desired shape and configuration using several methods, such as electron discharge machining (EDM), laser, chemical etching, grinding, cutting, combination or other, prior to or after the annealing process.

Superelastic/shape memory materials are available in many configurations, from several suppliers, including, NDC (Fremont, Calif.), Memry Corporation (Bethel, Conn.) and Shape Memory Applications, Inc. (San Jose, Calif.).

The vascular coupler also can be partially or completely coated with a polymer coating or covering with a polymer covering, such as, for example, expanded polytetrafluoroethylene, polyurethane, polyethylene terephathalate, or other coating material, as described herein. In general, the coating or covering provides a blood and body compatible surface and also can be used to attach a graft or vessel to the coupler. The covering or coating also provides a surface through which fluid, such as blood, cannot pass, but yet permits the coupler to have its cross-sectional profile reduced. A coating or covering also can be used to reinforce the anasomotic site.

The stem, and or other areas of the substantially metallic version of the device may be annealed in a larger configuration than the vessel (either bypass or host) it will be inserted into, so that once deployed, the larger annealed size could have a greater potential contact force against the host or bypass vessel, than if the device was sized exactly to the vessel.

The stem region may have one or more "hinge" regions that are designed to flex when compressed. The hinge can be an area where the wall is reduced in thickness and or width. The hinged regions may be located so as to assist/enable reduced cross section deployment and or securing the device to either the bypass graft, host vessel, or other. The stem area may be compressed and inserted into the inner diameter (ID) of the bypass vessel. When the stem is no longer compressed, it will expand and engage the inside of the bypass vessel. The outside of the stem may have an adhesive, and or a suture tied around the outside of the bypass vessel. A simple loading tool may be used to compress the stem of the device, or alternatively, hemostats or other common surgical instrument may be used. Alternatively, or in addition, the stem may have a slit or slot to enable reducing the cross section for insertion into the ID of the bypass vessel or other purpose.

If a substantially tubular structure (tube) is used for the device, it may be initially round (concentric), and then processed such that the end shape is an oval, or has two flat sides (flattened), with the top and bottom being substantially round, combination or other.

The host vessel tissue contacting elements that are designed to remain on the outside of the vessel, may be annealed in a different plane than the elements that will be on the inside, to take into account the thickness of the vessel wall.

In loading the vascular coupler into a bypass vessel, the bottom of the coupler may be compressed using a hemostat or other device, to compress the stem region to enable insertion into the end of the bypass vessel. Once inserted into the vessel, the distal ends of the hemostat can be opened, removing the compressive force, allowing the stem to expand radially, making contact with the inside of the vessel. The contact/bond between the device and the bypass vessel may be aided using a biologically acceptable adhesive (contact or other), and or tissue engaging tabs or other that may be biased outward. A suture may also be positioned around the bypass vessel, at the device stem area, providing compression between the vessel and device. For the "paper clip" stem version of the device, the exterior vessel host vessel tissue contacting elements may be deflected outward (to load the vessel to the device) manually, or by using a tool.

Figure 156:
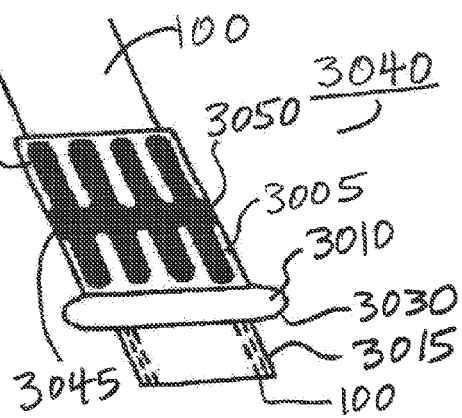
Figure 157:
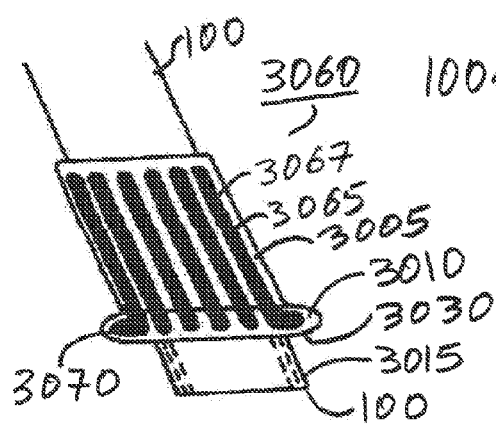
Figure 158:
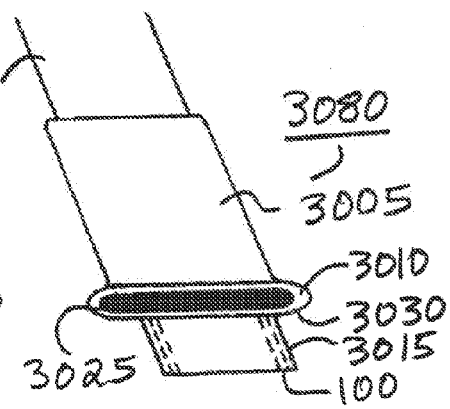
Figure 159:
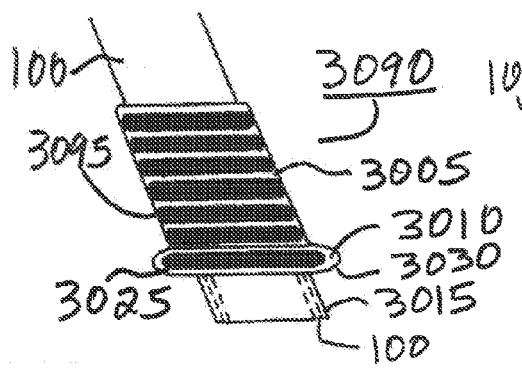
Figure 160:
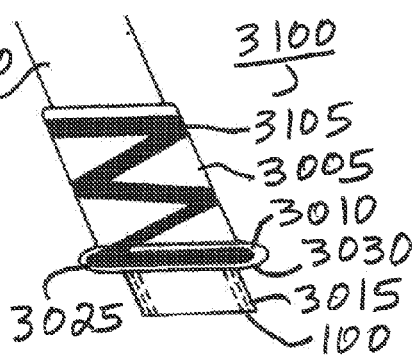
Figure 161:
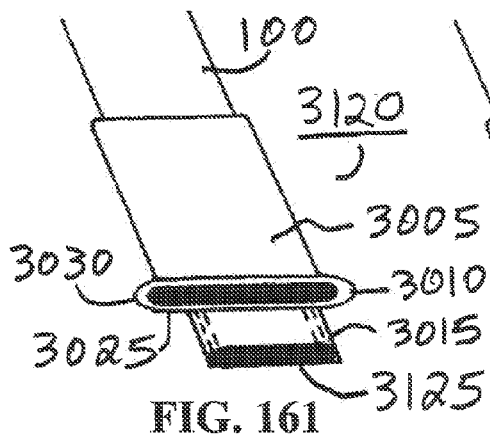
Figure 162:
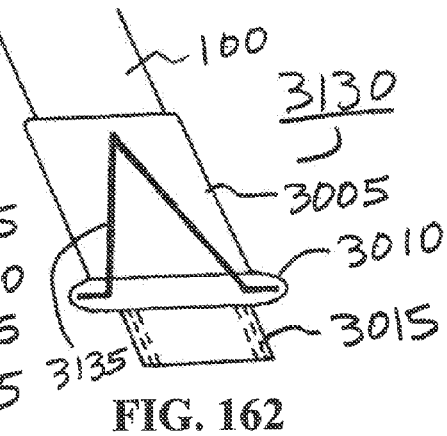
Figure 163:
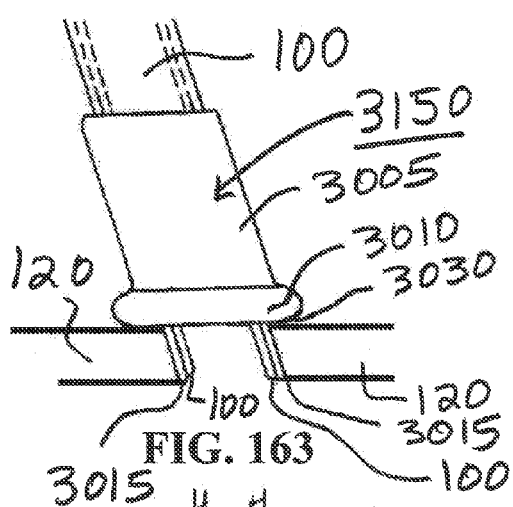
FIG. 163 is a side view of a generic vascular coupler of FIGS. 155–162 implanted in a vessel.
Figure 164:
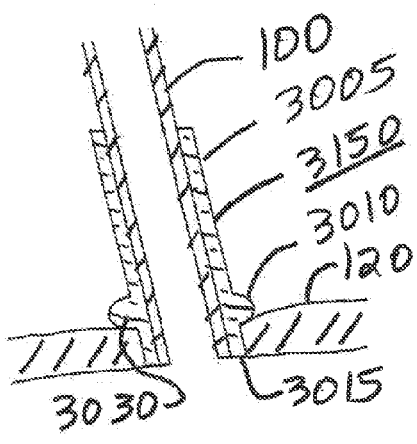
FIGS. 164 and 165 are cross-sectional side and end views of the vascular coupler of FIG. 163 implanted in the vessel.
Figure 165:
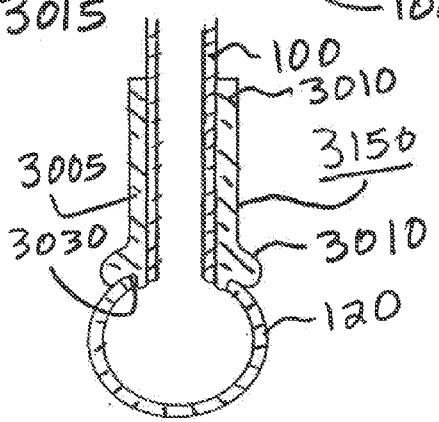
Figure 166:
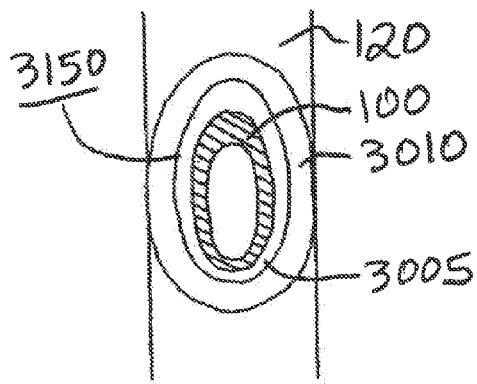
FIG. 166 is a top view of the vascular coupler of FIG. 163 implanted in the vessel.

Referring to FIG. 156, a vascular coupler 3040 is shown that includes a deformable strain relief 3045 in the stem 3005. However, unlike the coupler 3000, the coupler 3040 does not include a ring 3025 in the ridge 3010. The strain relief 3045 has a circumferential portion 3050 and longitudinal members 3055. Referring to FIG. 157, a vascular coupler 3060 includes a longitudinal strain relief 3065 in the stem 3005. However, unlike the strain relief 3045, the strain relief 3065 include longitudinal members 3067 that connect to ridge members 3070 that extend outwardly into the ridge 3010. The ridge members 3070 add support to the ridge. Referring to FIG. 158, a vascular coupler 3080 includes the elastic ring 3025 within the ridge 3010 but does not include a strain relief in the stem 3005. Referring to FIG. 159, a vascular coupler 3090 includes multiple circumferential strain relief members 3095 that are configured to prevent collapse of the lumen of the coupler. The coupler also includes the ring 3025 within the ridge 3010. Referring to FIG. 160, a vascular coupler 3100 includes the ring 3025 and a spiral-spring strain relief member 3105 that extends circumferentially along the length of the stem 3005. Referring to FIG. 161, a vascular coupler 3120 includes the ring 3030 within the ridge 3010 and a reinforcing ring 3125 to ensure that the distal end of the coupler remains open after implantation. Referring to FIG. 162, a vascular coupler 3130 includes a compressible spring 3135 that can be compressed to reduce the profile of the coupler for easing deployment and implantation. Referring to FIGS. 163–166, a vascular coupler 3150 is shown implanted within the vessel 120. The coupler 3150 includes any of the features described above with respect to the coupler 3000, 3040, 3060, 3080, 3090, 3100, 3120, and 3130.

Figures 167, 168:
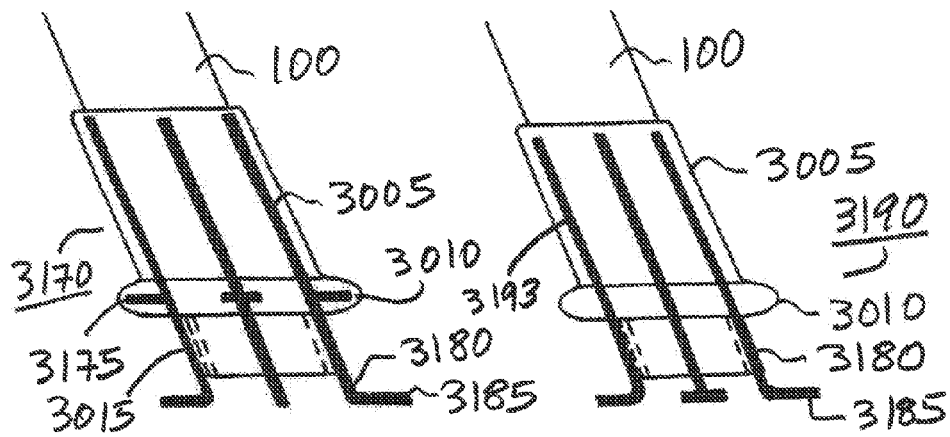
FIGS. 167–175 illustrate various configurations of strain relief members within the vascular couplers of FIGS. 155–162 configured to be placed in a vessel using petals.
Figures 169, 170:
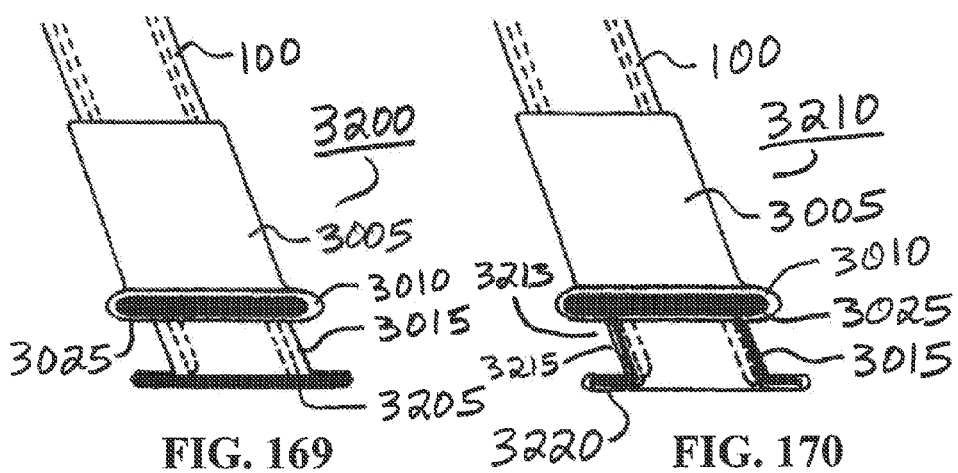
Figures 171, 172:
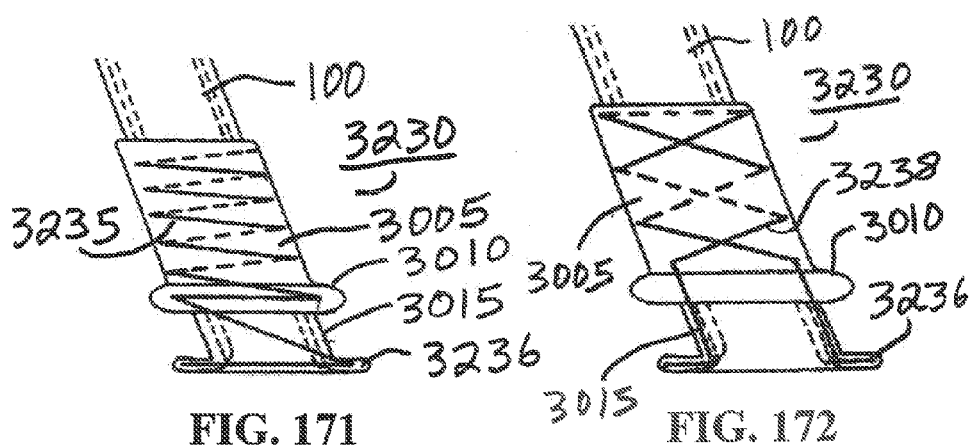
Figures 173, 174:
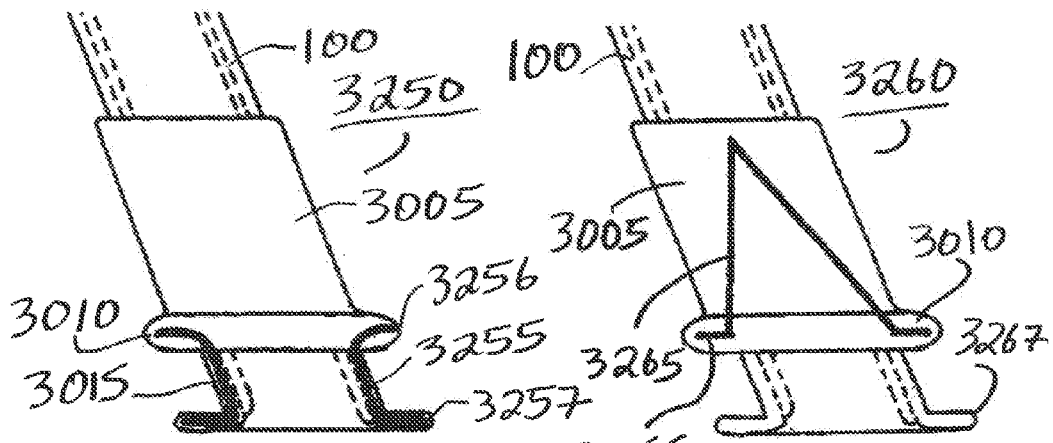
Figures 175, 176:
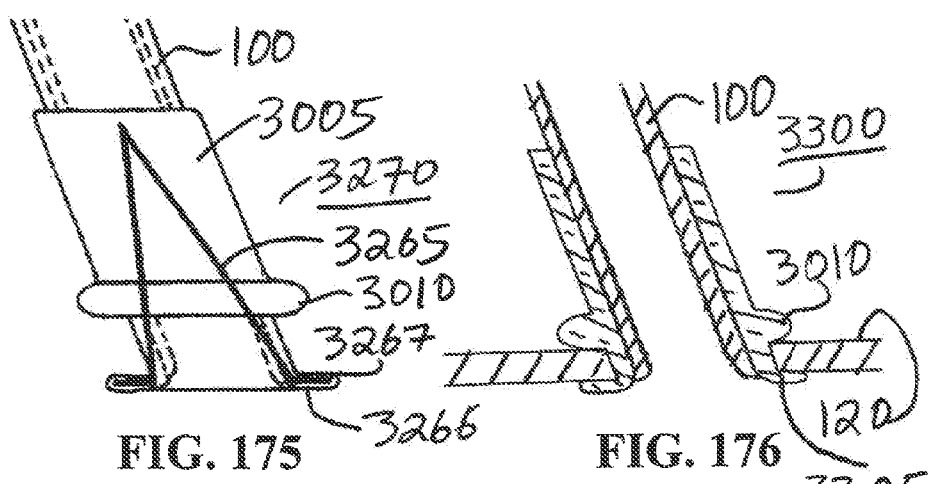
FIG. 176 is a cross-sectional side view of the vascular coupler of FIGS. 167–175 implanted in a vessel.
Figures 177, 178:
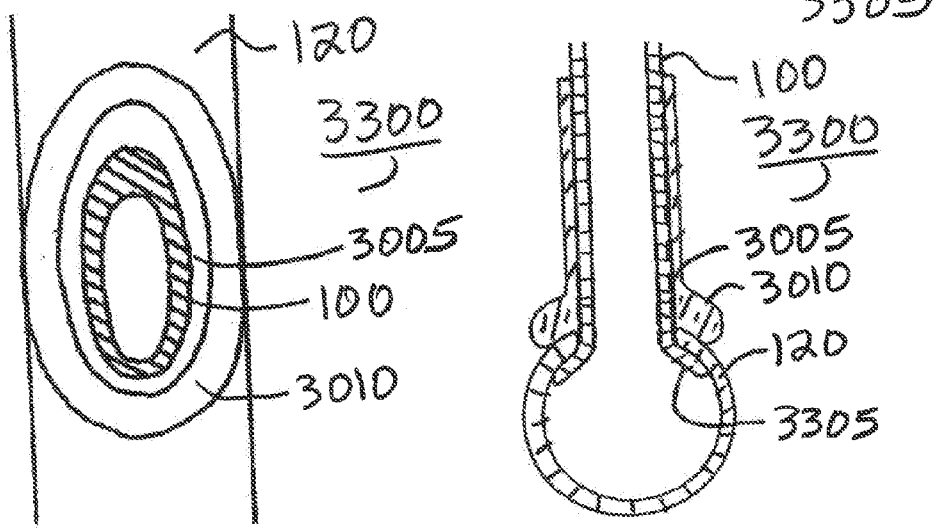
FIG. 177 is a top view of the vascular coupler of FIG. 176 implanted in the vessel.
FIG. 178 is a cross-sectional end view of the vascular coupler of FIG. 176 implanted in the vessel.

Referring to FIG. 167, a vascular coupler 3170 includes strain relief members 3180 that extend along the length of the stem 3005. The strain relief members 3180 include ridge reinforcement members 3175 and petal members 3185. The petal members 3185 and the ridge 3010 trap and retain the vessel 120 when the coupler 3170 is implanted within an arteriotomy. Referring to FIG. 168, a vascular coupler 3190 similarly includes strain relief members 3180. In contrast to the vascular coupler 3170, the strain relief members 3180 do not include the ridge reinforcement members 3175, although they do include the petals 3185. Referring to FIG. 169, a vascular coupler 3200 includes the ring 3025 within the ridge 3010 and a petal ring 3205 at the base of the connecting member 3015. The ring 3025 additionally or alternatively can be configured as a hoop or a band. The petal ring 3205 and the ridge 3010 reinforced with the ring 3025 trap and retain the vessel 120 when the coupler 3170 is implanted within an arteriotomy. Referring to FIG. 170, a vascular coupler 3210 includes the ring 3025 within the ridge 3010 and multiple extended petals 3213 that extend from the ring 3025 and include extensions 3215 and petals 3220. Each petal 3220 extends from an extension 3215. The ring 3025, extensions 3215, and petals 3220 maintain the patency of the coupler and retain the vessel 120 when the coupler is implanted within an arteriotomy. Referring to FIG. 171, a vascular coupler 3230 includes a spiral strain relief 3235 that extends the length of the stem 3005, ridge 3010, and forms petals 3236. Referring to FIG. 172, the vascular coupler 3230 can be configured with a variation of the spiral strain relief 3235 by using a criss-cross strain relief 3238 that terminates in petals 3236, the petals 3235 and strain relief 3238 providing strain relief and preventing collapse of the stem 3005 but providing only strain relief in the connecting section 3015. Referring to FIG. 173, a vascular coupler 3250 includes multiple strain relief/reinforcing members 3255. The members 3255 are generally C-shaped and include a ridge reinforcement segment 3256 and a petal segment 3257. The combination of the ridge reinforcement segment 3256 and the petal segment 3257 retain the coupler 3250 to the vessel 120. Referring to FIG. 174, a vascular coupler 3260 includes a V-shaped compressible spring 3265. The spring 3265 terminates in ridge reinforcement members 3266 that reinforce the ridge 3010. The connecting member includes integral petals 3267 that extend outwardly from the coupler to retain the coupler to the vessel by pinching the vessel wall between the petals 3267 and the reinforced ridge 3010. Referring to FIG. 175, a vascular coupler 3270 includes the compressible spring 3265. However, in contrast to the vascular coupler 3260, the spring 3265 terminates in the integral petals 3267 with the ridge reinforcement members 3266 positioned within the petals 3267. The couplers 3260 and 3270 can be manually deployed by compressing the spring inwardly, inserting the petals into the arteriotomy, and releasing the spring to retain the coupler within the vessel 120. Referring to FIGS. 176–178, a vascular coupler 3300 is shown implanted within the vessel 120. The coupler includes the stem 3005, the ridge 3010, and generic petals 3305. The coupler 3300 includes any of the features described above with respect to the couplers 3170, 3190, 3200, 3210, 3230, 3250, 3260, and 3270. For example, the petals 3305 can be configured as any of the petals of these couplers.

Figure 179:
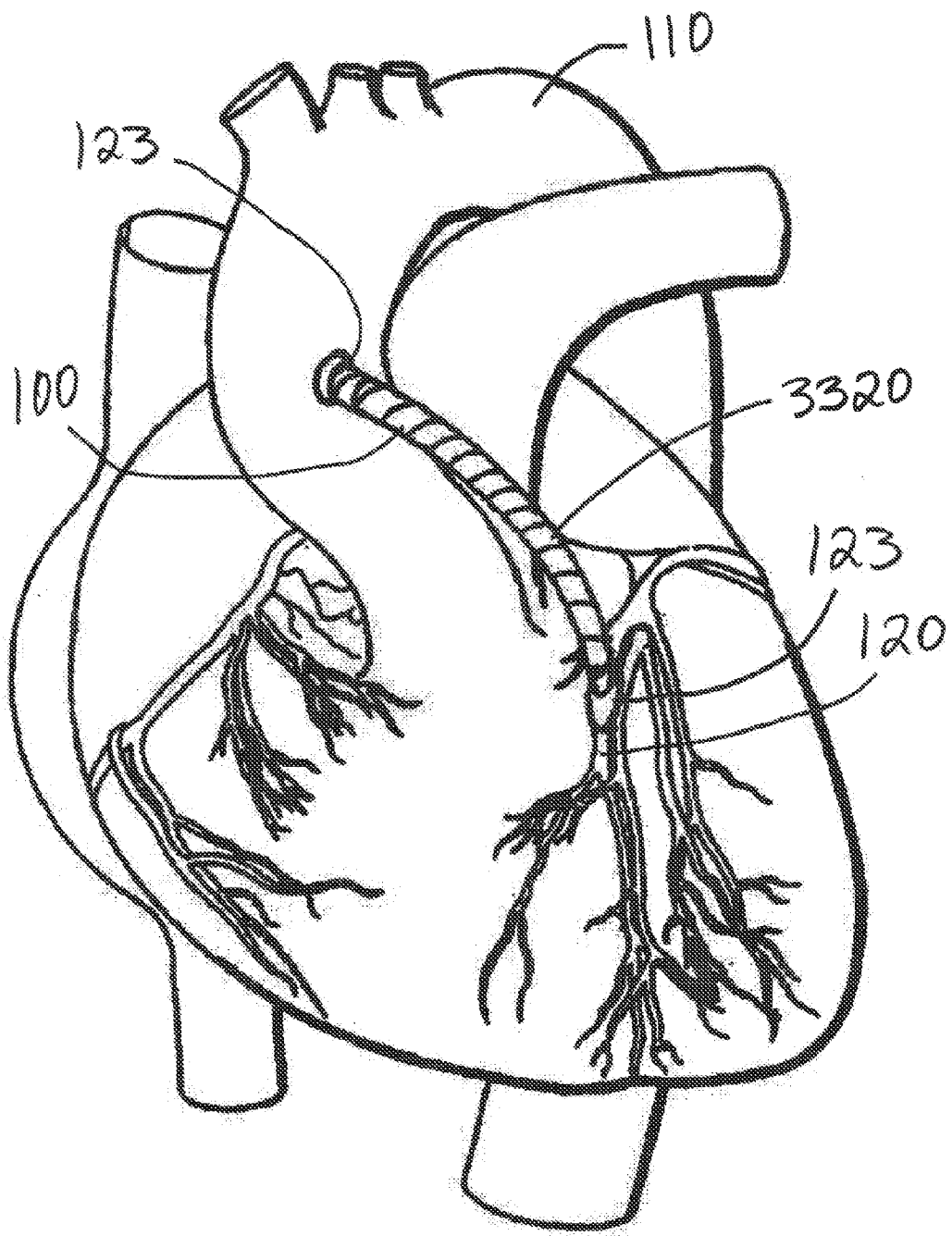
FIGS. 179 and 180 are perspective views of reinforcing members placed around bypass vessels connected to vascular couplers.
Figure 180:
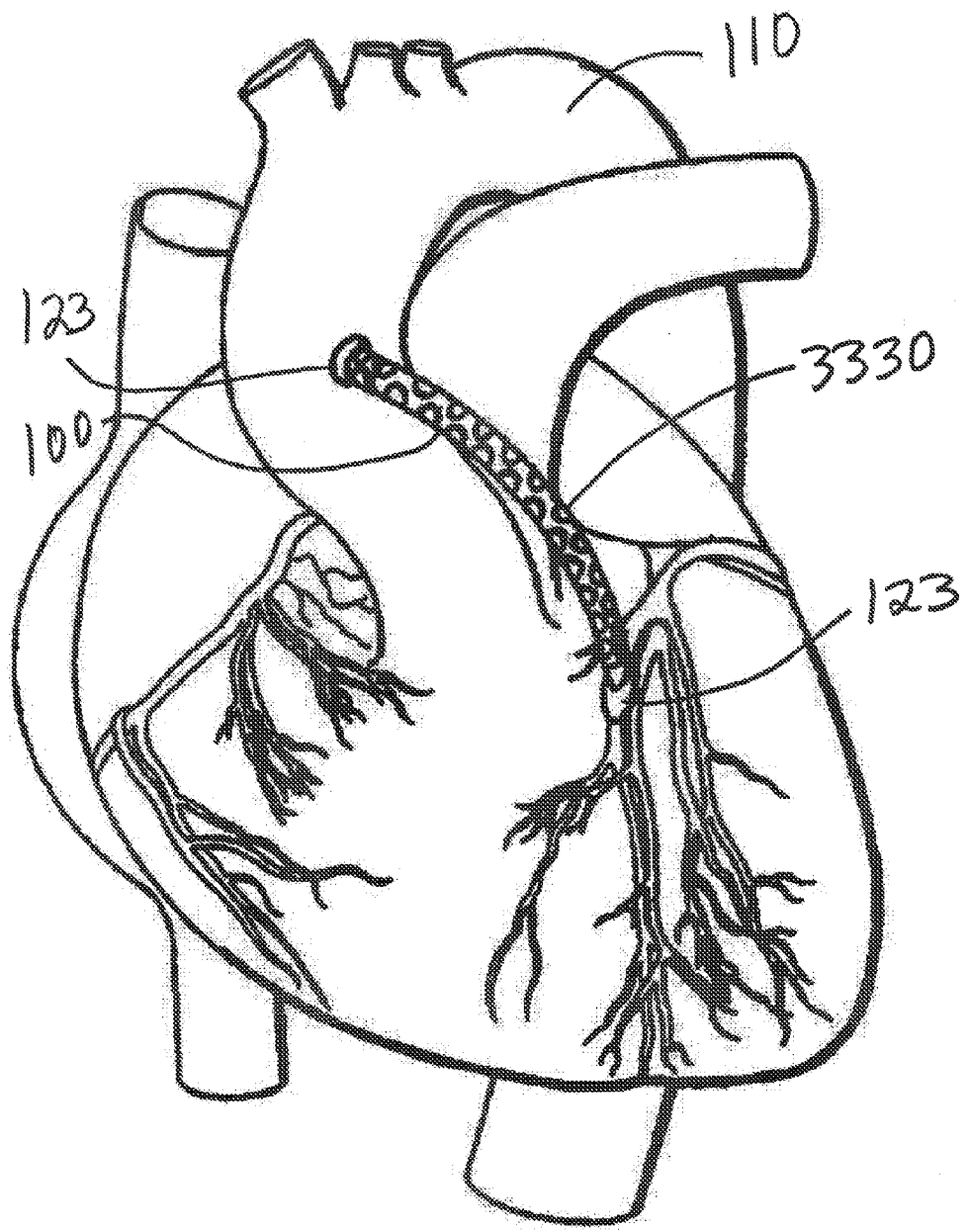
Figure 181:
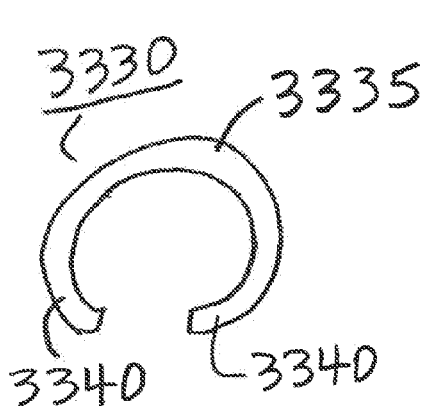
FIGS. 181 and 182 are end and top views of the reinforcing member of FIG. 180.
Figure 182:
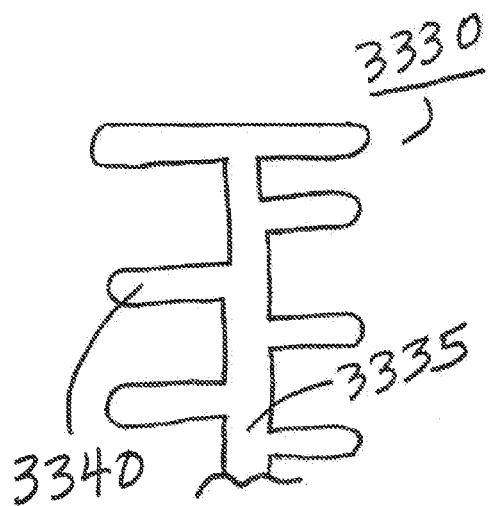

Referring to FIGS. 179–182, the vessel 100 that connects a pair of generic couplers 123 (e.g., any coupler described herein) can be reinforced. FIG. 179 illustrates a spiral-shaped reinforcing member 3320 positioned around the outside of the vessel 100. FIG. 180 illustrates a ribbed reinforcing member 3330 positioned around the outside of the vessel 100. As illustrated in FIGS. 181 and 182, the ribbed reinforcing member 3330 includes a backbone 3335 and alternating ribs 3340 extending from the backbone member. The ribs can be alternating or extending from the rib at the same point along the length of the backbone member.

Figure 183:
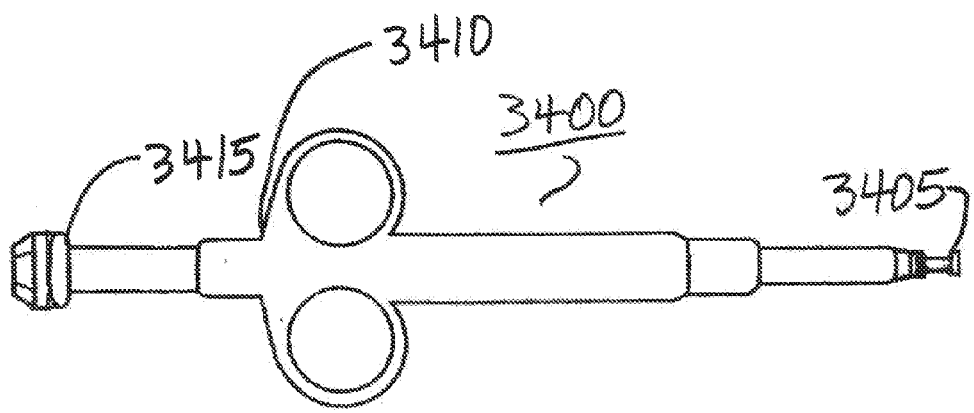
FIG. 183 is a side view of an RF aortic punch.
Figures 184, 185:
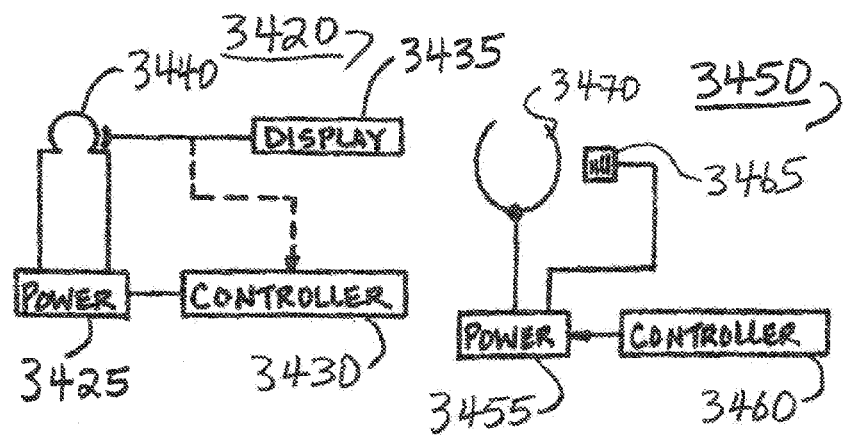
FIGS. 184 and 185 illustrate plan views of directive resistive heating and ohmic tissue heating systems, respectively, for operating the RF aortic punch of FIG. 183.

Referring to FIGS. 183–185, an aid or accessory that can be used with the vascular couplers described herein is an RF aortic punch 3400. The RF aortic punch 3400 includes an electrode tip 3405, a handle 3410, and a cable connector 3415 to provide power to the electrode tip 3405. One example of a suitable RF punch is disclosed in U.S. Pat. No. 60/381,784, titled *RF Tissue Punch, Coring Tool, and Arteriotomy Device and Method* to Houser et al, the contents of which are incorporated herein by reference. The RF aortic punch has a similar design as a standard aortic punch except that one or both of the cutting edges is an electrode. The electrode is used for unipolar or bipolar tissue cutting. The cutting is accomplished using ohmic tissue heating, or direct resistive electrode heating. Referring to FIG. 184, for direct resistive element heating, both conductors 3440 from the power source 3425 are connected to the punch electrode 3405 directly heating the electrode, which has the ability to sever the tissue. Although the electrode is described as a singular electrode, more than one electrode can be used. The direct resistive element heating system includes the power source 3425, the controller 3430, and the display 3435. The use of heat to cut and capture the aortic wall tissue may have benificial and significant clinical benefits by making a more complete circumferential cut through the vessel wall, thereby preventing potential leaking or oozing that can occur with most punches, once the anastomosis has been made. Another advantage is that of the body's natural response to the heat from the RF cutting method.

Referring to FIG. 185, for ohmic tissue heating, one conductor may be connected to an RF power source 3455, through a cable and coupler on the proximal end of the punch, and to the punch electrode 3470. The other conductor is connected to a ground pad 3465 placed on the patient's body, and also connected to the power source 3355 by means of a cable. When the RF power is turned on, and the electrode comes in contact with the vessel wall, the tissue contacting the electrode is heated sufficiently to sever the tissue. The ohmic tissue heating system further includes a controller 3460.

Figure 186:
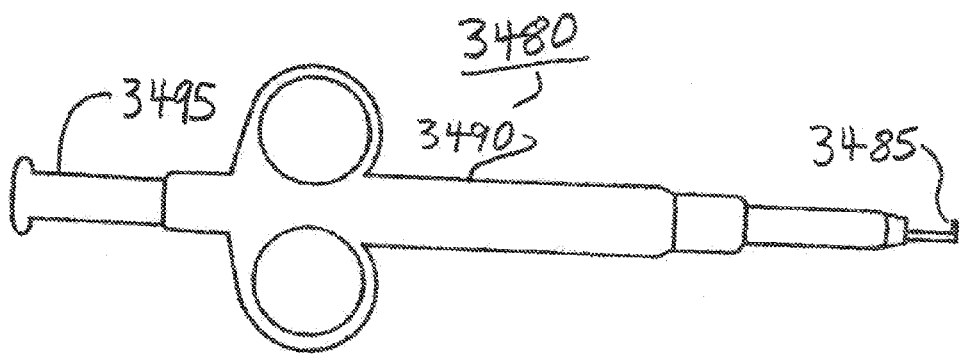
FIG. 186 is a side view of a fixed length arteriotomy device.
Figure 187:
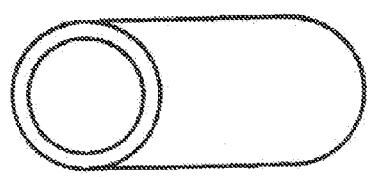
FIGS. 187–189 illustrate the steps in fabricating a side-to-side vascular coupler.

Referring to FIG. 186, another aid or accessory device to use in deploying the vascular couplers described herein is a fixed length arteriotomy device 3480. In general, it is important to match the length of the arteriotomy to the vascular coupler that is to be implanted at the distal coronary anastomosis site. Making the arteriotomy too small will make the insertion of the vascular coupler too difficult. Similarly, making the arteriotomy too long will make acute hemostasis, and mechanical securement, very difficult. As such, advantages arise from providing an automatic arteriotomy device because the surgeon can safely, quickly, and predictably make a specific length cut on a beating heart. The arteriotomy device 3480 includes a cutting element 3485, a handle 3490, and a plunger 3495. Pressing down on the plunger presses and cuts tissue against the cutting element.

Several designs of automatic arteriotomy devices can be used. The designs include: (1) a modified version of the aortic punch that cuts only the vessel wall and does not remove tissue; (2) a specific/specified length Potts type scissors that, for example, has reference length markings on the blade; (3) other scissors or cutting devices having reference length markings; or (4) a scalpel edged device that is advanced through the vessel wall and has a stop to prevent the scalpel blade from advancing too far. These or other devices are used to make a specific length cut through the vessel wall while at the same time preventing posterior vessel perforation. In addition, the automatic arteriotomy device may have one or more electrodes on the cutting surface and uses RF energy to make the cut in a similar manner as the RF aortic punch described above.

Figure 188:
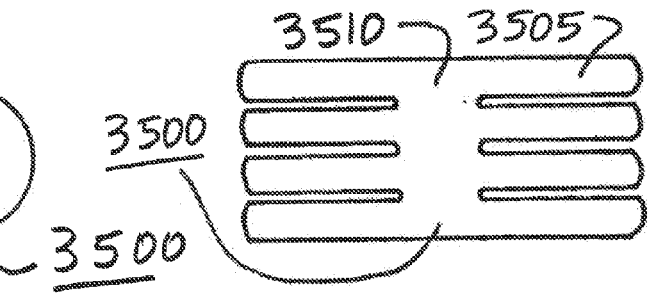
Figure 189:
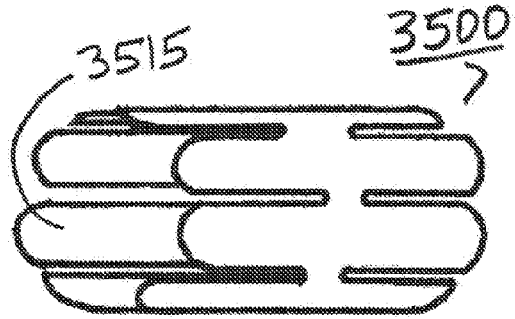
Figure 190:
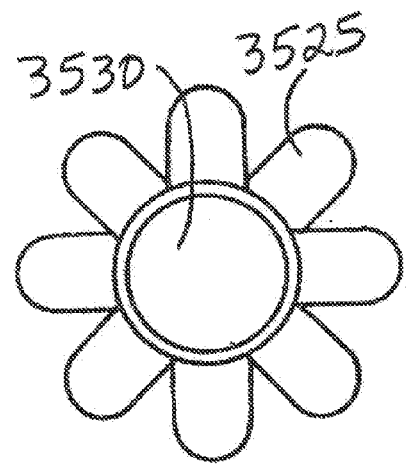
FIGS. 190–192 illustrate adjacent and alternating petal configurations of a side-to-side vascular coupler.
Figure 191:
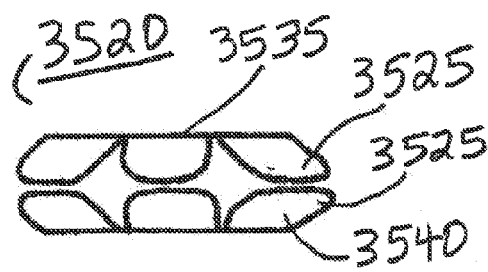
Figure 192:
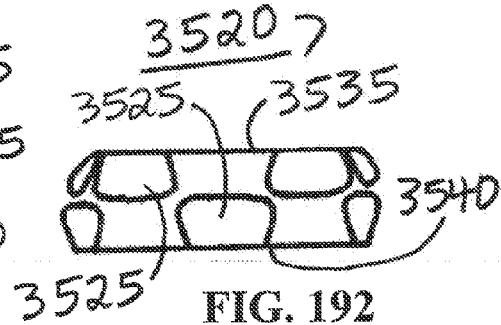

Referring to FIGS. 187–192, a side-to-side vascular coupler is fabricated from a tube 3500. The tube 3500 is machined to form a central ridge or backbone 3510 and lateral ribs 3505 that define a central lumen 3515 (FIGS. 188 and 189). The ribs 3505 then are bent to form a vascular coupler 3520 that includes petals 3525 that extend from a lumen 3530. The coupler includes a first end 3535 and a second end 3540. The side-to-side coupler can have petals that are apposed (FIG. 191) or alternating (FIG. 192).

In one general aspect, the side-to-side vascular coupler is configured as a tubular structure with predominately linear slots (through the wall) on both ends of the tube. The slots do not continue along the full length of the tube, leaving a section (e.g., in the middle) of the tube intact. After further processing, the device has the ability to be constrained into a smaller cross sectional profile during insertion and positioning using a deployment device. Once the deployment device is at the desired location, the constraining force is removed and the side-to-side device reverts to its annealed geometry and profile, engaging and compressing the tissue together, between the end elements. The tissue contacting/engaging elements on one or both ends of the tubular device may be formed to be aligned with each other, or offset, depending on the application.

The purpose of the side-to-side includes providing a conduit, or reinforcement to a conduit for use in cardiovascular, neurological, reproductive, urology, lymphatic, respiratory, or other applications where a conduit or conduit reinforcement is desired. The device may be used completely or partially, outside, inside, in between or combination with any lumen, tubular, duct, organ, hollow body organ or cavity, or other structures within the body. The design and deployment method is especially useful as an endoscopically created gastrojejunal anastomosis.

The vascular coupler may be made of a superelastic/shape memory alloys such as Nitinol, as well as the other materials described herein. The side-to-side vascular coupler may be completely or partially coated with ePTFE and/or other suitable material. The vascular coupler may be coated with other materials to assist with the bonding of the tissue contacting regions, and may include therapeutic materials for acute or chronic elution treatment, as described herein.

In fabricating the vascular coupler, a Nitinol tube is cut to length, linear slots are made through the wall of the tube in the desired geometry using laser machining, wire EDM, etching, photo-etching, a combination of these methods, or other suitable method. The tube is then placed into or on the annealing fixture and annealed into the final, post deployed configuration. Once the heat cycle has been completed, the tube is then quenched in cold water and removed from the fixture. The tube/side-to-side vascular coupler can be further processed if desired. Further processing can include, but is not limited to, electropolishing (i.e., especially desirable if the device will be in contact with blood) and coating (therapeutic or other) or overmolding.

The side-to-side vascular coupler can be deployed with a deployment device such that the vascular coupler is advanced into position and deployed using a catheter or hand held device, specifically designed for the side-to-side device. Modifications of the catheter and hand held deployment devices may be used for endoscopic and laparoscopic procedures. The tip of the deployment device may have a "screw, or corkscrew" type configuration, so that advancement through tissue can occur without significant forward pressure or force being applied—instead, the device can be advanced by rotation of the deployment device.

Referring to FIGS. 193–197, a deployment method for deploying the side-to-side vascular coupler involves a catheter or surgical instrument that has the ability to puncture one or more layers of tissue with the distal tip or through a lumen containing a needle or other sharp pointed device, hold the posterior section of the second layer of tissue against the first tissue layer by the use of one or more guide wire(s) with an acute bend angle (such as 90°), or steering capabilities, or other, while the distal section of the catheter or surgical instrument is advanced to a predetermined location (location determination may be assisted with geometric "bumps", or other on the outside of the catheter or instrument, to allow tactile feedback to confirm that the catheter or instrument is in the correct location for deployment), while the connecting device is allowed to expand and be deployed at the desired location, through the puncture, positioning and compressing the two layers of tissue together, by either the removal of a constraining force (such as a moveable sheath), or the advancement of a plunger stylet, to engage and deploy the connecting device from in between the outside of an inner tube and inside an outer tube catheter or instrument. The catheter or instrument could have multiple full-length lumens that could be used for a variety of purposes, such as sensors (e.g., pressure, tissue contact, electrical, other), or other to assist with the catheter or instrument location, tissue puncturing, visualization, monitor/confirm connecting device deployment, therapeutic fluid or material delivery, or any diagnostic or therapeutic purpose. The catheter or instrument may have steering capabilities, or the use of a steerable guide wire may be used. The steering controls, sensors or other could be operated from the side or proximal end of the catheter or instrument.

Figures 193, 194:
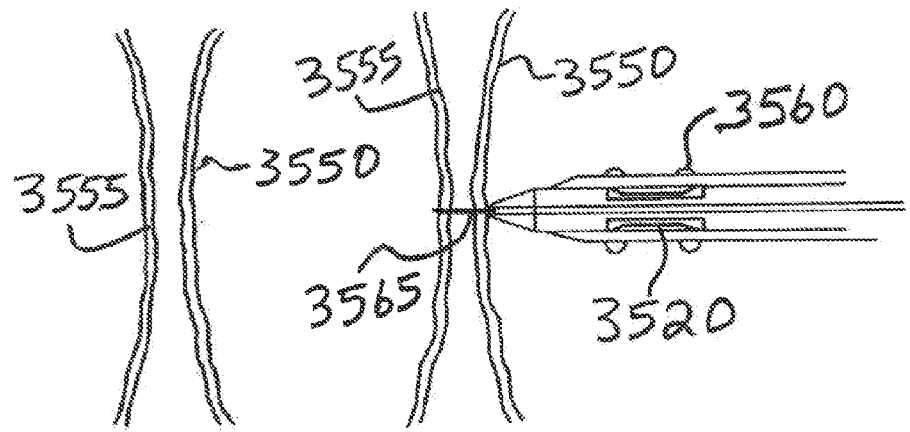
FIGS. 193–197 illustrate the steps of implanting the side-to-side vascular coupler of FIGS. 190–192.
Figures 195, 196:
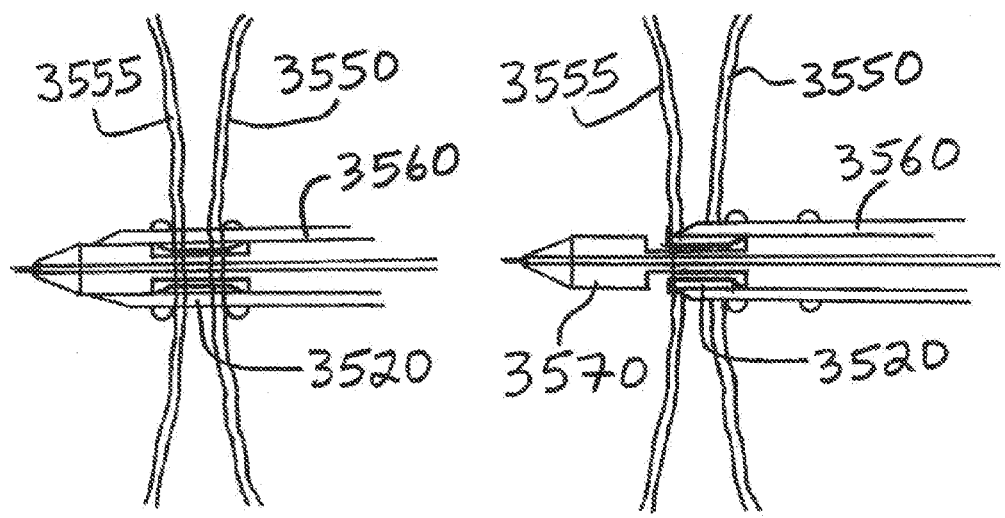
Figure 197:
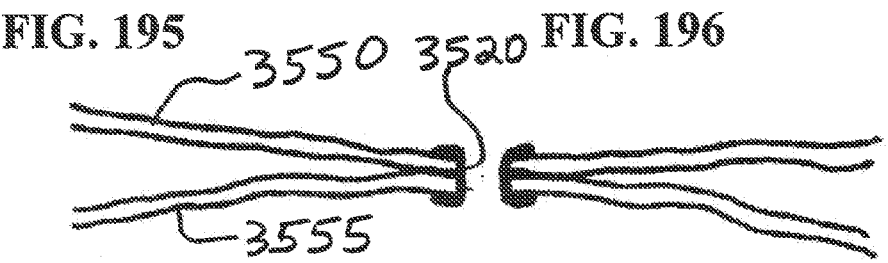
Figure 198:
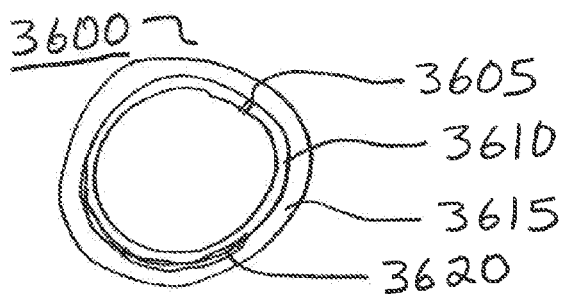
FIGS. 198–202 illustrate the steps in compressing a slotted vascular coupler having partial adherence between the stem and the overmold or coating.
Figure 199:
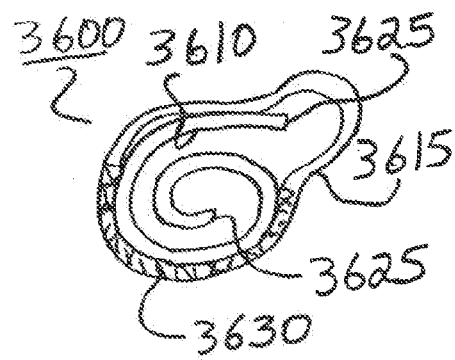
Figure 200:
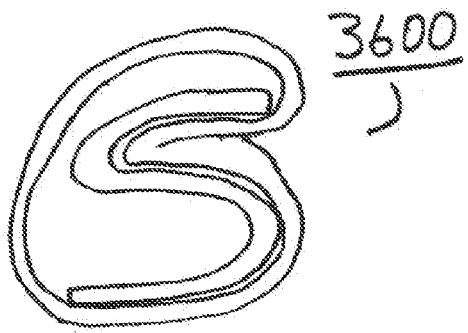

In particular, the side-to-side coupler 3520 can be used to provide a connection between adjacent vessel walls 3550 and 3555 (FIG. 193). Referring to FIG. 194, a sheathed deployment tool 3560 includes a needle 3565. The needle 3565 is advanced through the vessel walls 3550 and 3555 to form openings in the vessel walls. The deployment too 3560 then is advanced through the opening until the coupler 3520 spans the vessel walls 3550 and 3555 (FIG. 195). A distal portion 3570 of the deployment tool 3560 then is extended from the tool (FIG. 196), thereby allowing the coupler 3520 to expand and connect the two vessel walls 3550 and 3555 (FIG. 197).

Figure 201:
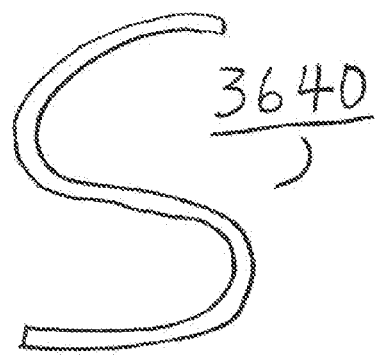
Figure 202:
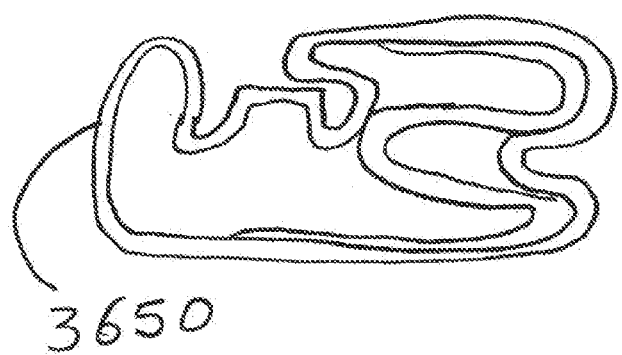
Figure 203:
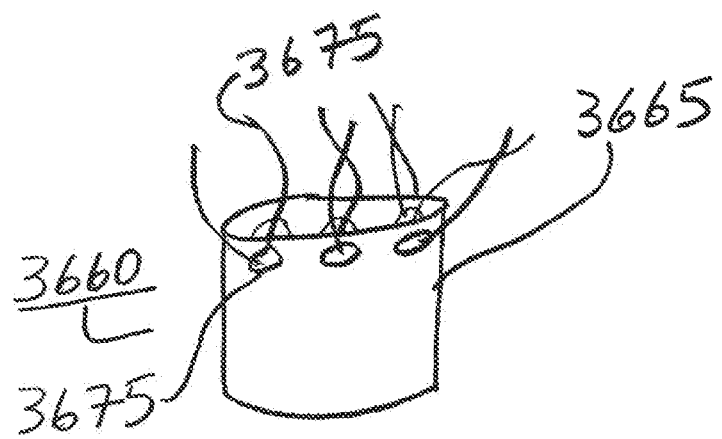
FIG. 203 is a side view of a vascular coupler having suture members for attaching the vascular coupler to a vessel.
Figure 204:
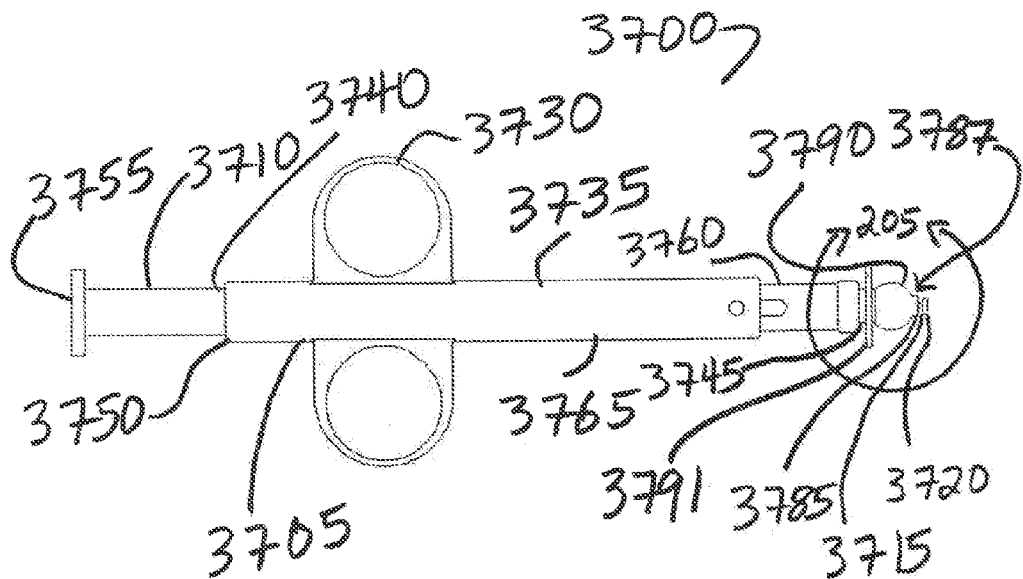
FIGS. 204 and 205 are side and perspective views of an aortic punch.
Figure 205:
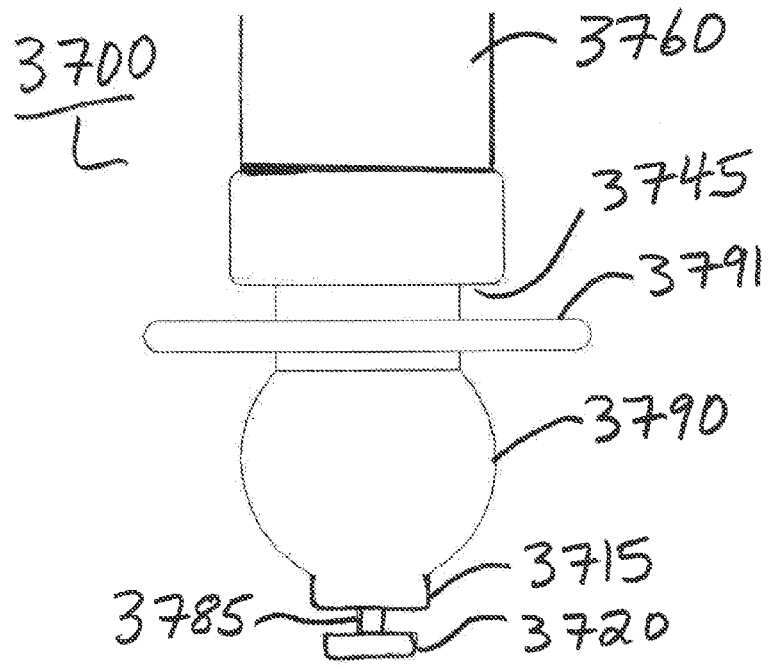

Referring to FIGS. 198–203, a configuration is presented for a low profile coupler 3600. The coupler 3600 includes a stem 3610 having a slot 3605 around which a tube 3615 (e.g., textile material, overmold, etc.) is adhered. However, the entirety of the tube 3615 is not adhered to the stem 3610. As such, a portion of the stem 3610 can be coiled (FIG. 199) or folded (FIG. 200) with a portion of the circumference of the tube unattached and extending away from the stem. The slot 3605 forms slot edges 3625 that are separated away from each other when the coupler is coiled or folded. As illustrated in FIGS. 201 and 202, the stem 3610 can be folded in an S-shape 3640 with the tube 3615 folded into a reduced diameter section 3650. Referring to FIG. 203, a related coupler 3660 can include a stem 3665 that includes preinstalled sutures 3675 passing through the stem and used to attach the coupler 3660 to the vessel. The coupler 3660 can be covered with the tube 3615 or any other overmold or coating described herein.

Referring to FIGS. 204–208, an aid or accessory that can be used in implanting the vascular couplers described herein is an aortic punch 3700 that is used to cut and capture a portion of aorta wall at the desired site of the proximal anastomosis. A commonly used aortic punch is available from Scanlan International (St. Paul, Minn.) as well as from other companies. The tip of the punch is blunt to prevent perforation of the posterior vessel wall. A reduced diameter section of the punch is located just proximal of the distal tip. The punch has an outer tubular shaft that when the punch is actuated, advances over the inner shaft, past the distal tip, cutting and capturing the tissue on the outside of the inner shaft, and inside the outer tubular shaft.

Figure 206:
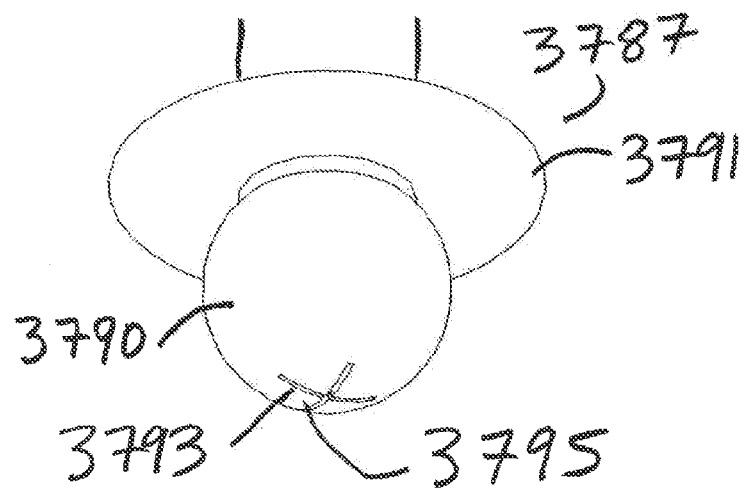
FIGS. 206 and 207 are perspective bottom and top views of an occluder having an occluding ball and occluding stop.
Figure 207:
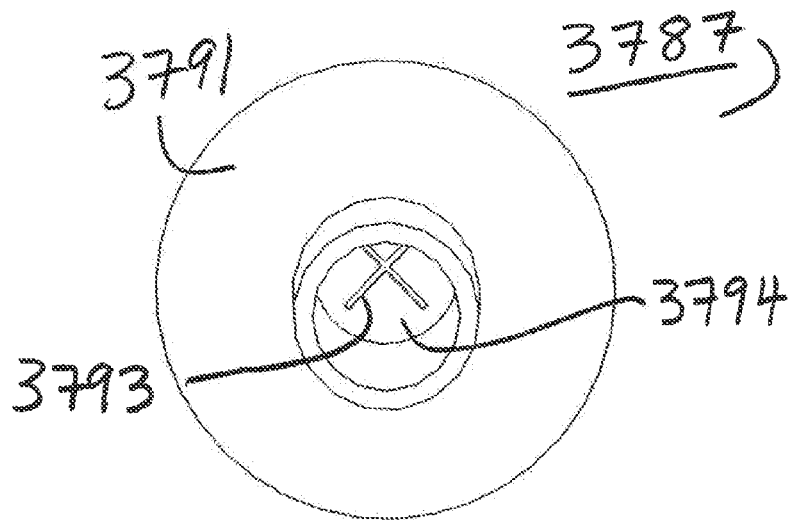

An initial incision using a scalpel blade is made through the aorta, at the site of the proximal anastomosis. The tip of the aortic punch then is inserted into the incision, and the punch is actuated, cutting and capturing a round disc of the wall of the aorta. The vascular coupler then is inserted, and deployed into and through the opening created in the aorta.

place the vascular couplers described herein, an aortotomy typically is formed. To prevent excessive blood loss through the arteriotomy, an occluding device can be used. For example, referring to FIGS. 204 and 205, a tissue punch 3700 includes a handle 3705, a slidable tube 3710, a cutting element 3715, and a cutting disc 3720. The handle 3705 is generally tubular and includes a pair of handles or eyelets 3730 that are integrally mounted to a tube 3735. The tube 3735 has an inner channel 3740 that passes between an open distal end 3745 and an open proximal end 3750. The slidable tube 3710 fits within the channel 3740, includes a proximal end 3755, a distal end 3760, and a tubular segment 3765 passing between the proximal end and the distal end. The cutting element 3715 has a sharp edge 3785 that cuts tissue. Referring also to FIGS. 206 and 207, the punch 3700 also includes an occluder 3787 that includes occluding ball 3790 and an occluding stop 3791. The occluder 3787 is a separate piece that slides onto the distal end of the punch. The occluder 3787 includes a through-channel 3793 that passes between a proximal end 3794 and a distal end 3795. The proximal end 3794 and the distal end 3795 of the channel are configured to reduce fluid flow through the channel when the occluder is inserted into a vessel. For example, the ends can be formed as slits that will fit and slide over the punch 3700 but nonetheless reduce fluid flow through the channel 3793.

In use, occluder 3787 is slidably installed over the distal end of the punch 3700 and the cutting disc 3720 is positioned within a vessel through a small opening in the vessel. Then, the slidable tube 3710 is advanced to advance the cutting element 3715 towards the cutting disc 3720, which cuts tissue positioned between the cutting element and the cutting disc. After the cut is made, the punch is advanced to position the occluding ball 3790 against the opening to prevent excessive bleeding.

The size of the occluding ball 3790 can be of a similar size as the cutting disc to fit against the vessel. The occluding ball 3790 can be fully inserted into the vessel such that the interaction of the occluding stop 3791 rests against the vessel to reduce blood loss. If the ball is positioned within the vessel and the stop is positioned against the vessel wall, the punch can be slidably withdrawn from the occluder and minimal blood leakage results.

The punch 3700 also can be configured to have a power source that heats the cutting element such that the tubular vessel tissue is mechanically cut and thermally cut. The shaft or handle of the punch/coring/arteriotomy device may act as a guide for a localized tissue stabilizer, introducer (splitable or tearable, or with another removable means), occluder, combination of these, or any other device for any desired purpose, before, during, and/or after the cutting process.

Figure 208:
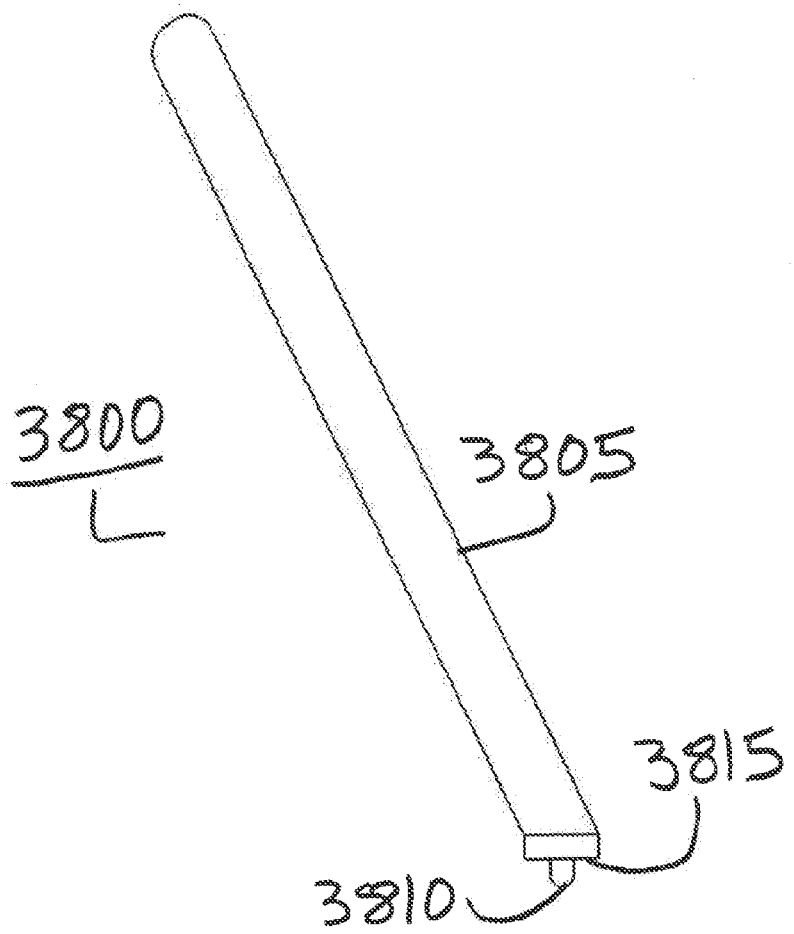
FIG. 208 is a side view of a hand-held occluder that can be used to occlude an opening in a vessel prior to placing a vascular coupler.

Referring to FIG. 208, a hand-held occluder 3800 can be used to occlude an opening in a vessel. The occluder 3800 includes a handle 3805, an occluder ball 3810, and an occluder surface 3815. In use, the punch 3700, or similar device, is used to form an opening in the vessel. To reduce blood loss, the physician quickly inserts the occluder ball 3810 into the opening and rests the occluder surface 3815 against the vessel wall. The physician then removes the occluder 3800 when, for example, a vascular coupler is to be inserted.

The vascular couplers described herein typically are or can be part of a system with various accessories. For example, a vascular coupler can be used with a graft, adhesive materials, therapeutic agents, and radiopaque materials.

The vascular couplers could be used with harvested biological grafts such as the internal mammary artery (IMA), radial artery, saphenous vein, or other. Additionally, grafts made from various other biological materials, or combination of biological and synthetic materials, may also be used. Synthetic vessels include Cardiopass™ from Cardiotech (Woburn, Mass.) and Aria™ from Thoratec (Pleasanton, Calif.), as well as others.

The device could have a biocompatible contact adhesive or other material to bond or secure the device to the vessel, sealing the anastomosis site. In addition, adhesives may be used to secure, or assist in securing the bypass graft to the coupler. The adhesive/bonding compounds/solutions could be added during the manufacturing process, just prior to deployment, or after the device has been deployed. The bonding materials could be in the form of a liquid, semi solid, or solid. Suitable bonding materials include gels, foams and microporous mesh. Suitable adhesives include acrylates, cyanoacrylates, epoxies, fibrin-based adhesives, other biological based adhesives, UV light and/or heat activated or other specialized adhesives. The adhesive could bond on initial contact, or longer, to allow repositioning if desired. The preferred adhesive may be a crystalline polymer that changes from a non-tacky crystalline state to an adhesive gel state when the temperature is raised from room temperature to body temperature. Such material is available under the trade name Intillemer™ adhesive, available from Landec Corp. as well as composites and combinations thereof and combinations of other materials. Suppliers of surgical adhesives include, but aren't limited to, Plasto (Dijon, France), Haemacure (Montreal, Canada), Cohesion (Palo Alto, Calif.), Cryolife (Kennesaw, Ga.), TissueLink (Dover, N.H.), and others. To increase the work time of the adhesive or allow repositioning of the vascular coupler after it has been deployed, the adhesive can be blended with a material, such as a starch or other material, that dissolves and retards or delays bonding to allow repositioning of the coupler after it has been deployed. A degradable coating can be placed over the adhesive coating so that it degrades and exposes the adhesive.

The vascular couplers described herein may be coated with materials such as Parylene or other hydrophilic materials that are biologically inert and reduce surface friction. Another method to reduce surface tension for metallic or metallic alloy couplers or overmolded couplers with metallic or metallic alloy elements or components is to chemically polish or electropolish those surfaces that will come in contact with blood or tissue. Sandblasting, beadblasting or other may be performed prior to polishing. It is believed that chemical polishing or electropolishing reduces platelet adhesion because of the smooth surface that results. Chemical polishing and or electropolishing process can also be used as an effective way to reduce the thickness of metal or metal alloy coupler components.

The coupler device may incorporate one or more coatings, materials, compounds, substances, drugs, therapeutic agents, etc. that positively affect healing at the site, at and or near where the device is deployed, either incorporated into the structure forming the device, incorporated into a coating, or both. Thromboresistance materials, antiproliferative materials, or other coatings intended to prevent thrombosis (acute and or chronic), hyperplasia, platelet aggregation, or other negative response, at or near the attachment of the bypass graft, as well as at or near the implantation site of the coupler through the host vessel. The coatings, materials, compounds, substances, drugs, therapeutic agents, etc. may be used by themselves, and/or contained in a carrier such as a polymeric matrix, starch, or other suitable material or method. The coatings may be liquid, gel, film, uncured, partially cured, cured, combination or other suitable form.

Coatings on the coupler may be used to deliver therapeutic and pharmaceutic agents include (but are not limited to): antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II.sub.b/III.sub.a inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor signal transduction kinase inhibitors. Alternatively, a clot promoter may be used, such as protamine sulphate or calcium hydroxide. Endothelial cells may also be added to the coupler device.

The therapeutic compounds/solutions may be blended with the device base materials during fabrication, applied just prior to deployment, or after the device has been deployed.

The therapeutic materials may be located on, through, inside, or combination of the device in holes, grooves, slots (or other indentations) or designs. For example, the surface under the vessel reinforcement ridge, as well as the under ridge hemostatic gasket may have partial or complete holes grooves, or other indentations, filled with a therapeutic substance, in contact with the host vessel tissue. In addition, the area of the coupler that comes in contact with the bypass vessel may also incorporate this feature. The petals may also have partial or complete holes, slots, grooves, or other filled with a therapeutic substance, or simply coated on the outside surfaces. This design allows direct contact of the therapeutic substance, while maintaining the functional ability of the coupler or coupler component. Combinations of therapeutic substances or coatings may be used on the same coupler. For example, a more viscous (gel or other) therapeutic substance may be used to fill the partial or complete holes (or other) on the vessel reinforcing ridge and hemostatic gasket under the ridge, while the petals are coated with a less viscous (liquid) material. The therapeutic substance may be the same, or a combination of more than one type used on a single coupler. The coatings may be designed to provide benefits acutely, and/or over a period of time. The coatings, materials, compounds, substances, therapeutic agents, etc. may be desired to be static, and/or eluding. The coatings, materials, compounds, substances, therapeutic agents, etc. elutes from the coated (or embedded) device (or component) over time and enters the surrounding tissue. The coatings, materials, compounds, substances, drugs, therapeutic agents, etc. preferably remain on the coupler for at least three days, and up to approximately six months, and more preferably between seven and thirty days.

Post device fabrication coating methods include, but are not limited to, spin coating, RF-plasma polymerization, dipping, spraying, brushing, submerging the devices into a beaker containing a therapeutic solution while inside a vacuum chamber to permeate the device material, etc.

Alternatively, or in combination with the above therapeutic substances, a material such as platinum, gold, tantalum, tin, tin-indium, zirconium, zirconium alloy, zirconium oxide, zirconium nitrate, phosphatidyl-choline, pyrolytic carbon, combination or other material, may be deposited onto the coupler surface using electroplating, sputtering vacuum evaporation, ion assisted beam deposition, vapor deposition, silver doping, boronation techniques, or other coating process.

In addition to the above therapeutic methods and materials, similar and additional methods of coating and materials are described in detail in U.S. Patent Application No. 2002/0133183, the contents of which are incorporated in their entirety by reference.

Radiopaque material such as barium sulfate, bismuth trioxide, tantalum or other can be added to the vascular couplers, reinforcement structure (e.g. the overmold) or bonding material. Additionally, platinum, gold, or other material may be added to the coupler by sputter coating, ion deposition, vapor deposition, combination, or other process.

The vascular couplers described above can be used with various accessories, as necessary, to improve the outcome for the patient receiving the coupler. For example, the bypass graft can be reinforced with a vessel reinforcement device to prevent kinking, collapsing, or other types of restrictions to blood flow. Examples are provided in the figures. Also, the reinforcement device could prevent bypass graft vessel over expansion once blood flow has been reestablished. The reinforcement device can be used with any anastomosis type, such as a coupler, staple, suture, etc. Similarly, the vessel reinforcement device can be used with harvested biological grafts such as the internal mammary artery (IMA), radial artery, saphenous vein, or other. Additionally, the vessel reinforcement device can be used with grafts made from other biological materials, or combinations of biological and synthetic materials.

The vessel reinforcement device may be used on the outside or inside of the bypass graft, and may fabricated with a contact adhesive, as described herein, and or therapeutic material, as also described herein, on the tissue contacting surfaces. The adhesive may be applied after the bypass graft has been secured, before or after blood flow has been reestablished.

The vessel reinforcement device may be of a single piece configuration, or may be fabricated from multiple pieces that overlap. The reinforcement, or reinforcements may be as long as the entire length of the bypass graft, or only at the two ends of the anastomosis to function as a strain relief. The vessel reinforcement device can be placed around the bypass graft before the second end of the graft is secured, or after both ends of the bypass graft has been secured if using a version of the reinforcement device that allows side access. The vessel reinforcement device may have a consistent diameter and geometry, or the ends (i.e., the site of the anastomosis) may be flared to fit over the anastomosis to thereby function as an anastomosis reinforcement device. The vessel reinforcement device may be used as a side access version that has the ends directly oppose each other, although they may be offset.

The vessel reinforcement device may be partially or completely made of metal, metal alloy (such as Nitinol), polymer (such as ePTFE), combination of these or other suitable material. The device materials could be in the form of, for example, a wire, hoop, oval, rod, band, ribbon, tube, sheet, combination of these or other suitable shape. Additionally, the materials could be formed in a wound, coiled, undulated, sinusoidal, braided, combination of these or other suitable configuration.

The core material, which may be, for example, Nitinol or other suitable material, is annealed as described herein over a mandrel matching the outer diameter of the bypass graft vessel. The geometry of the mandrel may be round, oval, or of another suitable shape, and may have a consistent size and geometry, or a larger diameter and/or shape, at one or both ends.

The vessel reinforcement device may be partially or completely coated or overmolded using several methods and processes including sintering, molding (such as injection molding), casting, adhesive bonding, laminating, dip coating, spraying as well as composites and combinations thereof and combinations of other methods and processes.

Another accessory to the vascular coupler is a deployment device. Examples of deployment devices have been described above. In general, the vascular coupler is radially compressible in some configurations and can be deployed using fingers, standard surgical instruments (including Rongeur clamp), modified surgical instrument or specially designed tools. Specially designed tools include modified surgical instruments (length, contact area, compression force, compression diameter, etc.), as well as tools/devices specifically designed to compress the cross section of the anastomotic device while being advancing through a hollow, tapered tube. The anastomosis device could be advanced through the deployment tool by an elongated stylet that attaches to the outside of the anastomosis device, inside or outside of the deployment tool. Advancement from outside the deployment tool, using a stylet or plunger, could be accomplished by way of a slot through the wall of the funnel type deployment tool.

The deployment tool may be designed to deflect some or all of the interior vessel engagement elements (i.e., inner or outer clips) into a position that assists deployment (i.e., forward, backward, or other suitable position). Once deployed inside the vessel, the tool is removed from the vascular coupler.

The deployment tools and devices may have the ability for the distal end to be steered (e.g., controllable from the proximal end of the tool or device) while having the ability to compress the vascular coupler during deployment, and release the coupler once it is positioned in the desired location within the vessel. This version of a deployment tool is particularly useful during minimally invasive, endoscopic and robotically assisted surgery, or other where access space within the chest cavity is limited. Steering capability can be accomplished using one or more pull wires attached to a ring, collar, flat leaf spring, or other member that is designed to deflect when the pull wire is pulled. Alternatively, the distal section of the deployment tool/device can be formed in a curve, and a straight rod or stylet can be advanced from the proximal end, towards the distal end, straightening the distal end. Another option is to advance a preformed curve, or steerable device, into a lumen of the deployment tool/device. A clip that can be removed from the side after deployment also can be used.

The vascular coupler is versatile and can be deployed in a number of methods, some of which have been described above or are described below. To access the heart, the surgeon uses a thoracotomy, thoracostomy, or median sternotomy, or other suitable surgical approaches. The vascular coupler and accessories described herein can be used with cardiopulmonary support, beating heart, open field, minimally invasive, endoscopic, laparoscopic and robotically assisted surgery, or other cardiovascular technique.

The bypass graft is prepared by cutting a graft to the desired length, and the ends are cut to the desired angle (e.g., 30 degrees or other suitable angle). Further, additional cuts, such as a longitudinal cut, may also be made to the ends of the graft to produce the desired final geometry, or for other surgical or therapeutic purposes. The vascular coupler is sized according to the type, size and anastomosis location. The vascular coupler then is loaded and secured to the bypass graft by way of securing members, an adhesive in and/or on the tissue contacting surfaces, and/or by using one or more sutures (e.g., tissue penetrating or non-penetrating sutures). Alternatively, adhesive can be applied to the vascular coupler after the coupler has been loaded and secured to the bypass graft. The tip of a vascular dilator or other suitable instrument may be inserted into the bypass graft lumen, gently expanding the end diameter of the graft into contact with the inner diameter of the vascular coupler, securing the coupler to the bypass graft. Alternatively, the bypass graft may be positioned and secured over the vascular coupler, and secured with adhesive already on or in the coupler, and/or may be applied after positioning. The adhesive used typically will be selected for its ability to withstand submersion in papaverine or other solution just prior to implantation.

The tissue may need to be stabilized. For example, a localized tissue-stabilizing device may be used during the coronary bypass procedure. One or more stabilizing devices could be positioned on the surface of the heart, in parallel with the coronary artery, at the site of the anastomosis. The stabilizing devices can access the internal cavity through one or more locations, and can be attached on the proximal end to a retractor, or other arm, rail or other stabile platform, inside or outside of the patient's body. The localized tissue stabilizer may be positioned, adjusted, and locked into any direction and position. The adjustment includes, but is not limited to, the width in between the tissue contacting sections, and the amount of compression and stabilization on the heart surface.

Typically, a proximal aortotomy is made in the aorta. This generally is termed the proximal anastomosis site. The initial puncture is typically made in the aorta using a scalpel blade, followed by rapid insertion of an aortic punch at the site of the incision. The punch is used to create a hole of the appropriate size and geometry. Once the hole has been made, the punch is removed and the proximal vascular coupler with an attached bypass graft is deflected and inserted into the opening. The compressing or restraining (deflecting) force on the vascular coupler then is removed so that the vascular coupler is allowed to expand and engage the horizontal and vertical planes of the anastomosis site. This engagement creates a hemostatic seal between the wall of the aorta and the anastomotic device.

Alternatively, an aortic punch with a forward leading edge scalpel blade, or other sharp point can be used to form the aortotomy and punch using the same device.

The surgeon forms a distal anastomosis, typically in a coronary artery. This site is generally termed the distal anastomosis site. The arteriotomy is typically created using the tip of a scalpel blade for the initial puncture, and then using surgical scissors (e.g., Potts type or other suitable scissors) to increase the longitudinal length of the incision. The scissors may include reference measurement numbers that the surgeon can use when creating the arteriotomy. Once the arteriotomy has been made, the anastomosis site maybe held open with a spreader, making it easier for the device to be inserted.

Alternatively, an automatic arteriotomy device may be used. The device would have the ability to make a predetermined length cut, preventing the arteriotomy from being made too long. As noted above, if the arteriotomy is too long, it may be difficult to achieve hemostasis after the device has been deployed.

For most coronary artery bypass grafting (CABG) procedures, the distal (coronary) anastomosis is performed first, followed by the proximal (aorta) connection. Once the bypass graft has been prepped, the end of the anastomosis device (containing the end of the graft) is compressed or deflected forward to produce a smaller cross section and inserted into the coronary artery through the arteriotomy. The device can be compressed by the surgeon using fingers, a common surgical tool, a modified surgical tool, or special deployment tool. The anastomosis device has geometric design features and other that prevents positioning the device too far into the artery, and is designed to expand and engage the artery wall (vertical, and or horizontal engagement), once the compressive force has been removed. Once positioned, the device can be held in place as the adhesive, on or in the tissue contacting surfaces, cures, providing acute hemostasis and mechanical securement to the arterial wall. A similar process is used to make the proximal (aorta) anastomosis. Acute hemostasis can also be realized by mechanical expansion, and or geometric interference fit alone.

Additional securement/reinforcement can be used (if desired). For example, a biocompatible adhesive can be applied around the site of the anastomosis, a suture (such as a purse string or other type of configuration) can be applied, combination of these or other suitable methods.

An external strain relief can be positioned around the bypass graft before, during or after the CABG procedure has been completed. Adhesive could be used to bond the securement device/strain relief to the bypass vessel.

There are additional techniques that are typically considered when deploying the vascular coupler. These techniques are the push in/pull out technique and the deflection technique.

The push in/pull out technique has been briefly described above, but is presented here in greater detail. When inserting vascular coupler into the hole or slot of the vessel, the hinged elements will tend to deflect backwards until the device is inside the target site. The vascular coupler can then be gently pulled back to "seat," or position in the final location between the tissue (vessel) wall. The longer hinged elements, petals, or clips (i.e., inner members having, for example a U-shape or paper clip configuration) prevent the device from coming out of the target area when pulling back. Then, when further gently retracting the vascular coupler away from the vessel, the shorter, outer elements (i.e., paper clip-shaped element, U-shaped element) will be released to spring back against the outer wall of the vessel as soon as it is out of the vessel and the larger, inner members will be released outwardly to compress the vessel between them upon release. If a ridge configuration is used instead of the hinged outer elements, the hinged inner elements will compress the vessel wall between the ridge and the inner elements.

The deflection method requires the use of a disposable, single use only, circular clip or partial ring ("C" geometry, or other) tool, designed to deflect a portion, or the complete hinged element, forward, backward, or combination during insertion. The width of the deployment clip is shorter than the length of the hinged elements, and is removed, preferably from the side, once the distal ends of the hinged elements are inside the target area (i.e., vessel). This deployment tool is described in greater detail above.

The distance between the overmolded ridge/tissue contacting/reinforcing ridge, and the top of the petals is anticipated to be available in different distances, to produce different compressive forces—depending on the vessel thickness, the shorter the distance between the ridge and petals, the higher the compression between the outside and inside of the vessel. This distance may also be adjustable just prior to implantation. Availability to optimally compress several different vessel thicknesses, custom and or adjustable vessel compression feature. Tissue compression modified by different ridge to petal distances.

The securing members and petals can be individual elements, or connected, partially or completely continuous. The securing members and petals may be made from the same or different materials (for example, the petals can be made from Nitinol, and the securing members can be made from stainless steel).

There are additional utilities and uses for the vascular coupler. For example, there can be a sutured anastomosis site reinforcement. In this configuration, a version of the vascular coupler (and or strain relief) with or without side access slit or other, to be placed (from the side or over the top) and secured to site after the bypass graft to host vessel anastomosis has been sutured, to prevent kinking, bypass graft closure, vessel "ballooning," due to a compliance mismatch, etc. Another use is to create an anastomosis through a graft that has been deployed in the abdominal aorta, reattaching vessels that would have otherwise been occluded by the graft. The opposite end could be attached using an end-to-end anastomosis device.

The vascular coupler can be used as an arterial to venous shunt for hemodialysis, AV fistula, and pulmonary uses. The vascular coupler and techniques can be used for cardiovascular, gastrointestinal, neurological, reproductive, lymphatic, respiratory or other applications where partial or complete, temporary or permanent closure, compression, sealing or reinforcement is desired. Additionally, any lumen, duct, organ, hollow body organs or cavity, or other structures or tissues, where partial or complete, temporary or permanent sealing, crimping, compression, plugging, reinforcement or other purpose is desired. The coupler, with or without modifications, may be used as a stent in an ostium anywhere in the body, but especially in the aortic ostium. The expanding members could act as a stop, so as not to insert the stent too far into the coronary artery. The coupler can be deployed either percutaneously (with a catheter), or during a surgical procedure with a hand held tool, or by hand.

Alternatively, the device could be used as a conduit, conduit support and or reinforcement by itself, or used with a synthetic and or autogenous/autologous conduit or lumen. For conduit or conduit reinforcement applications, the material and design used would be sufficiently flexible, but resistant to kinking and or compressive closure. The device may be used completely or partially, outside, inside, in between, or combination with any lumen, vessel, duct, organ, hollow body organs, cavity, and or other structures or tissues within the body.

The coupler may be closed off if the bypass graft becomes occluded, or for any other reason, by the use of a cap, clamp, adhesive, combination or other method. A new bypass graft may be attached to the original coupler, or attached to a new coupler and inserted inside or near the original coupler. If the new coupler is intended to be inserted into the original coupler, the new coupler may be adapted to be secured inside by a gasket type material around the outside (to produce a mechanical and fluid tight seal), engaging elements, interlocking elements, adhesive, combination or other suitable design and method. The coupler also can be used as a temporary holding device for indwelling catheters, cannula, introducers or other devices. The coupler may be used to hold a catheter or other, at a fixed or movable length from the outside of a patient. The catheter or other may be inserted through the center of the coupler, with the tissue contacting ridge attached to the skin using an adhesive, suture(s), combination or other. The inside of the coupler may have a valve, ring, gasket or other, that provides fluid sealing as well as mechanical interference fit between the inside of the coupler and the outside of the catheter or other device.

Alternatively, the coupler may be configured to compress onto itself, providing closure, compression, sealing or reinforcement for any lumen, duct, organ, hollow body organs or cavity, or other structures or tissues, where partial or complete, temporary or permanent sealing, crimping, compression, plugging, reinforcement or other purpose is desired.

The vascular coupler also can have the following features, concepts, and configurations, as necessary and desirable. For example, the vascular coupler can be partially or completely made using several methods and processes including extrusion, sintering, molding (injection and other), casting, adhesive bonding, laminating, dip coating, spraying as well as composites and combinations thereof and combinations of other methods and processes.

The vascular coupler can be fabricated using injection-molding or overmolding techniques. The molds would be designed to mold the device material, inside, outside, in-between, around, etc. the superelastic/shape memory (or other material) elements, making the elements an integral part of the device. In general, the steps are as follows: an injection mold is prepared, having the general characteristics that will result in a device shown in the drawing sections. The superelastic/shape memory elements are placed at desired locations in the mold. The desired polymeric material is then injected into the mold with the elements in place, prevented from moving, so that they are integrated into the mold. The injected material is allowed to cure, and the device (with the elements) is removed.

Any area or region of the device may be biased in a direction (or directions) to increase the contact or holding/compression force, or for other purposes, than without the biased configuration (increase compression force) once the device has been deployed (or when the bypass graft is loaded onto the device, in the case of the stem).

A compliant material may be added to any or all areas of the device (stem and or petals), to aid sealing between the vessel and the device (similar to a gasket). For example, the compliant material may be applied to the region in between the inner and outer petals, and or one or both of the inner and outer vessel petals. The compliant material may also have one or more grooves, slots or other, to assist with hemostasis, prevent slippage, and or any other purpose. The compliant material may be, or contain, an adhesive or therapeutic substance. The compliant material may be added to the device by dip coating, spraying, brushing, molding, combination or any other method.

The stem may be overmolded or have a second piece jacket that would have a lip or other feature that would contact the top of the vessel, to prevent, or stop the vessel from splitting, as well as to reinforce the anastomotic site. Adhesive may be located on the bottom, vessel-contacting surface, or may be applied after deployment. If the piece is separate from the device, it may be placed around the bypass vessel before the two ends are secured, or placed from the side (slot or slit through the side of the piece). The tissue contacting area may be biased in such a way (downward) that may increase the tissue contacting force. Jacket may be reinforced with superelastic/shape memory materials, or other, and may be overmolded with silicone, ePTFE, combination or other biologically acceptable material.

Each tissue-contacting element (petal) may have one or more elements. One element may be deflected forward during deployment, with another element, or section of an element, acting as a depth stop to limit insertion. The deflected element may engage the interior of the host vessel.

The host vessel tissue contacting elements(s) may be part of the coupler, separate piece, or combination.

The host vessel tissue contacting elements may be flat, concave, convex, combination or other, at any location.

The host vessel tissue contacting elements may have a radiused (full or other), square, "V," combination, or other tip geometry.

Each host vessel tissue contacting elements may have an inside and outside vessel section, compressing the vessel wall in between. There may be a radiused (or other shape) cut out in the device to better "seat" the end of the vessel in between the host vessel tissue contacting elements. This may also allow the host vessel tissue contacting elements to lay flatter against the vessel wall.

The petals (or horizontal host vessel tissue contacting elements) may have one or more curves ("S," or other shape or configuration), to increase the contact area with the vessel, or other purpose.

A suture (commonly used, NiTi, coil, combination or other) may be used to secure the device to the bypass vessel, device to the host vessel, or both. The host vessel tissue contacting elements may have features such as holes, slots, cut outs reduced width, combination or other, specifically designed to accommodate any type of suture or clip. Alternatively, a standard design device could be used with sutures, at any location, bonding, or assisting with the bonding, of the vessels and the device.

An odd or even number of host vessel tissue contacting elements may be used—matched pairs or other configuration.

Longer and shorter host vessel tissue contacting elements may be used on the same device—they don't have to all be the same length.

The "Bite and Lock" design for one of the tissue penetrating versions of the device—the ends and or sided of the host vessel tissue contacting elements may be designed to fit and lock together during or after deployment.

The external side host vessel tissue contacting elements for the coronary version may extend onto the epicardium. Side host vessel tissue contacting elements may be partially, or completely (substantially) flat. The side host vessel tissue contacting elements may have adhesive on the tissue contacting surfaces, a suture, combination or other may also be used to enhance the contact between the device and vessel wall.

The desired host vessel tissue contacting elements are deflected forward, and the "C" section of the deployment tool is snapped, or positioned (from the side or top) around the desired host vessel tissue contacting elements of the device.

Simple, disposable, hand-held tool, designed to deflect one or more host vessel tissue contacting elements (and/or host vessel tissue contacting elements component) forward during insertion into the host vessel (deployment) and be removed from around the host vessel tissue contacting elements. The "C" section (constraining) of the tool may have weakened areas (reduced wall and or width) that assist in removing the simple deployment tool from the device (acting as a hinge). The tool may also have a means to separate the anastomotic device from the deployment tool, such as a pin that could pass through the deployment tool, contacting and pushing the device from the tool, as the pin or other is depressed.

The deployment tool may be plastic, and or have plastic, rubber, or other non-metallic surface at the device contact areas so as not to scrape, or otherwise remove the oxide from the surface of the NiTi device.

The deployment tool may incorporate a tissue-stabilizing feature, to assist deployment on a beating heart (features and designs may be similar to those produced by Medtronic, Guidant or other, and may include vacuum and or mechanical, or other, stabilization).

The vascular couplers described herein can provide numerous advantages. For example, the couplers can be a single piece coupler. No collar may be required to secure a bypass vessel to the coupler. The primarily metallic coupler has interior and exterior vessel engagement/supports on the same host vessel tissue contacting elements. Some versions of the couplers do not require a deployment tool and can be inserted and secured by hand. The deployment devices and methods do not expand, dilate, enlarge or otherwise exert radial force on the arteriotomy or aortotomy. No sheath is required for deployment of the couplers. The deployment system engages and releases the couplers from the side, not through a circumferential sheath. For the primarily metallic coupler, some of the host vessel tissue contacting elements are deflected forward for deployment, and some are left in the as annealed position, which acts as a depth stop to prevent over insertion of the coupler into the vessel. The overmolded ridge covers, and can be bonded to the tissue surrounding the arteriotomy or aortotomy, reinforcing the area and preventing any enlargement of the vessel access punch or incision. The coupler host vessel tissue contacting elements design compensates for any irregularities in the arteriotomy and or aortotomy, as well as the vessel wall.

In general, the stem of the vascular couplers may be overmolded straight, sinusoidal, a combination of these configurations, or any other suitable geometry. For example, to increase the compliance of the vascular couplers, the stem may be formed with longitudinal slots that run the length of the stem but do not cut entirely through the stem. The stem also can be configured as a surface for suturing the coupler to the bypass vessel wall. As with other areas on the coupler, holes, slots, grooves, reduced wall sections, or other openings or slots may be included on the stem to locate a running or interrupted suture or assist the physician's use of a running or interrupted suture.

In some of the above configurations, the overmolded stem may have a groove, slot, and or slit in-between the inner and outer wall of the stem. This space may be used to insert and secure a bypass vessel or a bypass graft to the coupler, using an interference fit, compression, adhesively bonded, suture, or combination of these or other suitable connecting means.

The circumferential ridge (i.e., outer vessel ridge) may be an integral part of the stem or may be a separate piece that is separately molded or adhered to the stem. The circumferential ridge functions as a top vessel contacting ridge to reinforce the anastomotic site, as well as to act as a depth stop to limit coupler insertion into the artery. The ridge can be completely or partially circumferential and may be reinforced (as described below). The ridge also can have a threaded region, such as a diagonal slot through the ridge, which allows a twisting movement to back out the ridge from inside the vessel during a push in—partially pull out deployment method. The ridge also can function as a surface for suturing the vascular coupler to the host vessel wall. As with other areas of the coupler, the ridge can include holes, slots, grooves, reduced wall sections, or other openings to locate and assist in the use of a running or interrupted suture. The vascular couplers above can be modified such that the ridge can be used with a suture, or to better enable suturing, to attach the bypass to the host vessel. In place of or along with the suture, an adhesive may be used as previously described. For example, a woven Dacron fabric can be adhered to the ridge such that vessel can be sutured or adhered to the Dacron fabric to attach the vessel to the ridge. Moreover, to assist with acute hemostasis, a compliant "gasket" can be molded or adhered under the overmolded ridge—the gasket may also be part of the overmolded component. The gasket can be, for example, the same material as previously described, including silicone, polyurethane, combination or other suitable material. Moreover, as described above, the bypass vessel or bypass graft may be attached to the inside, outside or in-between the stem of the vascular coupler. The attachment between the bypass graft and coupler may be completely based on or augmented by a mechanical interference fit, one or more sutures, an adhesive, a combination of these methods, and/or any other suitable method.

One or more sections of the ridge, as well as the entirety of the overmolded section of the coupler, may include a reinforcing layer or layers of material, such as woven Dacron, ePTFE, a combination of these, or other suitable material. The materials strengthen the ridge, thereby reinforcing or preventing the suture from pulling out and away, which may split the compliant ridge. The reinforcement material may be positioned on the top, bottom, in between, or combination of sections of the ridge and/or overmolded section or sections of the coupler. The suture reinforcement also may be formed in the shape of a partial or complete hoop or other structure.

In general, the multiple element version of the coupler may be fabricated with individual petals or petals that are formed as a group of more than one petal. The vascular coupler may be fabricated by overmolding of, e.g., a polymer to secure the petal or petal groups together to form the stem of the coupler. The petals or petal groups may also be joined together with a hoop configuration that may be split (i.e., open), completely closed circumferentially, or other configuration between these two configurations before being overmolded. The coupler petals may be fabricated as part of the stem, attached to the stem, and/or as separate pieces which are then joined to the stem. The end of the petals that are oriented away or outwardly from the stem can be further away (i.e., wider) as they extend from the stem.

By using multiple independent petals, the vascular coupler advantageously is configured for complete or greater than circumferential vessel contact at the site of the aortic punch or core site, and the arteriotomy for the coronary anastomosis.

As described above, the stem and petals may be fabricated from a material that has a round, flat, concave, or convex geometry. Of course, materials of other geometries can be used. Similarly, although the overmolded vascular coupler has been illustrated using individual petals, the petals described previously (e.g., paper clip, two elements on one petal) also may be used with the overmolded versions of the coupler.

The petals for the overmolded version can be formed as coils and advantageously have very minimal foreign material on the inside of the vessel. The coil wire used to fabricate the petals can be round, oval, or a combination of these or other geometries. Similarly, the coil wires may be made from single or multiple wires or a combination of these configurations or other continuous or interrupted wire configurations.

The coil wind angle may be consistent, and or varied. In this manner, the wider the separation between the coil winds, the more flexible the section (or region) in which the coil winds are positioned.

One, nearly complete circumferential loop (or other) of wire from the coupler provides the interior vessel contact. More than one wire may be used to create multiple, independent, partial circumferential vessel contacting elements that together may be nearly, or more than 360 degrees or other.

The coil wire used to fabricate the petals can be made of a material as described herein. For example, in version, the material may be a NiTi wire that has been electropolished and heat formed (as disclosed in detail above) around a suitable fixture or tool.

If a coiled strain relief is located above the overmolded stem, the coil strain relief may be on the inside or outside of the vessel and be secured with an adhesive, suture, or other attachment means, as described above.

In general, the vascular coupler can be deployed using a number of methods. For example, the vascular couplers may be deployed using any of the tools and techniques describe above. Examples of suitable method include the push in-pull out deployment technique, deflecting forwardly the interior vessel components, rotating the coupler during insertion, deploying by hand, and/or compressing the stem, Radiopaque material such as barium sulfate, bismuth trioxide, tantalum or other can be added to the vascular couplers described herein, reinforcement structure or bonding material. Additionally, platinum, gold, or other material may be added to the device by sputter coating, ion deposition, vapor deposition, combination, or other process.

In general, the bypass vessel can be attached to the vascular couplers and the vascular couplers can be attached to the host vessel using sutures, staples (e.g., tissue penetrating and or non tissue penetrating), clips (e.g., tissue penetrating and or non tissue penetrating), adhesives, mechanical compression, combination or other. The bypass graft can be attached to the vascular couplers on the outside, inside, or in between.

In general, the securing members for the couplers described herein can be tissue penetrating or non penetrating. The securing members can be any shape, such as flat, round, concave, convex, oval, combination or other. The securing member(s) may have a single end, or a "U," "V," or other shape, including a "paperclip" type configuration. The securing members may be separate individual pieces, or attached to the petals, and overmolded. Alternatively, the securing members (individual or attached to the petals or other) may be separate from the coupler and crimped, allowed to self recover (for the superelastic/shape memory version) or otherwise bonded to the coupler. The securing member(s) may be connected to the petals (single piece), and or stem, or may be a separate element, or combination. The securing member(s) may be in the shape of a "J", "U" or other suitable shape or design. For "U" or other type securing member(s) that are separate from the coupler prior to attachment, the overmolded ridge may have a section (or sections) removed, to allow the outside of the securing member(s) to be of longer length, and lay against the coupler surface. The securing members may have horizontal and or diagonal (or other) slots, grooves or other, on one or more surfaces, to prevent slippage. Adhesive may also be used to assist the securing members' attachment to the tissue, or to the coupler. Deformable securing member(s) may be separate, independent piece(s) that are used to attach the bypass vessel to the coupler, and are applied using a hand tool (crimper, or other). Superelastic/shape memory securing member(s) may be separate, independent piece(s) that are used to attach the bypass vessel to the coupler, and are applied using a hand tool (crimper, or other). The securing member(s) may be designed and used to penetrate the tissue, compress the tissue against the coupler, or combination. The securing member(s) may be the same material as the petal and or stem, or different. The securing member(s) may be a metal, metal alloy, combination or other. The securing member(s) may be Nitinol, and automatically compress the vessel to the coupler when a deflecting force (during the loading process) is removed (through the fixturing/annealing/quenching and repeating the process if desired), or stainless steel (or other) that is bent, compressing the vessel to the coupler. The securing member(s) may be metal, metal alloy, or other as previously described for the coupler, or coupler element. The securing member(s) may also be covered or coated with an adhesive, biocompatible material, therapeutic material, combination or other, as previously described. Any bare metal on the securing member(s) may be electropolished.

The securing members may be overmolded with the coupler instead of separate members. As previously disclosed, the bypass vessel can be placed on the inside or outside of the stem (may be the same or different version of the coupler, and or securing member(s), depending on if the vessel is on the inside or outside of the stem). If the vessel is placed on the inside of the coupler, the securing member(s) may be held open (deflected) with a tool, fingers, and or fixture. The distal vessel edge is positioned, against or near the securing member(s). The deflection force is removed, allowing the securing member(s) to return to the annealed configuration, compressing the vessel wall against the coupler body. The same configuration can be used or modified for use when the bypass graft is on the outside of the coupler stem.

One or more bendable securing members can be used to attach the graft to the coupler. In this case, the bypass vessel can be placed on the inside or outside of the stem (may be the same or different version of the coupler, and or securing member(s), depending on if the vessel is on the inside or outside of the stem). If the vessel is placed on the inside of the coupler, the vessel is positioned against or near the securing member(s). The securing member(s) may be in an open position, to assist with the insertion and positioning of the vessel edge. Once positioned, the securing member(s) may be bent against the vessel, compressing the vessel against the coupler, by using a tapered dilator (or similar instrument) inserted into the inner diameter of the coupler, until the outer surface of the dilator contacts and forces the securing member(s) against the vessel. If the vessel is placed on the outside of the coupler, the vessel is positioned against or near the securing member(s). The securing member(s) may be in an open position, to assist with the insertion and positioning of the vessel edge. Once positioned, the securing member(s) may be bent against the vessel, compressing the vessel against the coupler, by using fingers or a tool.

The inside diameter of the coupler may be straight, flared, combination or other.

No dilating member needed or required before or during the deployment of the coupler.

The petal element(s) of the overmolded coupler may be movable through, or alongside, the wall of the overmolded body during deployment. While the coupler is positioned over the incised (or punched) vessel, the proximal ends of the petal elements may be advanced (one at a time, more than one, or all at once) through the stem, with the distal petal end protruding through the bottom of the coupler, advancing into the vessel and coming into contact with the vessel wall. The proximal ends of the petal elements may be secured in place by mechanical interference fit, adhesive, combination or other suitable designs or methods. This embodiment would work well with petals made from superelastic or shape memory materials (specifically, but not limited to, Nitinol).

When using petals (or other coupler component(s)) made from shape memory Nitinol, the petals (and or other component(s)) may be activated to bend/expand outward and engage the host vessel, from a straight or other configuration, by temperature when the petals come in contact with blood. The petal elements may be flat, angled, concave, convex, combination or other geometry. Individual petal elements may be grouped together with more than one petal, for example within the overmolded section or sections of the coupler.

The tissue securing members may be assisted by the use of an adhesive, interior coupler geometry, combination or other, to provide a fluid tight seal between the bypass graft and coupler. The securing members further may be activated to contact/secure the bypass graft to the coupler by temperature (shape memory), when using securing members made from Nitinol. The securing members may be initially bent using a dilator-like tool, and followed up with a hemostat or other similar instrument, to further bend the securing members against the vessel wall. The securing members may be incorporated in the metallic tube version of the coupler. The securing members may be formed at the same time as the petals are formed (laser, wire EDM, chemical etching, combination or other) from the tubing. Alternatively, the securing members may be separate pieces.

The overmolded coupler may be formed over the petals, securing members, etc., or molded as a separate piece and the various components (such as petals, securing members, etc.) added as a second process. The overmolded coupler and or tissue contacting/reinforcing ridge sections may contain pores or holes through the wall, sufficient to feed new intima growth from outside of the vessel, so that endothelial cells may attach, or for any other purpose. The pore size may be in the range of 5 to 80 microns, with 30 microns being optimum. The pores or holes in the structure may be inherent in the material, present as the result of weaving, braiding, expanding material processing (such as ePTFE) or other process or method, or produced as a secondary process, such as laser, or by any other suitable process. The overmolded body may be produced by using a sintering process around any coupler component. The overmolded section or sections may contain holes, grooves, slots reduced thickness areas, combination or other, to modify the rigidity/flexibility/compliance of the section or sections, or for any other reason.

If a hemostatic gasket is used, it may be part of the overmolded body, tissue contacting/reinforcing ridge or any other component. Alternatively, it may be a separate piece. The gasket may be made from any of the previously disclosed materials, and or any suitable material. Any portion of the gasket may be flat, concave, convex, combination, or any other suitable geometry.

The top vessel reinforcing ridge may be part of the overmolded body, or a separate piece. The top vessel reinforcing ridge may be biased toward the vessel, to increase the compression between the vessel wall. Top vessel reinforcing ridge may prevent the coupler from rotation once deployed/implanted. The top vessel reinforcing ridge may be a different geometry and or material than the coupler stem. The top vessel reinforcing ridge may be oval or elongated, to be parallel with the vessel (coronary for example). The top vessel reinforcing ridge may be flat, angled, concave, convex, combination or other geometry. When viewed from above, the top vessel reinforcing ridge may be completely circumferential, an incomplete circle, sinusoidal, and or have one or more cut out areas (for crimped securing members, flexibility, or for any other purpose). The top vessel reinforcing ridge may have protrusions, on the tissue contacting surface that may be of sufficient length, and may be employed to prevent/limit coupler rotation once deployed onto (into) the host vessel.

Holes, slots, grooves, concave areas or regions, or other shapes may contain a therapeutic agent, bonding agent, combination or other, on or inside any section, region or component of the coupler. Materials, coating or coatings may be contained or applied to any area, region or component of the coupler to reduce or prevent post implant adhesions. Any coupler surface may be textured for any purpose (such as to encourage neo intimal, and or endothelial growth). When using deformable securing members to secure the bypass graft to the coupler, the crimping tool (modified hemostats or other) may have a stop, or other, to limit the amount the securing member can be compressed, to prevent over crimping and damage or weakening to the securing member that may result.

The coupler regions/components may be produced from different materials with different physical properties. For example, the external vessel ridge may be completely or partially made from a softer or harder material than the stem.

The petals produced from a sheet (for example using chemical etching or other as previously described), may include a secondary process to join at least one section to another section (one edge to a second edge or end). The secondary process may include inserting one end (including a tab) into a slot, groove, hole or other, soldering, welding, adhesively bonding, combination or other suitable process. Alternatively, the section or sections may not be bonded, or other wise attached together. This design may allow additional flexibility at one or more regions of the coupler (overmolded or non-overmolded).

The top vessel reinforcing ridge may have the same, smaller or larger diameter as the deployed petals. The ridge may have at least one section or surface that is flat, concave, convex, combination or any other suitable geometry, to provide/assist with the vertical compression for coupler securement and or acute hemostasis.

The stem/strain relief may be produced in one configuration, and designed to bend or deflect, but not kink, once a bypass graft has been attached to the coupler and implanted into a host vessel. For example, the coupler stem and or strain relief may be produced at a 90° angle, but deflect (again without kinking) to approximately 45°. This may be accomplished by reducing or eliminating at least one section or region in the wall of the stem, or alternatively, reinforcing at least one section or region of the stem/strain relief wall. The stem/strain relief may include an elbow or other suitable geometry—straight or combination. The stem/strain relief may be any angle (measured from the reinforcing ridge to the end of the stem/strain relief), and may be the same or different than the angle between the petal and the reinforcing ridge. For example, the vessel petal and the exterior reinforcing ridge may be aligned so that the outside edges of each are parallel, while the angle of the stem/strain relief may be at a 45° (or other suitable) angle.

The stem, strain relief, overmolded ridge, combination or other section, region or area of the coupler may contain at least one component or element, designed for any desirable purpose including the ability to expand and contract, producing a kinetic, dynamic, radial spring action, and or response to deflection, similar to a natural or sutured anastomosis.

The coupler may be packaged already attached to the deployment tool. Alternatively, the coupler could be inserted/attached/loaded in the deployment tool just prior to deployment.

Another coupler fabrication method includes stereo lithography (3-D layering) to partially or completely produce any or all coupler component(s) (stem and ridge section for example). The stereo lithography process may envelop/secure at least one or more tissue contacting elements, or other components that may be covered, partially or completely by the SL process. The process may also produce cavities for the later insertion/securing of coupler components (securing members/petals, etc.) as a secondary process.

The types of couplers described herein can be coronary, aortic, peripheral, valved, and other. The versions can be end to side, end to end, side to side. The coupler groups include sutureless or sutured. The coupler design options may have a diameter: 1.0 mm to >8 mm; geometry: Concentric, oval, combination or other, angle: 20° to 90° or other, and stem length: 0 mm to 8 mm or larger. The deployment methods include: (1) Compression of stem (using fingers or tool); (2) Forward deflection of inner vessel elements; (3) Remove simple tool from around coupler side, allowing superelastic petals to return to non-constrained configuration, engaging vessel wall; (4) shape memory petals recover to annealed position once inside vessel (using the bodies own heat, or by using a secondary heat source); (5) Push in, partially pull out; (6) Twist during insertion; and (7) Remote deployment devices and methods of use (to enable use of coupler during minimally invasive, endoscopic, laparoscopic, robotically assisted, catheter-based, as well as other types of procedures).

While several particular forms of the invention have been illustrated and described, it will be apparent that various modifications and combinations of the invention detailed in the text and drawings can be made without departing from the spirit and scope of the invention. For example, references to materials of construction, specific dimensions, and utilities or applications are also not intended to be limiting in any manner and other materials and dimensions could be substituted and remain within the spirit and scope of the invention. For example, the everted versions of the couplers without petals but having reinforcing ridges, described herein, can be joined together. The ridges are adhered together, as described herein, and the everted edges of the vessels are thereby placed in contact to provide an end-to-end anastomosis. Finally, it is contemplated that any single feature or any combination of optional features of the inventive variations described herein may be specifically excluded from the claimed invention and be so described as a negative limitation. Accordingly, it is not intended that the invention be limited, except as by the appended claims.

What is claimed is:

1. A coupler configured to connect a first tubular vessel to an aperture in a second tubular vessel, the coupler comprising:
   one or more radially extending members;
   a substantially nonmetallic tubular member, the tubular member comprising an outer wall, an inner wall defining a lumen having an open distal end and an open proximal end, and a circumferential ridge encircling the outer wall, a distal portion of the radially extending members extending from the distal end of the tubular member and a proximal portion of the radially extending members being fixed within the tubular member; and
   at least one securing member mounted to the distal end of the tubular member, the securing member comprising a first segment positioned adjacent to the inner wall, a second segment positioned against the outer wall, and a third segment connecting the first segment and the second segment.

2. The coupler of claim 1, wherein the extending member comprise a first segment and a second segment, the first segment being at an angle of 90° or less with respect to the second segment, the first segment extending from the tubular member.

3. The coupler of claim 1, wherein the extending member comprises a nickel titanium alloy.

4. The coupler of claim 1, wherein the extending members comprise 17-7PH stainless steel.

5. The coupler of claim 2, wherein the second segment defines a region that is wider than a region defined by the first segment.

6. The coupler of claim 1, wherein the proximal end of the tubular member comprises a strain relief.

7. A coupler configured to connect a first tubular vessel to an aperture in a second tubular vessel, the coupler comprising:
   one or more radially extending members;
   a substantially nonmetallic tubular member, the tubular member comprising an outer wall, an inner wall defining a lumen having an open distal end and an open proximal end, and a circumferential ridge encircling the outer wall, a distal portion of the radially extending members extending from the distal end of the tubular member and a proximal portion of the radially extending members being fixed within the tubular member; and
   at least one securing member mounted to the distal end of the tubular member, the securing member comprising a first segment positioned adjacent to the inner wall, a second segment positioned within the wall between the inner wall and the outer wall, and a third segment connecting the first segment and the second segment.

8. The coupler of claim 1, further comprising a gasket extending from the distal end of the tubular member, the radially extending members extending from the gasket.

9. The coupler of claim 1, wherein the tubular member comprises one or more of silicone, ePTFE, polyurethane, and polyisoprene.

10. The coupler of claim 1, further comprising a gasket extending from the distal end of the tubular member and a strain relief extending from the proximal end of the tubular member, wherein the tubular member, the ridge, the gasket, and the strain relief are an integral unit.

11. A method of deploying a coupler, the coupler comprising one or more radially extending members, a substantially nonmetallic tubular member and at least one securing member, the tubular member comprising an outer wall, an inner wall defining a lumen having an open distal end and an open proximal end, and a circumferential ridge encircling at least a portion of the outer wall, a distal portion of the radially extending members extending from the distal end of the tubular member and a proximal portion of the radially extending members being fixed within the tubular member, and the at least one securing member being mounted to the distal end of the tubular member, the securing member comprising a first segment positioned adjacent to the inner wall, a second segment positioned against the outer wall, and a third segment connecting the first segment and the second segment, the method comprising:
   forming an opening in a wall of a tubular vessel;
   deflecting the radially extending members into a longitudinally extending configuration;
   inserting the extending members at least partially into the opening; and
   releasing the extending members such that the extending members return to the radially extending configuration from the longitudinally extending configuration, whereby the wall of the tubular vessel is compressed between the radially extending members and the circumferential ridge.

12. The method of claim 11, wherein deflecting the radially extending members into a longitudinally extending configuration further comprises deflecting the radially extending members and at least partially inserting the extending members into an opening in a deployment tool, the deployment tool comprising a handle and a distal plate, the distal plate including the opening.

13. The method of claim 12, wherein releasing the extending members further comprises placing the plate on the vessel and removing the plate from around the coupler, the removal of the plate allowing the extending members to return to the radially extending configuration.

14. The method of claim 11, wherein at least one component of the coupler comprises one or more therapeutic agents.

15. The coupler of claim 7, wherein the extending member comprises a first segment and a second segment, the first segment being at an angle of 90° or less with respect to the second segment, the first segment extending from the tubular member.

16. The coupler of claim 7, wherein the extending member comprises a nickel titanium alloy.

17. The coupler of claim 7, wherein the extending member comprises 17-7PH stainless steel.

18. The coupler of claim 15, wherein the second segment defines a region that is wider than a region defined by the first segment.

19. The coupler of claim 7, wherein the proximal end of the tubular member comprises a strain relief.

20. The coupler of claim 7, further comprising a gasket extending from the distal end of the tubular member, the radially extending members extending from the gasket.

21. The coupler of claim 7, wherein the tubular member comprises one or more of silicone, ePTFE, polyurethane, and polyisoprene.

22. The coupler of claim 7, further comprising a gasket extending from the distal end of the tubular member and a strain relief extending from the proximal end of the tubular member, wherein the tubular member, the ridge, the gasket, and the strain relief are an integral unit.

23. The coupler of claim 7, wherein at least one component of the coupler comprises one or more therapeutic agents.

24. The coupler of claim 1, wherein at least one component of the coupler comprises one or more therapeutic agents.

25. A method of deploying a coupler, the coupler comprising one or more radially extending members, a substantially nonmetallic tubular member and at least one securing member, the tubular member comprising an outer wall, an inner wall defining a lumen having an open distal end and an open proximal end, and a circumferential ridge encircling at least a portion of the outer wall, a distal portion of the radially extending members extending from the distal end of the tubular member and a proximal portion of the radially extending members being fixed within the tubular member, at least one securing member mounted to the distal end of the tubular member, the securing member comprising a first segment positioned adjacent to the inner wall, a second segment positioned within the wall between the inner wall and the outer wall, and a third segment connecting the first segment and the second segment, the method comprising:

forming an opening in a wall of a tubular vessel;

deflecting the radially extending members into a longitudinally extending configuration;

inserting the extending members at least partially into the opening; and releasing the extending members such that the extending members return to the radially extending configuration from the longitudinally extending configuration, whereby the wall of the tubular vessel is compressed between the radially extending members and the circumferential ridge.

26. The method of claim 25, wherein deflecting the radially extending members into a longitudinally extending configuration further comprises deflecting the radially extending members and at least partially inserting the extending members into an opening in a deployment tool, the deployment tool comprising a handle and a distal plate, the distal plate including the opening.

27. The method of claim 26, wherein releasing the extending members further comprises placing the plate on the vessel and removing the plate from around the coupler, the removal of the plate allowing the extending members to return to the radially extending configuration.

28. The method of claim 25, wherein at least one component of the coupler comprises one or more therapeutic agents.

* * * * *